United States Patent
Tian et al.

(10) Patent No.: US 9,297,796 B2
(45) Date of Patent: Mar. 29, 2016

(54) BENT NANOWIRES AND RELATED PROBING OF SPECIES

(75) Inventors: Bozhi Tian, Cambridge, MA (US); Ping Xie, Needham, MA (US); Thomas J. Kempa, Somerville, MA (US); Charles M. Lieber, Lexington, MA (US); Itzhaq Cohen-Karni, Cambridge, MA (US); Quan Qing, Somerville, MA (US); Xiaojie Duan, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/497,852

(22) PCT Filed: Sep. 24, 2010

(86) PCT No.: PCT/US2010/050199
§ 371 (c)(1),
(2), (4) Date: Jul. 2, 2012

(87) PCT Pub. No.: WO2011/038228
PCT Pub. Date: Mar. 31, 2011

(65) Prior Publication Data
US 2012/0267604 A1    Oct. 25, 2012

Related U.S. Application Data

(60) Provisional application No. 61/245,641, filed on Sep. 24, 2009, provisional application No. 61/326,108, filed on Apr. 20, 2010.

(51) Int. Cl.
| | | |
|---|---|---|
| *B82Y 99/00* | (2011.01) | |
| *H01L 29/06* | (2006.01) | |
| *H01L 21/20* | (2006.01) | |
| *G01N 33/487* | (2006.01) | |
| *B82Y 10/00* | (2011.01) | |
| *B82Y 15/00* | (2011.01) | |
| *H01L 29/04* | (2006.01) | |

(52) U.S. Cl.
CPC .......... *G01N 33/48728* (2013.01); *B82Y 10/00* (2013.01); *B82Y 15/00* (2013.01); *H01L 29/045* (2013.01); *H01L 29/0665* (2013.01)

(58) Field of Classification Search
CPC .. B82Y 10/00; B82Y 15/00; G01N 33/48728; H01L 29/045; H01L 29/0665
USPC ...................................................... 438/1, 478
See application file for complete search history.

(56) References Cited

U.S. PATENT DOCUMENTS

| | | |
|---|---|---|
| 905,586 A | 12/1908 | Rigney |
| 3,873,359 A | 3/1975 | Lando |
| 3,873,360 A | 3/1975 | Lando |
| 3,900,614 A | 8/1975 | Lando |
| 4,341,009 A | 7/1982 | Bartholomew et al. |
| 4,673,474 A | 6/1987 | Ogawa |
| 4,939,556 A | 7/1990 | Eguchi et al. |
| 5,023,139 A | 6/1991 | Birnboim et al. |
| 5,089,545 A | 2/1992 | Pol |
| 5,252,835 A | 10/1993 | Lieber et al. |
| 5,274,602 A | 12/1993 | Glenn |
| 5,332,910 A | 7/1994 | Haraguchi et al. |
| 5,453,970 A | 9/1995 | Rust et al. |
| 5,475,341 A | 12/1995 | Reed |
| 5,512,131 A | 4/1996 | Kumar et al. |
| 5,524,092 A | 6/1996 | Park |
| 5,537,075 A | 7/1996 | Miyazaki |
| 5,539,214 A | 7/1996 | Lynch et al. |
| 5,581,091 A | 12/1996 | Moskovits et al. |
| 5,589,692 A | 12/1996 | Reed |
| 5,607,876 A | 3/1997 | Biegelsen et al. |
| 5,620,850 A | 4/1997 | Bamdad et al. |
| 5,640,343 A | 6/1997 | Gallagher et al. |
| 5,672,480 A | 9/1997 | Dowell et al. |
| 5,726,524 A | 3/1998 | Debe |
| 5,739,057 A | 4/1998 | Tiwari et al. |
| 5,747,180 A | 5/1998 | Miller et al. |
| 5,751,156 A | 5/1998 | Muller et al. |
| 5,776,748 A | 7/1998 | Singhvi et al. |
| 5,824,470 A | 10/1998 | Baldeschwieler et al. |
| 5,830,538 A | 11/1998 | Gates et al. |
| 5,840,435 A | 11/1998 | Lieber et al. |
| 5,847,565 A | 12/1998 | Narayanan |
| 5,858,862 A | 1/1999 | Westwater et al. |
| 5,864,823 A | 1/1999 | Levitan |
| 5,866,434 A | 2/1999 | Massey et al. |
| 5,882,779 A | 3/1999 | Lawandy |

(Continued)

FOREIGN PATENT DOCUMENTS

| | | |
|---|---|---|
| CN | 1110786 | 10/1995 |
| EP | 0622439 A1 | 11/1994 |

(Continued)

OTHER PUBLICATIONS

Huang et al. Nano Letters, 2007, vol. 7, Issue 11, pp. 3355-3359.*
European Office Action for Application No. EP 07852353.7 mailed Oct. 1, 2013.
International Search Report and Written Opinion from International Application No. PCT/US2007/006545 mailed Apr. 10, 2008.
International Preliminary Report on Patentability from International Application No. PCT/US2007/006545 mailed Sep. 25, 2008.
European Office Action for Application No. EP 07861323.9 mailed Jun. 26, 2009.
European Office Action for Application No. EP 07861323.9 mailed Jan. 5, 2010.
Invitation to Pay Additional Fees from International Application No. PCT/US2007/013700 mailed Jun. 11, 2008.
International Search Report and Written Opinion from International Application No. PCT/US2007/013700 mailed Jul. 29, 2008.
International Preliminary Report on Patentability from International Application No. PCT/US2007/013700 mailed Dec. 31, 2008.

(Continued)

*Primary Examiner* — Janet Epps-Smith
(74) *Attorney, Agent, or Firm* — Wolf, Greenfield & Sacks, P.C.

(57) ABSTRACT

Kinked nanowires are used for measuring electrical potentials inside simple cells. An improved intracellular entrance is achieved by modifying the kinked nanowires with phospholipids.

41 Claims, 19 Drawing Sheets

(56) References Cited

U.S. PATENT DOCUMENTS

| | | |
|---|---|---|
| 5,897,945 A | 4/1999 | Lieber et al. |
| 5,900,160 A | 5/1999 | Whitesides et al. |
| 5,903,010 A | 5/1999 | Flory et al. |
| 5,908,692 A | 6/1999 | Hamers et al. |
| 5,916,642 A | 6/1999 | Chang |
| 5,936,703 A | 8/1999 | Miyazaki et al. |
| 5,942,443 A | 8/1999 | Parce et al. |
| 5,985,173 A | 11/1999 | Gray et al. |
| 5,997,832 A | 12/1999 | Lieber et al. |
| 6,004,444 A | 12/1999 | Aksay et al. |
| 6,036,774 A | 3/2000 | Lieber et al. |
| 6,038,060 A | 3/2000 | Crowley |
| 6,060,121 A | 5/2000 | Hidber et al. |
| 6,060,724 A | 5/2000 | Flory et al. |
| 6,069,380 A | 5/2000 | Chou et al. |
| 6,123,819 A | 9/2000 | Peeters |
| 6,128,214 A | 10/2000 | Kuekes et al. |
| 6,143,184 A | 11/2000 | Martin et al. |
| 6,149,819 A | 11/2000 | Martin et al. |
| 6,159,742 A | 12/2000 | Lieber et al. |
| 6,180,239 B1 | 1/2001 | Whitesides et al. |
| 6,187,165 B1 | 2/2001 | Chien et al. |
| 6,190,634 B1 | 2/2001 | Lieber et al. |
| 6,197,515 B1 | 3/2001 | Bamdad et al. |
| 6,203,864 B1 | 3/2001 | Zhang et al. |
| 6,207,392 B1 | 3/2001 | Weiss et al. |
| 6,211,464 B1 | 4/2001 | Mochizuki et al. |
| 6,231,744 B1 | 5/2001 | Ying et al. |
| 6,248,674 B1 | 6/2001 | Kamins et al. |
| 6,256,767 B1 | 7/2001 | Kuekes et al. |
| 6,270,074 B1 | 8/2001 | Rasmussen et al. |
| 6,278,231 B1 | 8/2001 | Iwasaki et al. |
| 6,286,226 B1 | 9/2001 | Jin |
| 6,287,765 B1 | 9/2001 | Cubicciotti |
| 6,294,399 B1 | 9/2001 | Fukumi et al. |
| 6,294,450 B1 | 9/2001 | Chen et al. |
| 6,314,019 B1 | 11/2001 | Kuekes et al. |
| 6,322,713 B1 | 11/2001 | Choi et al. |
| 6,325,904 B1 | 12/2001 | Peeters |
| 6,340,822 B1 | 1/2002 | Brown et al. |
| 6,346,189 B1 | 2/2002 | Dai et al. |
| 6,355,198 B1 | 3/2002 | Kim et al. |
| 6,359,288 B1 | 3/2002 | Ying et al. |
| 6,413,802 B1 | 7/2002 | Hu et al. |
| 6,437,329 B1 | 8/2002 | Yedur et al. |
| 6,440,637 B1 | 8/2002 | Choi et al. |
| 6,451,113 B1 | 9/2002 | Givargizov |
| 6,459,095 B1 | 10/2002 | Heath et al. |
| 6,465,132 B1 | 10/2002 | Jin |
| 6,465,331 B1 | 10/2002 | Keeth et al. |
| 6,468,657 B1 | 10/2002 | Hou et al. |
| 6,468,677 B1 | 10/2002 | Benton et al. |
| 6,503,375 B1 | 1/2003 | Maydan et al. |
| 6,528,020 B1 | 3/2003 | Dai et al. |
| 6,538,367 B1 | 3/2003 | Choi et al. |
| 6,559,468 B1 | 5/2003 | Kuekes et al. |
| 6,586,095 B2 | 7/2003 | Wang et al. |
| 6,628,053 B1 | 9/2003 | Den et al. |
| 6,716,409 B2 | 4/2004 | Hafner et al. |
| 6,741,019 B1 | 5/2004 | Filas et al. |
| 6,743,408 B2 | 6/2004 | Lieber et al. |
| 6,756,025 B2 | 6/2004 | Colbert et al. |
| 6,756,795 B2 | 6/2004 | Hunt et al. |
| 6,762,056 B1 | 7/2004 | Peeters |
| 6,781,166 B2 | 8/2004 | Lieber et al. |
| 6,803,840 B2 | 10/2004 | Hunt et al. |
| 6,808,746 B1 | 10/2004 | Dai et al. |
| 6,815,706 B2 | 11/2004 | Li et al. |
| 6,822,051 B2 | 11/2004 | Harris |
| 6,846,565 B2 | 1/2005 | Korgel et al. |
| 6,846,654 B1 | 1/2005 | Blackburn et al. |
| 6,872,645 B2 | 3/2005 | Duan et al. |
| 6,882,051 B2 | 4/2005 | Majumdar et al. |
| 6,882,767 B2 | 4/2005 | Yang et al. |
| 6,900,479 B2 | 5/2005 | Lieber et al. |
| 6,902,720 B2 | 6/2005 | McGimpsey |
| 6,946,197 B2 | 9/2005 | Yadav et al. |
| 6,958,216 B2 | 10/2005 | Kelley et al. |
| 6,962,823 B2 | 11/2005 | Empedocles et al. |
| 6,963,077 B2 | 11/2005 | Lieber et al. |
| 6,974,706 B1 | 12/2005 | Melker et al. |
| 6,996,147 B2 | 2/2006 | Majumdar et al. |
| 7,048,903 B2 | 5/2006 | Colbert et al. |
| 7,073,157 B2 | 7/2006 | Lieber et al. |
| 7,129,554 B2 | 10/2006 | Lieber et al. |
| 7,172,953 B2 | 2/2007 | Lieber et al. |
| 7,211,464 B2 | 5/2007 | Lieber et al. |
| 7,254,151 B2 | 8/2007 | Lieber et al. |
| 7,256,466 B2 | 8/2007 | Lieber et al. |
| 7,274,208 B2 | 9/2007 | Lieber et al. |
| 7,301,199 B2 | 11/2007 | Lieber et al. |
| 7,303,875 B1 | 12/2007 | Bock et al. |
| 7,335,908 B2 | 2/2008 | Samuelson et al. |
| 7,351,313 B2 | 4/2008 | Hasegawa et al. |
| 7,385,267 B2 | 6/2008 | Lieber et al. |
| 7,399,691 B2 | 7/2008 | Lieber et al. |
| 7,476,596 B2 | 1/2009 | Lieber et al. |
| 7,500,213 B2 | 3/2009 | Lieber et al. |
| 7,595,260 B2 | 9/2009 | Lieber et al. |
| 7,619,290 B2 | 11/2009 | Lieber et al. |
| 7,659,165 B2 | 2/2010 | Koenenkamp |
| 7,795,039 B2 | 9/2010 | Spira et al. |
| 7,911,009 B2 | 3/2011 | Lieber et al. |
| 7,915,151 B2 | 3/2011 | Lieber et al. |
| 8,232,584 B2 | 7/2012 | Lieber et al. |
| 8,575,663 B2 | 11/2013 | Lieber et al. |
| 2001/0054709 A1 | 12/2001 | Heath et al. |
| 2002/0013031 A1 | 1/2002 | Chen et al. |
| 2002/0040805 A1 | 4/2002 | Swager |
| 2002/0055239 A1 | 5/2002 | Tuominen et al. |
| 2002/0084502 A1 | 7/2002 | Jang et al. |
| 2002/0086335 A1 | 7/2002 | Massey et al. |
| 2002/0112814 A1 | 8/2002 | Hafner et al. |
| 2002/0117659 A1 | 8/2002 | Lieber et al. |
| 2002/0122766 A1 | 9/2002 | Lieber et al. |
| 2002/0130311 A1 | 9/2002 | Lieber et al. |
| 2002/0130353 A1 | 9/2002 | Lieber et al. |
| 2002/0146714 A1 | 10/2002 | Lieber et al. |
| 2002/0146745 A1 | 10/2002 | Natan et al. |
| 2002/0158342 A1 | 10/2002 | Tuominen et al. |
| 2002/0172820 A1 | 11/2002 | Majumdar et al. |
| 2002/0175408 A1 | 11/2002 | Majumdar et al. |
| 2002/0179434 A1 | 12/2002 | Dai et al. |
| 2002/0187504 A1 | 12/2002 | Reich et al. |
| 2003/0001091 A1 | 1/2003 | Nakayama et al. |
| 2003/0003300 A1 | 1/2003 | Korgel et al. |
| 2003/0032892 A1 | 2/2003 | Erlach et al. |
| 2003/0048619 A1 | 3/2003 | Kaler et al. |
| 2003/0073071 A1 | 4/2003 | Fritz et al. |
| 2003/0089899 A1 | 5/2003 | Lieber et al. |
| 2003/0098488 A1 | 5/2003 | O'Keeffe et al. |
| 2003/0113713 A1 | 6/2003 | Glezer et al. |
| 2003/0113940 A1 | 6/2003 | Erlanger et al. |
| 2003/0121764 A1 | 7/2003 | Yang et al. |
| 2003/0124509 A1 | 7/2003 | Kenis et al. |
| 2003/0124717 A1 | 7/2003 | Awano et al. |
| 2003/0129087 A1 | 7/2003 | Barbee, Jr. et al. |
| 2003/0134267 A1 | 7/2003 | Kang et al. |
| 2003/0134433 A1 | 7/2003 | Gabriel et al. |
| 2003/0135971 A1 | 7/2003 | Liberman et al. |
| 2003/0156992 A1 | 8/2003 | Anderson et al. |
| 2003/0186522 A1 | 10/2003 | Duan et al. |
| 2003/0186544 A1 | 10/2003 | Matsui et al. |
| 2003/0189202 A1 | 10/2003 | Li et al. |
| 2003/0197456 A1 | 10/2003 | Den et al. |
| 2003/0200521 A1 | 10/2003 | DeHon et al. |
| 2004/0005723 A1 | 1/2004 | Empedocles et al. |
| 2004/0026684 A1 | 2/2004 | Empedocles |
| 2004/0067530 A1 | 4/2004 | Gruner |
| 2004/0075464 A1 | 4/2004 | Samuelson et al. |
| 2004/0095658 A1 | 5/2004 | Buretea et al. |
| 2004/0106203 A1 | 6/2004 | Stasiak et al. |
| 2004/0110163 A1 | 6/2004 | Kotlyar et al. |
| 2004/0112964 A1 | 6/2004 | Empedocles et al. |

(56) References Cited

U.S. PATENT DOCUMENTS

| | | |
|---|---|---|
| 2004/0113138 A1 | 6/2004 | DeHon et al. |
| 2004/0113139 A1 | 6/2004 | DeHon et al. |
| 2004/0118448 A1 | 6/2004 | Scher et al. |
| 2004/0133118 A1 | 7/2004 | Llinas |
| 2004/0136866 A1 | 7/2004 | Pontis et al. |
| 2004/0146560 A1 | 7/2004 | Whiteford et al. |
| 2004/0157414 A1 | 8/2004 | Gole et al. |
| 2004/0188721 A1 | 9/2004 | Lieber et al. |
| 2004/0191517 A1 | 9/2004 | Drake |
| 2004/0213307 A1 | 10/2004 | Lieber et al. |
| 2004/0235016 A1 | 11/2004 | Hamers et al. |
| 2004/0262636 A1 | 12/2004 | Yang et al. |
| 2005/0037374 A1 | 2/2005 | Melker et al. |
| 2005/0064185 A1 | 3/2005 | Buretea et al. |
| 2005/0064731 A1 | 3/2005 | Park et al. |
| 2005/0066883 A1 | 3/2005 | Dubrow et al. |
| 2005/0072213 A1 | 4/2005 | Besnard et al. |
| 2005/0079533 A1 | 4/2005 | Samuelson et al. |
| 2005/0079659 A1 | 4/2005 | Duan et al. |
| 2005/0084881 A1 | 4/2005 | Kelley et al. |
| 2005/0084887 A1 | 4/2005 | Samuelson et al. |
| 2005/0100960 A1 | 5/2005 | Dai et al. |
| 2005/0101026 A1 | 5/2005 | Sailor et al. |
| 2005/0106713 A1 | 5/2005 | Phan et al. |
| 2005/0109989 A1 | 5/2005 | Whiteford et al. |
| 2005/0110064 A1 | 5/2005 | Duan et al. |
| 2005/0117441 A1 | 6/2005 | Lieber et al. |
| 2005/0133254 A1 | 6/2005 | Tsakalakos |
| 2005/0147990 A1 | 7/2005 | Samuelson et al. |
| 2005/0147991 A1 | 7/2005 | Samuelson et al. |
| 2005/0161662 A1 | 7/2005 | Majumdar et al. |
| 2005/0181587 A1 | 8/2005 | Duan et al. |
| 2005/0201149 A1 | 9/2005 | Duan et al. |
| 2005/0202615 A1 | 9/2005 | Duan et al. |
| 2005/0212079 A1 | 9/2005 | Stumbo et al. |
| 2005/0214967 A1 | 9/2005 | Scher et al. |
| 2005/0219788 A1 | 10/2005 | Chow et al. |
| 2005/0224778 A1 | 10/2005 | Dubin et al. |
| 2005/0230356 A1 | 10/2005 | Empedocles et al. |
| 2005/0244863 A1 | 11/2005 | Mir |
| 2005/0253137 A1 | 11/2005 | Whang et al. |
| 2005/0257821 A1 | 11/2005 | Ramanathan et al. |
| 2005/0266662 A1 | 12/2005 | Yi |
| 2005/0275010 A1 | 12/2005 | Chen et al. |
| 2005/0287717 A1 | 12/2005 | Heald et al. |
| 2006/0008942 A1 | 1/2006 | Romano et al. |
| 2006/0009003 A1 | 1/2006 | Romano et al. |
| 2006/0019472 A1 | 1/2006 | Pan et al. |
| 2006/0054936 A1 | 3/2006 | Lieber et al. |
| 2006/0057360 A1 | 3/2006 | Samuelson et al. |
| 2006/0160246 A1 | 7/2006 | Massey et al. |
| 2006/0175601 A1 | 8/2006 | Lieber et al. |
| 2006/0237749 A1 | 10/2006 | Lieber et al. |
| 2006/0269927 A1 | 11/2006 | Lieber et al. |
| 2007/0026645 A1 | 2/2007 | Lieber et al. |
| 2007/0032023 A1 | 2/2007 | Lieber et al. |
| 2007/0032051 A1 | 2/2007 | Lieber et al. |
| 2007/0032052 A1 | 2/2007 | Lieber et al. |
| 2007/0048492 A1 | 3/2007 | Lieber et al. |
| 2007/0111493 A1 | 5/2007 | Lee et al. |
| 2007/0158766 A1 | 7/2007 | Lieber et al. |
| 2007/0252136 A1 | 11/2007 | Lieber et al. |
| 2007/0281156 A1 | 12/2007 | Lieber et al. |
| 2008/0161876 A1 | 7/2008 | Wirbisky et al. |
| 2008/0191196 A1 | 8/2008 | Lu et al. |
| 2008/0211040 A1 | 9/2008 | Lieber et al. |
| 2008/0254291 A1 | 10/2008 | Lieber et al. |
| 2009/0004852 A1 | 1/2009 | Lieber et al. |
| 2009/0057650 A1 | 3/2009 | Lieber et al. |
| 2009/0299213 A1 | 12/2009 | Patolsky et al. |
| 2010/0022012 A1 | 1/2010 | Lieber et al. |
| 2010/0087013 A1 | 4/2010 | Lieber et al. |
| 2010/0152057 A1 | 6/2010 | Lieber et al. |
| 2010/0227382 A1 | 9/2010 | Lieber et al. |
| 2011/0042641 A1 | 2/2011 | Lieber et al. |
| 2011/0230747 A1 | 9/2011 | Rogers et al. |
| 2011/0315962 A1 | 12/2011 | Lieber et al. |
| 2012/0068156 A1 | 3/2012 | Koley |
| 2014/0080139 A1 | 3/2014 | Lieber et al. |
| 2014/0184196 A1 | 7/2014 | Lieber et al. |
| 2015/0137794 A1 | 5/2015 | Lieber et al. |

FOREIGN PATENT DOCUMENTS

| | | |
|---|---|---|
| EP | 1087413 A2 | 3/2001 |
| EP | 1170799 A2 | 1/2002 |
| JP | 63128246 A | 5/1988 |
| JP | 07-326603 | 12/1995 |
| JP | 09-191104 | 7/1997 |
| JP | 10-167893 | 6/1998 |
| JP | 11-11917 A2 | 1/1999 |
| JP | 2000-31462 | 1/2000 |
| JP | 2000-55874 A | 2/2000 |
| JP | 2001-281965 | 10/2001 |
| WO | WO 91/06036 A1 | 5/1991 |
| WO | WO 95/02709 A2 | 1/1995 |
| WO | WO 96/28538 A1 | 9/1996 |
| WO | WO 96/29629 A2 | 9/1996 |
| WO | WO 97/32571 A1 | 3/1997 |
| WO | WO 97/34140 A1 | 3/1997 |
| WO | WO 97/33737 A1 | 9/1997 |
| WO | WO 97/34025 A1 | 9/1997 |
| WO | WO 98/39250 A1 | 9/1998 |
| WO | WO 98/48456 A1 | 10/1998 |
| WO | WO 99/24823 A1 | 5/1999 |
| WO | WO 98/42620 A1 | 10/1999 |
| WO | WO 99/63347 A2 | 12/1999 |
| WO | WO 00/09443 A1 | 2/2000 |
| WO | WO 00/17101 A1 | 3/2000 |
| WO | WO 00/19494 A1 | 4/2000 |
| WO | WO 00/29617 A3 | 5/2000 |
| WO | WO 00/51186 A1 | 8/2000 |
| WO | WO 01/03208 A1 | 1/2001 |
| WO | WO 01/44796 A1 | 6/2001 |
| WO | WO 02/17362 A2 | 2/2002 |
| WO | WO 02/31183 A1 | 4/2002 |
| WO | WO 02/48701 A2 | 6/2002 |
| WO | WO 02/080280 A1 | 10/2002 |
| WO | WO 02/086480 A1 | 10/2002 |
| WO | WO 03/005450 A2 | 1/2003 |
| WO | WO 03/016901 A1 | 2/2003 |
| WO | WO 03/053851 A2 | 7/2003 |
| WO | WO 03/054931 A1 | 7/2003 |
| WO | WO 03/063208 A2 | 7/2003 |
| WO | WO 2004/003535 | 1/2004 |
| WO | WO 2004/010552 A1 | 1/2004 |
| WO | WO 2004/032190 A2 | 4/2004 |
| WO | WO 2004/032193 A2 | 4/2004 |
| WO | WO 2004/034025 A2 | 4/2004 |
| WO | WO 2004/038767 A2 | 5/2004 |
| WO | WO 2004/096699 A1 | 11/2004 |
| WO | WO 2004/109282 A1 | 12/2004 |
| WO | WO 2005/059506 A2 | 6/2005 |
| WO | WO 2005/089165 | 9/2005 |
| WO | WO 2005/093831 A1 | 10/2005 |
| WO | WO 2005/094440 | 10/2005 |
| WO | WO 2005/114282 A2 | 12/2005 |
| WO | WO 2005/119753 A2 | 12/2005 |
| WO | WO 2006/107312 A1 | 10/2006 |
| WO | WO 2006/132659 A2 | 12/2006 |
| WO | WO 2007/044034 | 4/2007 |
| WO | WO 2007/145701 A2 | 12/2007 |
| WO | WO 2008/027078 A2 | 3/2008 |
| WO | WO 2008/033303 A2 | 3/2008 |
| WO | WO 2008/123869 A2 | 10/2008 |
| WO | WO 2008/127314 A1 | 10/2008 |
| WO | WO 2009104056 A1 * | 8/2009 |
| WO | WO 2012/170630 A2 | 12/2012 |
| WO | WO 2013/166259 A1 | 11/2013 |

(56) References Cited

FOREIGN PATENT DOCUMENTS

| WO | WO 2014/031709 A1 | 2/2014 |
|---|---|---|
| WO | WO 2014/043341 A1 | 3/2014 |

OTHER PUBLICATIONS

European Office Action for Application No. EP 07873479.5 mailed Sep. 25, 2009.
European Office Action from European Patent Application EP 07873479.5 dated Apr. 7, 2010.
International Search Report and Written Opinion from International Application No. PCT/US2007/024126 mailed Oct. 2, 2008.
International Preliminary Report on Patentability from International Application No. PCT/US2007/024126 mailed Mar. 11, 2009.
Invitation to Pay Additional Fees from International Application No. PCT/US2010/050199 mailed Nov. 26, 2010.
International Search Report and Written Opinion from International Application No. PCT/US2010/050199 mailed Feb. 7, 2011.
International Preliminary Report on Patentability from International Application No. PCT/US2010/050199 issued Mar. 27, 2012.
International Search Report and Written Opinion from International Application No. PCT/US2012/041253 mailed Dec. 26, 2012.
Invitation to Pay Additional Fees from International Application No. PCT/US2013/039228 mailed Jun. 25, 2013.
International Search Report and Written Opinion from International Application No. PCT/US2013/039228 mailed Aug. 30, 2013.
International Search Report and Written Opinion from International Application No. PCT/US2013/055910 mailed Nov. 14, 2013.
Office Action from U.S. Appl. No. 12/225,142 dated Nov. 3, 2011.
Office Action from U.S. Appl. No. 12/225,142 dated Apr. 12, 2012.
Office Action from U.S. Appl. No. 12/225,142 dated Sep. 19, 2012.
Office Action from U.S. Appl. No. 12/225,142 dated May 24, 2013.
Office Action from U.S. Appl. No. 12/225,142 dated Oct. 22, 2013.
Restriction Requirement from U.S. Appl. No. 12/308,207 dated Oct. 19, 2012.
Office Action from U.S. Appl. No. 12/308,207 dated Apr. 5, 2013.
Office Action from U.S. Appl. No. 12/308,207 dated Oct. 21, 2013.
Office Action from U.S. Appl. No. 11/501,466 dated Feb. 5, 2009.
Office Action from U.S. Appl. No. 11/501,466 dated Mar. 30, 2010.
Office Action from U.S. Appl. No. 12/312,740 dated Sep. 6, 2012.
Office Action from U.S. Appl. No. 12/312,740 dated Mar. 7, 2013.
[No Author Listed] DIG Reagents and Kits for Non-Radioactive Nucleic Acid Labeling and Detection: TeloTAGGG Telomere Length Assay. Roche Applied Science. <http://www.roche-applied-science.com/DIG/dig_prod_telomere_length.thm> Last accessed Apr. 5, 2005. 3 pages.
Agarwal, R., et al., "Lasing in Single Cadmium Sulfide Nanowire Optical Cavities," Nano Letters, vol. 5, No. 5, pp. 917-920 (Mar. 29, 2005).
Balavoine et al., Helical crystalization of proteins on carbon nanotube: A first step towards the development of new biosensors. Angew Chem Int Ed. 1999;38(13/14):1912-5.
Blackledge et al., Catalytic Activity of Silanols on Carbamate-Functionalized Surface Assemblies: Monoalkoxy versus Trialkoxy Silanes. Langmuir. Sep. 1999;15(23):8119-25.
Bozovic et al., Electronic properties of mechanically induced kinks in single-walled carbon nanotubes. Applied Physics Letters. Jun. 4, 2001;78(23):3693-5.
Bradley et al., "Integration of Cell Membranes and Nanotube Transistors," Nano Letters (2005) 5, 841-845.
Chen et al., "Large on-off ratios and negative differential resistance in a molecular electronic device", Science, Nov. 19, 1999, 286:1550-51.
Chen, R.J., et al., "Noncovalent functionalization of carbon nanotubes for highly specific electronic biosensors," PNAS, vol. 100, No. 9, pp. 4984-4989 (Apr. 29, 2003).
Cheung et al., "Diameter Controlled Synthesis of Carbon Nanotubes," J. Phys. Chem B, Feb. 16, 2002, 106:2429-2433.
Choe, Modulated Nanowire Structures for Exploring New Nanoprocessor Architechtures and Approaches to Biosensing. Harvard Univertiy thesis. Cambrdige, MA. Apr. 2013. 146 pages.
Choi, K.J., et al., "Enhancement of Ferroelectricity in Strained BaTiO Thin Films," Science, vol. 306, pp. 1005-1009 (Nov. 5, 2004).
Cohen-Karni et al., Graphene and nanowire transistors for cellular interfaces and electrical recording. Nano Lett. Mar. 10, 2010;10(3):1098-102.
Collier et al., "Electronically configurable molecular-based logic gates," Science, Jul. 16, 1999, 285:391-394.
Cui et al., "Diameter-controlled synthesis of single-crystal silicon nanowires," Appl. Phys. Letters, Apr. 9, 2001, 78(15): 2214-2216.
Cui et al., "Doping and Electrical Transport in Silicon Nanowires," J. Phys. Chem B., May 11, 2000, 104(22):5214-5216.
Cui et al., "Functional nanoscale electronic devices assembled using silicon nanowire building blocks", Science, Feb. 2, 2001, 291:851-853.
Cui et al., "High performance silicon nanowire field effect transistors", NANO Letters, 3:2 (2003) pp. 149-152.
Cui et al., "Nanowire nanosensors for highly sensitive and selective detection of biological and chemical species", Science, Aug. 17, 2001, 293:1289-1292.
De Asis et al., High spatial resolution single multiwalled carbon nanotube electrode for stimulation, recording, and whole cell voltage clamping of electrically active cells. Applied Physics Letters. Oct. 13, 2009;95:153701.
Defrancesco, Telomere without end, amen: Looking into longevity with telomere detection kits. The Scientist: Technology Profile. Mar. 30, 1998. <http://www.the-scientist.com/?articles.view/articleNo/18869/title/Telomere-Without-End--Amen--Looking-Into-Longevity-with-Telomere-Detection-Kits/> Last accessed Apr. 5, 2005. 10 pages.
Deng et al., Salicidation process using NiSi and its device application. J Appl Phys. Jun. 15, 1997;81(12):8047-51.
Duan et al., "General Synthesis of Compound Semiconductor Nanowires," Adv. Mat., Feb. 23, 2000, 12(4):298-302.
Duan et al., "High-performance thin-film transistors using semiconductor nanowires and nanoribbons," Nature, Sep. 18, 2003, 425:274-278.
Duan et al., "Laser-Assisted Catalytic Growth of Single Crystal GaN Nanowires," J.Am.Chem.Soc., Dec. 18, 1999, 122:188-189.
Duan et al., "Nonvolatile Memory and Programmable Logic from Molecule-Gated Nanowires," Nano Letters, Apr. 3, 2002, 2(5):487-490.
Duan et al., Intracellular recordings of action potentials by an extracellular nanoscale field-effect transistor. Nat Nanotechnol. Dec. 18, 2011;7(3):174-9. Supporting Information included.
Duan et al.., "Indium phosphide nanowires as building blocks for nanoscale electronic and optoelectronic devices," Nature, Jan. 4, 2001, 409:66-69.
Duan, X., et al., "Single-nanowire elecrtrically driven lasers," Nature, vol. 421, pp. 241-245(Jan. 16, 2003).
Duan, X., et al., "Synthesis and optical properties of gallium arsenide nanowires," Applied Physics Letters, vol. 76, No. 9, pp. 1116-1118 (Feb. 28, 2000).
Esfarjani et al., "Electronic and transport properties of N-P doped nanotubes," Applied Physics Letters, Jan. 4, 1999, 74:79-81.
Fagan et al., Ab initio calculations for a hypothetical material: Silicon nanotubes. Physical Review B. 2000;61(15):9994-6.
Friedman, R.S., et al., "High-speed integrated nanowire circuits," Nature, vol. 434, pp. 1085 (Apr. 28, 2005).
Fromherz, "Electrical interfacing of nerve cells and semiconductor chips" Chemphyschem—A European Journal of Chemical Physics & Physical Chemistry, Wiley VCH, Weinheim, DE, vol. 3, No. 3, Mar. 12, 2002 pp. 276-284, XP002300227.
Fromherz, "Semiconductor chips with ion channels, nerve cells and brain" Physica E—Low-Dimensional Systems and Nanostructures, Elsevier Science BV, NL, vol. 16, No. 1, Jan. 2003, pp. 24-34, XP002300226.
Gabay et al., "Engineered self-organization of neural networks using carbon nanotube clusters," Physica A (2005) 350,611-621.
Gao et al., Outside looking in: nanotube transistor intracellular sensors. Nano Lett. Jun. 13, 2012;12(6):3329-33. Epub May 22, 2012.
Givargizov, "Fundamental aspects of VSL growth", Journal of Crystal Growth, Dec. 1975, 31:20-30.

(56) References Cited

OTHER PUBLICATIONS

Gradecak, S., et al., "GaN nanowire lasers with low lasing thresholds," Applied Physics Letters, vol. 87, pp. 173111 (Oct. 18, 2005).
Gudiksen et al., "Diameter-Selective Synthesis of Semiconductor Nanowires," J.Am.Chem.Soc., Aug. 22, 2000, 122, 8801-8802.
Gudiksen et al., "Growth of nanowire superlattice structures for nanoscale photonics and electronics", Nature, Feb. 7, 2002, 415:617-620.
Gudiksen et al., "Size-Dependent Photoluminescence from Single Indium Phosphide Nanowires," J. Phys. Chem., Mar. 30, 2002, 106:4036-4039.
Gudiksen et al., "Synthetic Control of the Diameter and Length of Single Crystal Semiconductor Nanowires," J. Phys. Chem., Apr. 18, 2001, 105:4062-4064.
Guo et al., "A Silicon Single-Electron Transistor Memory Operating at Room Temperature," Science, 275:649-651 (Jan. 31, 1997).
Guo et al., "Nanoscale silicon field effect transistors fabricated using implant lithography," Appl. Phys. Lett., 71(13):1881-1883 (Sep. 29, 1997).
Hahm et al., "Direct Ultrasensitive Electrical Detection of DNA and DNA Sequence Variations Using Nanowire Nanosensors," Nano Letters. vol. 4, No. 1, pp. 51-54 (Dec. 9, 2003).
Haraguchi et al., "GaAs p-n junction formed in quantum wire crystals," App. Phys. Letters, Feb. 10, 1992, 60(6):745-747.
Haraguchi et al., "Polarization dependence of light emitted from GaAs p-n junctions in quantum wire crystals", Journal of Applied Physics, Apr. 15, 1994, 75(8): 4220-4225.
He et al., Synthesis and characterization of phospholipid-modified multiwalled carbon nanotubes. Materials Research Bulletin. 2008;43(1):141-8.
Heath, J. R., et al., "A liquid solution synthesis of single crystal germanium quantum wires," Chemical Physics Letters, vol. 208, No. 3, 4, pp. 263-268 (Jun. 11, 1993).
Hiruma et al., "Self-organized growth of GaAs/InAs heterostructure nanocylinders by organometallic vasor phase epitaxy", Journal of Crystal Growth, Jun. 1, 1996, 163(3): 226-231.
Hiruma, et al., "GaAs fr e-standing quantum-siz wires," J. Appl. Phys., vol. 74, No. 5, pp. 3162 (Sep. 1, 1993).
Holmes et al., "Control of Thickness and Orientation of Solution-Grown Silicon Nanowires," Science, Feb. 25, 2000, 287:1471-1473.
Hsu et al., MFMOX ferroelectric memory transistor. Non-Volatile Memory Technology Symposium. Oralando, FL. Nov. 15-17, 2004. pp. 24-27.
Hu et al., "Chemistry and Physics in One Dimension: Synthesis and Properties of Nanowires and Nanotubes," Acc. Chem. Res., Feb. 20, 1999, 32(5):435-445.
Hu et al., "Controlled growth and electrical properties of heterojunctions of carbon nanotubes and silicon nanowires," Nature, May 6, 1999, 399:48-51.
Hu et al., "Serpentine Superlattice Nanowire-Array Lasers," IEEE J. Quantum Elec., Aug. 1995, 31(8):1380-1388.
Huang et al., "Directed assembly of one-dimensional nanostructures into functional networks", Science, Jan. 26, 2001, 291: 630-633.
Huang et al., "Gallium Nitride Nanowire Nanodevices," Nano Letters, Jan. 11, 2002, 2(2):101-104.
Huang et al., "Logic Gates and Computation from Assembled Nanowire Building Blocks," Science, Nov. 9, 2001, 294:1313-1317.
Huang et al., "Room-Temperature Ultraviolet Nanowire Nanolasers," Science, Jun. 8, 2001, 292:897-1898.
Hyun et al., Orientation specific synthesis of kinked silicon nanowires grown by the vapour-liquid-solid mechanism. Nanotechnology. Mar. 25, 2009;20(12):125606. Epub Mar. 4, 2009. 5 pages.
IBM News, "IBM creates highest performing nanotube transistors" http://www.ibm.com/news/us/2002/05/20.html. Last accessed Dec. 12, 2005. 1 page.
James et al., "Extracellular Recordings From Patterned Neuronal Networks Using Planar Microelectrode Arrays," IEEE Trans. Biomed. Eng. (2004) 51, 1640-1648.
Javey, A., et al., "Ballistic carbon nanotube field-effect transistors," Nature, vol. 424, pp. 654 (Aug. 7, 2003).
Jensen et al., Kinetics for hybridization of peptide nucleic acids (PNA) with DNA and RNA studied with the BIAcore technique. Biochemistry. Apr. 22, 1997;36(16):5072-7.
Jiang et al., Rational growth of branched nanowire heterostructures with synthetically encoded properties and function. Proc Natl Acad Sci U S A. Jul. 26, 2011;108(30):12212-6. Epub Jul. 5, 2011. Supporting Information included.
Jin et al., "Scalable Interconnection and Integration of Nanowire Devices without Registration," Nano Letters, Apr. 10, 2004, 4(5):915-919.
Johnson et al., "Single gallium nitride nanowire lasers," Nature, Oct. 2002, 1: 106-110.
Johnson et al., "Single Nanowire Lasers," J. Phys. Chem B., Oct. 23, 2001, 105(46):11387-11390.
Joselevich et al., "Vectorial Growth of Metallic and Semiconducting Single-Wall Carbon Nanotubes," Nano Letters, Aug. 30, 2002, 2(10):1137-1141.
Kanjanachuchai et al., "Coulomb blockade in strained-Si nanowires on leaky virtual substrates", Semiconductor Science and Technology, Feb. 2001, 16(2):72-76.
Kong et al., "Chemical vapor deposition of methane for single-walled carbon nanotubes," Chem. Physics Letters, Aug. 14, 1998, 292:567-574.
Kong et al., "Synthesis of individual single-walled carbon nanotubes on patterned silicon wafers," Nature, Oct. 29, 1998, 395:878-881.
Kong et al., Nanotube molecular wires as chemical sensors. Science. Jan. 28, 2000;287:622-5.
Lahoun et al., "Epitaxial core-shell and core-multishell nanowire heterostructures", Nature, Nov. 7, 2002, 420: 57-61.
Lahoun et al., "Semiconductor nanowire heterostructures," Phil. Trans. R. Soc. Lond. A, Apr. 2004, 362:1247-1260.
Law, M., et al., "Nanoribbon Waveguides for Subwavelength Photonics Integration," Science, vol. 305, pp. 1269-1274 (Aug. 27, 2004).
Lee et al., Antibody-based bio-nanotube membranes for enantiomeric drug separations. Science. Jun. 21, 2002;296(5576):2198-200.
Leff, D.V., et al., "Thermodynamic Control of Gold Nanocrystal Size: Experiment and Theory," J. Phys. Chem., vol. 99, pp. 7036-7041 (May 1995).
Lei, B., et al., "Nanowire transistors with ferroelectric gate dielectrics: Enhanced performance and memory effects," Applied Physics Letters, vol. 84, No. 22, pp. 4553-4555 (May 31, 2004).
Li et al., "Molecular detection based on conductance quantization of nanowires" Appl Phys Letter, Mar. 6, 2000, 76(10): 1333-1335.
Li et al., Fabrication of stable metallic nanowires with quantized conductance. Nanotechnology. 1999;10:221-3.
Li et al., Sequence-Specific Label-Free DNA Sensors Based on Silicon Nanowires. Nano Letters. Jan. 2004;4(2):245-7.
Lieber, "Nanoscale Science and Technology: Building a Big Future from Small Things," MRS Bulletin, Jul. 2003, 486-491.
Lieber, C., "Nanowire Superlattices," Nano Letters, vol. 2, No. 2, pp. 81-82 (Jan. 25, 2002).
Lieber, Nanowires: Building blocks for the assembly of integrated nanosystems. Electron Devices Meeting. pp. 21.1.1-21.1.4 (Dec. 13-15, 2004).
Lovat et al., "Carbon Nanotube Substrates Boost Neuronal Electrical Signaling," Nano Letters (2005) 5, 1107-1110.
Lu, W., et al., "One dimensional hole gas in germanium/silicon nanowire heterostructures," PNAS, vol. 102, No. 29, pp. 10046-10051 (Jul. 19, 2005).
MacBeath et al., Printing proteins as microarrays for high-throughput function determination. Science. Sep. 8, 2000;289:1760-3.
Martel, et al., "Single- and multi-wall carbon nanotube field-effect transistors," Appl. Phys. Lett., Oct. 26, 1998, 73(17):2447-2449.
Martens et al., Measurement of telomere length in haematopoietic cells using in situ hybridization techniques. Biochem Soc Trans. Feb. 2000;28(2):245-50.
McAlpine et al., "High-Performance Nanowire Electronics and Photonics and Nanoscale Patterning on Flexible Plastic Substrates," Proc. of the IEEE, Jul. 2005, 93(7):1357-1363.

(56) References Cited

OTHER PUBLICATIONS

McAlpine et al., "Nanoimprint Lithogrphy for Hybrid Plastic Electronics," Nano Letters, Mar. 7, 2003, 3(4):443-445.
McAlpine, et al., "High-Performance Nanowire Electronics and Photonics on Glass and Plastic Substrates," Nano-Letters, Oct. 14, 2003, 3(11):1531-1535.
Menon, V.P., et al., "Fabrication and Evaluation of Nanoelectrode Ensembles," Anal. Chem., vol. 67, pp. 1920-1928 (Jul. 1, 1995).
Merz et al., "Silicon Chip Interfaced with a Geometrically Defined Net of Snail Neurons," Adv Funct Mater (2005) 15, 739-744.
Mitchell et al., Smart nanotubes for bioseparations and biocatalysis. J Am Chem Soc. Sep. 13, 2002;124:11864-5.
Mizutani, T., et al., "Fabrication and characterization of carbon nanotube FETs," Proceedings of SPIE, vol. 5732, pp. 28-36 (Mar. 25, 2005).
Morales et al., "A Laser Ablation Method for the Synthesis of Crystalline Semiconductor Nanowires," Science, Jan. 9, 1998, 279: 208-211.
Musin, R.N., et al., "Structural and electronic properties of epitaxial core-shell nanowire heterostructures," Physical Review B, vol. 71, pp. 155318-1155381-4 (Apr. 20, 2005).
Nakamura et al., Simple, rapid, quantitative, and sensitive detection of telomere repeats in cell lysate by a hybridization protection assay. Clin Chem. Oct. 1999;45(10):1718-24.
Neuman DeVegvar et al., Microarray profiling of antiviral antibodies for development of diagnostics, vaccines, and therapeutics. Clin Immun. Mar. 2004;111:196-201.
Nosho, Y., et al., "n-type carbon nanotube field-effect transistors fabricated by using Ca contact electrodes," Applied Physics Letters, 86(7), pp. 073105 (Feb. 7, 2005).
Offenhausser et al., "Field-Effect transistor array for monitoring electrical activity from mammalian neurons in culture," Biosensors & Bioelectronics (1997) 12, 819-826.
Padeste et al., "Modular amperometric immunosensor devices", 8th International Conference on Solid-State Sensors an Actuators and Eurosensors, Jun. 25-29, 1995, 487-490.
Patolsky et al. "Detection, stimulation, and inhibition of neuronal signals with high-density nanowire transistor arrays" Science, vol. 313, Jun. 25, 2006, pp. 1100-1105, XP002474456.
Patolsky et al., Nanowire sensors for medicine and the life sciences. Nanomedicine (Lond). Jun. 2006;1(1):51-65.
Patolsky et al., Nanowire-based biosensors. Analytical Chemistry. Jul. 1, 2006:4260-9.
Patolsky, F., et al., "Electrical detection of single viruses," PNAS, vol. 101, No. 39, pp. 14017-14022 (Sep. 28, 2004).
Patolsky, F., et al., "Nanowire Nanosensors," Materials Today, pp. 20-28 (Apr. 2005).
Pavesi, L., et al., "Optical gain in silicon nanocrystals," Nature, vol. 408, pp. 440-444 (Nov. 23, 2000).
Qi, P., et al., "Toward Large Arrays of Multiplex Functionalized Carbon Notube Sensors for Highly Sensitive and Selective Molecular Detection," Nano Letters, vol. 3, No. 3, pp. 347-351 (Feb. 6, 2003).
Qing et al., "Nanowire transistor arrays for mapping neural circuits in acute brain slices," PNAS, vol. 107, No. 5, pp. 1882-1887 (Feb. 2, 2010).
Rueckes et al., "Carbon Nanotube-Based Nonvolatile Random Access Memory for Molecular Computing," Science, Jul. 7, 2000, 289,:94-97.
Smalley, Biochip spots single viruses. The Latest Technology Research News. Oct. 20, 2004. <http://www.trnmag.com/Stories/2004/102004/Biochip_spots_single_viruses_102004.html> Last accessed Jan. 13, 2009. p. 1-4.
Soh et al., Integrated nanotube circuits: Controlled growth and ohmic contacting of single walled carbon nanotubes. Appl Phys Lett. Aug. 2, 1999;75(5):627-9.
Solange et al., "Ab initio calculations for a hypothetical material: Silicon nanotubes" Phys Rev B, Apr. 15, 2000, 61(15): 9994-9996.
Star et al., "Preparation and properties of polymer-wrapped single-walled carbon nanotubes", Angew. Chem. Int. May 3, 2001;40(9):1721-25.

Takayama et al., "Patterning cells and their environments using multiple laminar fluid flows in capillary networks", Proc. Natl. Acad. Sci., May 1999, 96:5545-5548.
Tang et al., Si nanowires synthesized by laser ablation of mized SiC and SiO2 powders. Chemical Physics Letters. Nov. 26, 1999;314:16-20.
Tans et al., "Room-temperature transistor based on a single carbon nanotube," Nature. May 7, 1998;393:49-52.
Thess et al., "Crystalline Ropes of Metallic Carbon Nanotubes," Science, Jul. 26, 1996, 273:483-487.
Tian et al., Three-dimensional, flexible nanoscale field-effect transistors as localized bioprobes. Science. Aug. 13, 2010;329(5993):830-4. Supporting Online Material inlcuded.
Tiefenauer et al., "Towards Amperometric Immunosensor Devices", Biosensors and Bioelectronics, 1997, 12(3):213-23.
Timko et al., "Electronic interface between nanowires and neurons," MRS Abstract.
Tong, L., et al., "Subwavelength-diameter silica wires for low-loss optical wave guiding," Nature, vol. 426, No. 18, pp. 816-819 (Dec. 2003).
Urban, J. J., et al., "Single-Crystalline Barium Titanate Nanowires," Adv. Mater., vol. 15, No. 5, pp. 423-426 (Mar. 4, 2003).
Voelker et al., "Signal Transmission from Individual Mammalian Nerve Cell to Field-Effect Transistor," Small (2005) 1, 206-210.
Vossmeyer, T., et al., "Combinatorial approaches toward patterning nanocrystals," J. Applied Physics, vol. 84, No. 7, pp. 3664-3670 (Oct. 1, 1998).
Wang et al., "Highly polarized photoluminescence and photodetection from single indium phosphide nanowires", Science. Aug. 24, 2001;293:1455-7.
Wang et al., "SiO2-enhanced synthesis of Si nanowires by laser ablation," App. Physics Letters. Dec. 28, 1998;73(26):3902-4.
Wang, W. U., et al., "Label-free detection of small-molecule-protein interactions by using nanowire nanosensors," PNAS, vol. 102, No. 9, pp. 3208-3212 (Mar. 1, 2005).
Wei et al., "Synthesis of Single Crystal Bismuth-Telluride and Lead-Telluride Nanowires for New Thermoelectric Materials," Mat. Res. Soc. Symp. Proc., 2000, 581: 219-223.
Whang, D., et al., "Large-Scale Hierarchical Organization of Nanowire Arrays for Integrated Nanysystems," Nano Letters, vol. 3, No. 9, pp. 1255-1259 (Aug. 5, 2003).
Whang, D., et al., "Nanolithography Using Hierarchically Assembled Nanowire Masks," Nano Letters, vol. 3, No. 7, pp. 951-954 (Jun. 19, 2003).
Wolf et al., "Silicon Processing for the VLSI ERA," Lattice Press, 2000, 1:12-13.
Wong et al., "Covalently functionalized nanotubes as nanometre-sized probes in chemistry and biology," Nature. Jul. 2, 1998;394:52-5.
Wu et al., "Block-by-Block Growth of Single-Crystalline Si/SiGe Superlattice Nanowires," Nano Letters. Jan. 19, 2002;2(2): 83-86.
Wu et al., Growth, branching, and kinking of molecular-beam epitaxial <110> GaAs nanowires. Appl Phys Lett, Oct. 20, 2003;83(16):3368-70.
Wu, Y., et al., "Controlled Growth and Structures of Molecular-Scale Silicon Nanowires," Nano Letters, vol. 4, No. 3, pp. 433-436 (Feb. 3, 2004).
Wu, Y., et al., "Single-crystal metallic nanowires and metal/semiconductor nanowire heterostructures," Nature, vol. 430, pp. 61-65 (Jul. 1, 2004).
Xiang, J., et al., "Ge/Si nanowire heterostructures as high-performance field-effect transistors," Nature, vol. 441, No. 25, pp. 489-493 (May 25, 2006).
Xie et al., "Cds/CdSe core/sheath nanostructures obtained from CdSnanowires," Chem. Commun., pp. 1969-1971 (Sep. 3, 1999).
Yamada, "Analysis of submicron carbon nanotube field-effect transistors," Appl. Phys. Letters. Jan. 31, 2000;76:628-30.
Yang et al., "Controlled Growth of ZnO Nanowires and Their Optical Properties," Adv. Funct. Mater. May 2002;12(5):323-31.
Yang, et al., "Wires on water," Nature, vol. 425, pp. 243-244 (Sep. 18, 2003).
Yu et al, "Nanoscale silicon wires synthesized using simple physical evaporation," Appl. Phys. Letters, Jun. 29, 1998, 72:3458-3460.

(56) References Cited

OTHER PUBLICATIONS

Yu et al. "Silicon Nanowires: Preparation, Device Fabrication, and Transport Properties" J. Phys. Chem. B, Nov. 23, 2000, 104, 11864-11870.

Yun et al., "Ferroelectric Properties of Individual Barium Titanate Nanowires Investigated by Scanned Probe Microscopy," Nano Lett, 2:447-450, Feb. 5, 2002.

Zhang et al., "One-dimensional growth mechanism of crystalline silicon nanowires" Journal of Crystal Growth 197 (Feb. 1, 1999) 136-140.

Zheng, G., et al., "Multiplexed electrical detection of cancer markers with nanowire sensor arrays," Nature Biotechnology, vol. 23, No. 10, pp. 1294-1301 (Oct. 2005).

Zheng, G., et al., "Synthesis and Fabrication of High-Performance n-Type Silicon Nanowire Transistors," Adv. Mater., vol. 16, No. 21, pp. 1890-1893 (Nov. 4, 2004).

Zhong et al., "Nanowire Crossbar Arrays as Address Decoders for Integrated Nanosystems," Science. Nov. 21, 2003;302:1377-9.

Zhong, et al., "Coherent Single Charge Transport in Molecular-Scale Silicon Nanowires," Nano Letters, vol. 5, No. 6, pp. 1143-1146 (May 6, 2005).

Zhong, Z., et al., "Synthesis of p-Type Gallium Nitride Nanowires for Electronic and Photonic Nanodevices," Nano Letters. Feb. 20, 2003;3(3):343-6.

Zhou et al., "Growth morphology and micro-structural aspects of Si nanowires synthesized by laser ablation," J. of Crystal Growth. Feb. 1, 1999;197:129-35.

Chung et al., "Silicon nanowire devices," App. Phys. Letters, Apr. 10, 2000, 76(15):2068-2070.

Dunlop et al., High-throughput electrophysiology: an emerging paradigm for ion-channel screening and physiology. Nat Rev Drug Discov. Apr. 2008;7(4):358-68.

Fang et al., Electrical detection of single DNA molecules with silicon nanowire devices. Biophys. J., 551A (2007). Abstract.

Gao et al., Electrostatic potential in a bent piezoelectric nanowire. The fundamental theory of nanogenerator and nanopiezotronics. Nano Letters. Jul. 24, 2007;7(8):2499-505.

Gao et al., Subthreshold regime has the optimal sensitivity for nanowire FET biosensors. Nano Lett. Feb. 10, 2010;10(2):547-52.

Kiss et al., High throughput ion-channel pharmacology: planar-array-based voltage clamp. Assay Drug Dev Technol. Feb. 2003;1(1 Pt 2):127-35.

Patolsky et al., Fabrication of silicon nanowire devices for ultrasensitive, label-free, real-time detection of biological and chemical species. Nat Protoc. 2006;1(4):1711-24.

Schrlau et al., Cell electrophysiology with carbon nanopipettes. ACS Nano. Mar. 24, 2009;3(3):563-8.

Shi et al., Long Si nanowires with millimeter-scale length by modified thermal evaporation from Si powder. Appl Phys. 2005;80:1733-6.

Singhal et al., Multifunctional carbon-nanotube cellular endoscopes. Nat Nanotechnol. Jan. 2011;6(1):57-64. Epub Dec. 12, 2010.

Tian et al., Single-crystalline kinked semiconductor nanowire superstructures. Nat Nanotechnol. Dec. 2009;4(12):824-9. Epub Oct. 18, 2009.

Timko et al., Electrical recording from hearts with flexible nanowire device arrays. Nano Lett. Feb. 2009;9(2):914-8.

Wang et al., Rational growth of branched and hyperbranched nanowire structures. Nano Letters. 2004;4(5):871-4.

Willumsen et al., High throughput electrophysiology: new perspectives for ion channel drug discovery. Receptors Channels. 2003;9(1):3-12.

Wu et al., Germanium/carbon core-sheath nanostructures. App Phys Lett. 2000;77(1):43-5.

Office Action mailed Jul. 15, 2014 for U.S. Appl. No. 12/225,142.

Canadian Office Action dated Oct. 14, 2014 for Application No. 2,655,340.

European Office Action dated Jan. 29, 2015 for Application No. 07873479.5.

International Preliminary Report on Patentability from International Application No. PCT/US2013/039228 mailed Nov. 13, 2014.

International Preliminary Report on Patentability from International Application No. PCT/US2013/055910 mailed Mar. 5, 2015.

Office Action mailed Nov. 25, 2014 for U.S. Appl. No. 12/225,142.

Office Action mailed Feb. 23, 2015 for U.S. Appl. No. 14/030,170.

[No Author Listed] Molecular Wire. Wikipedia®:the Free Encyclopedia. Wikimedia Foundation, Inc. Mar. 11, 2015.

Biercuk et al., Electrical Transport in Single-Wall Carbon Nanotubes. Topics Applied Physics. 2008.111:455-93.

Dekker, Carbon Nanotubes as Molecular Quantum Wires. Physics Today. May 1999. 52(5):22-28. doi: 10.1063/1.882658.

Rotkin, From Quantum Models to Novel Effects to New Applications: Theory of Nanotube Devices. Applied Physics of Carbon Nanotubes NanoScience and Technology 2005, pp. 1-39. DOI: 10.1007/3-540-28075-8_1.

Tans et al., Individual single-wall carbon nanotubes as quantum wires. Nature. Apr. 3, 1997. 386: 474-7. doi:10.1038/386474a0.

\* cited by examiner

BENT NANOWIRES AND RELATED PROBING OF SPECIES

RELATED APPLICATIONS

This application is a national stage filing under 35 U.S.C. §371 of International Patent Application Serial No. PCT/US2010/050199, filed Sep. 24, 2010 entitled "Bent Nanowires and Related Probing of Species," by Tian, et al., which claims the benefit of U.S. Provisional Patent Application Ser. No. 61/245,641, filed Sep. 24, 2009, entitled "Bent Nanowires," by Tian, et al.; and the benefit of U.S. Provisional Patent Application Ser. No. 61/326,108, filed Apr. 20, 2010, entitled "Bent Nanowires and Related Probing of Species," by Tian, et al., Each of these is incorporated herein by reference.

GOVERNMENT FUNDING

This invention was made with government support under Grant No. OD003900 awarded by the National Institutes of Health and under Grant No. 67161 awarded by the MITRE Corporation. The U.S. Government has certain rights in the invention.

FIELD OF INVENTION

The present invention generally relates to nanoscale devices and methods, including bent nanowires and other bent nanoscale objects, and in particular, the ability to probe cells with nanoscale objects.

BACKGROUND

Interest in nanotechnology, in particular sub-microelectronic technologies such as semiconductor quantum dots and nanowires, has been motivated by the challenges of chemistry and physics at the nanoscale, and by the prospect of utilizing these structures in electronic and related devices. While nanoscopic articles might be well-suited for transport of charge carriers and excitons (e.g. electrons, electron pairs, etc.) and thus may be useful as building blocks in nanoscale electronics applications, other than standard small-scale lithographic techniques, nanoelectronics is not a well-developed field. Thus there is a need in the art for new and improved articles and techniques involving nanoelectronics.

SUMMARY OF THE INVENTION

The present invention generally relates to nanoscale devices and methods, including bent nanowires and other bent nanoscale objects, and in particular, the ability to probe cells with nanoscale objects. The subject matter of the present invention involves, in some cases, interrelated products, alternative solutions to a particular problem, and/or a plurality of different uses of one or more systems and/or articles.

According to one aspect, the present invention is generally directed to an article. In one set of embodiments, the article includes a semiconductor nanoscale wire having at least one kink. In some cases, the semiconductor nanoscale wire comprises or consists essentially of a <112> crystallographic orientation and/or a <1120> crystallographic orientation. In certain instances, the semiconductor nanoscale wire consists essentially of one crystallographic orientation.

In accordance with one set of embodiments, the article is directed to a wire having at least one kink. In some embodiments, the wire may consist essentially of a single semiconductor material, for example, CdS, Ge, or Si.

The invention, in another aspect, is directed to a method of growing a semiconductor nanoscale wire. In one set of embodiments, the method includes acts of growing a semiconductor nanoscale wire from a catalyst particle in a first direction by exposing the catalyst particle to a first gaseous reactant, isolating the catalyst particle from the first gaseous reactant, and growing the semiconductor nanoscale wire from the catalyst particle in a second direction by exposing the catalyst particle to a second gaseous reactant, where the second direction is substantially different from the first direction.

In one aspect, an article is provided. The article comprises a nanoscale wire having at least one kink, wherein at least a portion of a surface of the nanoscale wire is amphiphilic.

In another aspect, an article is provided. The article comprises a nanoscale wire having at least one kink, wherein at least a portion of a surface of the nanoscale wire is capable of fusing with a lipid bilayer.

In still another aspect, an article is provided. The article comprises a nanoscale wire having at least one kink, wherein at least a portion of the nanoscale wire is capable of penetrating a lipid bilayer using chemical interactions.

In yet another aspect, a method is provided. The method comprises contacting a cell membrane with a nanoscale object. The method further comprises allowing the cell membrane to fuse with the nanoscale object.

In still another aspect, a method is provided. The method comprises contacting a cell membrane with a nanoscale object. The method further comprises allowing the nanoscale object to penetrate the cell membrane using chemical interactions.

In yet another aspect, a method is provided. The method comprises penetrating a membrane of a cell with a semiconductor nanoscale object. The method further comprises electrically communicating with the cell.

In still another aspect, a method is provided. The method comprises providing a cell. The method further comprises determining an electrical potential inside the cell using field effect.

In yet another aspect, a device is provided. The device comprises a substrate having a plurality of nanoscale objects disposed thereon, wherein at least a portion of a surface of each of the plurality of nanoscale objects is amphiphilic.

In still another aspect, a device is provided. The device comprises a substrate having a plurality of nanoscale objects disposed thereon, wherein at least a portion of a surface of each of the plurality of nanoscale objects is capable of fusing with a lipid bilayer.

In yet another aspect, a device is provided. The device comprises a substrate having a plurality of nanoscale objects disposed thereon, wherein each of the plurality of nanoscale objects is capable of penetrating a lipid bilayer using chemical interactions.

In still another aspect, a method is provided. The method comprises contacting a cell membrane with a device, the device comprising a substrate having a plurality of nanoscale objects disposed thereon. The method further comprises allowing at least some of the plurality of nanoscale objects to fuse with the cell membrane.

In yet another aspect, a method is provided. The method comprises contacting a cell membrane with a device, the device comprising a substrate having a plurality of nanoscale objects disposed thereon, and penetrating the cell membrane with at least some of the plurality of nanoscale objects. The method further comprises determining an electrical potential inside the cell using field effect.

In still another aspect, a method is provided. The method comprises contacting a cell with a drug candidate. The method further comprises measuring an electrical potential inside the cell using field effect.

In another aspect, the present invention is directed to a method of making one or more of the embodiments described herein, for example, bent nanowires and other bent nanoscale objects. In another aspect, the present invention is directed to a method of using one or more of the embodiments described herein, for example, bent nanowires and other bent nanoscale objects.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
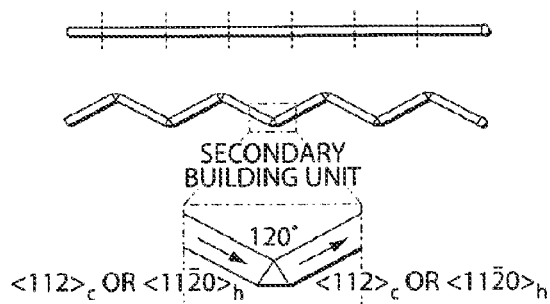
FIGS. 1A-1E illustrate the design and synthesis of nanoscale wires containing kinks, according to one set of embodiments.

The present invention generally relates to nanoscale devices and methods, including bent nanowires and other bent nanoscale objects, and in particular, the ability to probe cells with nanoscale objects. In some aspects, nanoscale objects, including nanowires, are provided that facilitate cell probing, e.g. nanowires that are surface modified such that cells can fuse with the nanowires. Devices including nanoscale objects are provided that allow small or large scale (e.g., multiplexed) probing of cells, and related methods of making such nanoscale objects and devices, and methods of investigating cells, are provided by certain embodiments of the invention. In a related set of embodiments, the present invention is generally related to bent nanowires and other bent nanoscale objects. For instance, in one aspect, the present invention is generally related to a semiconductor nanoscale wire having at least one kink. The semiconductor nanoscale wire may be formed out of any suitable semiconductor, e.g., Si, CdS, Ge, or the like. In some embodiments, a kink in the semiconductor nanoscale wire may be at an angle of about 120° or a multiple thereof. Yet other aspects of the invention are generally directed to methods of using such nanoscale wires, kits involving such nanoscale wires, devices involving such nanoscale wires, or the like.

The present invention generally relates to bent nanowires and other bent nanoscale objects according to certain embodiments. For instance, some embodiments of the invention are directed to a semiconductor nanoscale wire having at least one kink. For example, the wire may have 2, 3, 4, 5, etc. kinks. The semiconductor nanoscale wire may be formed out of any suitable semiconductor, e.g., Si, CdS, Ge, or the like. In some cases, the semiconductor nanoscale wire consists essentially of a single crystallographic orientation, for example, a <112> crystallographic orientation or a <11$\bar{2}$0> crystallographic orientation. In some embodiments, a kink in the semiconductor nanoscale wire may be at an angle of about 120° or a multiple thereof. The kinks may be intentionally positioned along the nanoscale wire in some cases, e.g., using methods such as those described herein. For example, in one aspect, a nanoscale wire may be grown from a catalyst particle by exposing the catalyst particle to various gaseous reactants to cause the formation of one or more kinks within the nanoscale wire.

As mentioned, in some embodiments, the present invention generally relates to nanoscale devices and methods and, in one important aspect, the ability to probe cells with nanoscale objects. Nanoscale objects, including nanowires, are provided that facilitate cell probing, e.g. nanowires that are surface modified such that cells can fuse with the nanowires. Devices including nanoscale objects are provided that allow small or large scale (e.g., multiplexed) probing of cells, and related methods of making such nanoscale objects and devices, and methods of investigating cells, are provided by certain embodiments of the invention.

The following applications are incorporated herein by reference in their entireties: U.S. Provisional Patent Application Ser. No. 61/245,641, filed Sep. 24, 2009, entitled "Bent Nanowires," by Tian, et al.; and U.S. Provisional Patent Application Ser. No. 61/326,108, filed Apr. 20, 2010, entitled "Bent Nanowires and Related Probing of Species," by Tian, et al.

In one aspect, a nanoscale object that can integrate with a lipid bilayer is described. In some embodiments, at least a portion of a surface of the nanoscale object may be modified such that it is capable of fusing with a lipid bilayer. For example, the nanoscale object may include a coating that can interact with a lipid bilayer. In some embodiments, the nanoscale object may be formed out of any suitable semiconductor, e.g., Si, CdS, Ge, or the like. In some cases, a nanowire may have at least one kink. For example, the wire may have 2, 3, 4, 5, etc. kinks. In some embodiments, the nanoscale object may be used to communicate electrically with a cell. For example, the nanoscale object may be used to determine the electrical potential inside a cell. In another aspect, a device including a plurality of nanoscale objects disposed on a substrate is provided. In some embodiments, the device may be used to communicate electrically with a plurality of cells. In some embodiments, the device may be used to communicate electrically with a plurality of (i.e., multiple) regions of a cell. In some cases, electrical communication with a plurality of regions of a cell may occur essentially simultaneously. Yet other aspects of the invention are generally directed to methods of using such nanoscale wires, kits involving such nanoscale wires, devices involving such nanoscale wires, or the like.

In another aspect, a nanoscale device may be constructed that includes a nanoscale wire and/or other nanoscale object. In some embodiments, the nanoscale object may be a semiconductor. Nanoscale objects may, in some embodiments, be bent, i.e., they do not describe a straight line. In some embodiments, the nanoscale object may have at least one kink. As discussed below, there may be any number of kinks present within the nanoscale object, depending on the embodiment, for example, 2, 3, 4, 5, 6, 7, 8, 9, 10, or more kinks. In a semiconductor nanoscale object, the semiconductor may be formed from one, or more than one, semiconductor material, for example, silicon, germanium, cadmium sulfide (CdS), or the like. Further non-limiting examples of semiconductor materials potentially suitable for use in semiconductor nanoscale objects are discussed in detail below. In some embodiments, the nanoscale object may be a nanoscale wire.

In some embodiments, a nanoscale object may be surface-functionalized. In some cases, only a portion of the surface may be functionalized. Surface-functionalization may be achieved, in some embodiments, by coating at least a portion of the nanoscale object (e.g., with a shell). In another embodiment, at least a portion of the nanoscale object may be functionalized by performing a chemical reaction on the surface of the nanoscale object.

In some cases, surface-functionalization comprises attaching a functional moiety to the surface of the nanoscale object. In some embodiments, a functional moiety may be attached directly to the surface of the nanoscale object (i.e., through a chemical bond). In another embodiment, the functional moiety may be attached to a coating on a nanoscale object.

The functional moieties may include simple functional groups, for example, but not limited to, —OH, —CHO, —COOH, —SO$_3$H, —CN, —NH$_2$, —SH, —COSH, COOR, or a halide; biomolecular entities including, but not limited to, amino acids, proteins, sugars, DNA, antibodies, antigens, and enzymes; grafted polymer chains with chain length less than the diameter of the nanoscale wire core, including, but not limited to, polyamide, polyester, polyimide, polyacrylic; a thin coating (e.g., shell), covering the surface of the nanoscale object core, including, but not limited to, the following groups of materials: metals, semiconductors, and insulators, which may be a metallic element, an oxide, a sulfide, a nitride, a selenide, a polymer and a polymer gel. In another embodiment, the invention provides a nanoscale object and a reaction entity with which the analyte interacts, positioned in relation to the nanoscale object such that the analyte can be determined by determining a change in a characteristic of the nanoscale object.

In some embodiments, a nanoscale object may be at least partially coated (e.g., with a shell). In some embodiments, the coating may comprise an amphiphilic material. Non-limiting examples of amphiphilic materials include phospholipids, such as phosphatidate, phosphatidylethanolamine, phosphatidylcholine, phosphatidylserine, phosphatidylinositol, phosphatidylinositol phosphate, phosphatidylinositol bisphosphate, and phosphatidylinositol triphosphate, surfactants, polymers, proteins, and polysaccharides.

In some cases, surface-functionalized nanoscale objects (e.g. nanoscale objects having shells comprising functional moieties) may be coupled to a substrate surface with functional cross-linkers, such as homobifunctional cross-linkers, comprising homobifunctional NHS esters, homobifunctional imidoesters, homobifunctional sulfhydryl-reactive linkers, difluorobenzene derivatives, homobifunctional photoactive linkers, homobifunctional aldehyde, bis-epoxides, homobifunctional hydarzide etc.; heterobifuntional cross-linkers; or trifuntional cross-linkers. In another embodiment, a region may include amorphous oxide, which may allow other molecules to be attached to the surface of the region. This may facilitate attachment or modification, in certain instances.

Nanoscale objects may be surface-functionalized using any suitable method. In some embodiments, a nanoscale object may be cleaned using plasma prior to functionalization. A nanoscale object may be surface-functionalized, in some embodiments, by contacting the nanoscale object with vesicles. For example, the nanoscale object may be placed into a suspension of vesicles, where the vesicles comprise an amphiphilic material such as a phospholipid. Without wishing to be bound by any theory, it is believed that contacting the nanoscale object with vesicles, where the vesicles comprise an amphiphilic material, results in spontaneous formation of a coating of the amphiphilic material on the nanoscale object. In some embodiments, the suspension of vesicles may be formed as follows. An amphiphilic material (e.g., a phospholipid) may be dissolved in a suitable solvent. For example, the amphiphilic material may be dissolved in an organic solvent, such as chloroform. In some cases, the solution of amphiphilic material may be evaporated, for example, under flow of gas (e.g., nitrogen or argon). In some embodiments, the amphiphilic material may be hydrated by adding water or an aqueous solution to the amphiphilic material. In some cases, the aqueous mixture of amphiphilic material may be frozen and thawed one or more times. The aqueous mixture of amphiphilic material may, in some embodiments, be sonicated.

In one aspect, nanoscale objects such as those described herein may be used as biological probes, for example, for the detection of cells, proteins, nucleic acids, carbohydrates, saccharides, lipids, antibodies, or other biological entities. In some embodiments, the nanoscale objects may be used in tissue samples, such as brain slices or cardiac tissues. As an example, in one set of embodiments, nanoscale objects may be attached to electrodes using techniques such as those described herein, e.g., to form a transistor, such as a field effect transistor. In some embodiments, such transistors may be used as probes, e.g., as probes for biological systems. For instance, the transistors may be used to probe cells or tissues, for example, cardiomyocytes or neurons, and/or in contact with three-dimensional tissue sections. For instance, using such nanoscale objects as probes, the nanoscale objects may be used to determine electrical properties of cells or tissues, including in regions below the surface layer of the tissue, due to the shape of the nanoscale objects.

In some embodiments, a nanoscale object may be capable of interacting (e.g., chemically) with a lipid bilayer. For example, a nanoscale object may contact the lipid bilayer and fuse with the lipid bilayer. As used herein, "fuse" means that the nanoscale object integrates into the lipid bilayer such that the lipid bilayer is continuous around one or more portions of the nanoscale object. In some embodiments, the lipid bilayer may rearrange around at least a portion of the nanoscale object. In some embodiments, at least two lipid bilayers may fuse with a nanoscale object. For example, a nanoscale object may fuse with the cell membrane of a cell and with at least one inner membrane of a cell (e.g., a membrane of an organelle).

In some embodiments, integration of a nanoscale object into a lipid bilayer is achieved with mechanical force. For example, a nanoscale object may penetrate a lipid bilayer by being pushed through the lipid bilayer. One of ordinary skill in the art would recognize that such a method requires an input of energy (e.g., applying a force to an object such that the object displaces along a vector). However, in some embodiments, substantially less energy may be required for a surface-functionalized nanoscale object to penetrate a lipid bilayer, i.e., favorable chemical interactions may occur between the nanoscale object and the lipid bilayer. In some embodiments, a surface-functionalized nanoscale object may spontaneously penetrate the lipid bilayer. In some embodiments, the nanoscale object and/or the entity comprising the lipid bilayer may be manipulated such that the nanoscale object and the lipid bilayer are brought into contact. For example, a cell may be manipulated using a micropipette and brought into contact with the nanoscale object. In some cases, the micropipette can be used to affect to the intracellular potential of a cell. For example, the intracellular potential of a cell may be held by a micropipette at between −40 millivolts and −100 millivolts, between −60 millivolts and −90 millivolts, between −50 millivolts and −80 millivolts, or between −40 millivolts and −60 millivolts.

In some cases, the nanoscale object may have an amphiphilic surface (e.g., a surface coated with phospholipid) that can chemically interact with the lipid bilayer. In some embodiments, the amphiphilic surface may decrease the amount of energy needed for the lipid bilayer to rearrange around at least a portion of the nanoscale object (i.e., fuse with nanoscale object).

In some embodiments, when a nanoscale object interacts with a lipid bilayer, a portion of the nanoscale object may extend completely through the lipid bilayer. As a non-limiting example, a nanoscale object may penetrate the cell membrane such that a portion of the nanoscale object is in contact with the cytosol of the cell. In further embodiments, a nanoscale object may penetrate more than one lipid bilayer (i.e., at least two lipid bilayers). For example, a nanoscale object may penetrate the cell membrane of a cell and another membrane inside the cell (e.g., the membrane of an organelle). In some embodiments, a nanoscale object may be in contact with the two or more lipid bilayers. Those of ordinary skill in the art would be able to manipulate a cell and/or a nanoscale object such that the cell and nanoscale object are brought into contact with each other. Advantageously, the nanoscale objects described herein may be fabricated to a size that minimally disrupts a cell membrane.

As discussed in more detail below, a device comprising a plurality of nano scale objects (i.e., at least two nanoscale objects) may be used to penetrate a lipid bilayer at multiple regions. In some embodiments, the plurality of nanoscale objects may penetrate a lipid bilayer essentially simultaneously.

In another aspect, a nanoscale object may be configured with an electrical circuit. For example, in some embodiments, the nanoscale object may be connected to an AC or DC power source. In some embodiments, a device may be fabricated that includes a substrate on which is disposed a plurality of nanoscale objects. A substrate may have disposed thereon at least two nanoscale objects, at least 10 nanoscale objects, at least 100 nanoscale objects, at least 1000 nanoscale objects, or even more. The nanoscale objects may be spaced at any suitable distance from each other. In some embodiments, the nanoscale objects are spaced such that on average a single cell contacts only one nanoscale object at a time. In other embodiments, the nanoscale objects may be spaced such that a plurality of nanoscale objects can be in contact with a cell essentially simultaneously. For example, a cell may be in contact with at least two nanoscale objects, at least 10 nanoscale objects, at least 100 nanoscale objects, at least 1000 nanoscale objects, or even more. In some embodiments, a substrate may be flexible. For example, the substrate may comprise a polymer, such as SU-8. In some embodiments, a flexible substrate may be advantageous since a nanoscale object attached to the flexible substrate may be flexed in response to an external stimulus. For example, a nanoscale object attached to a substrate that rises off the substrate from a first point that is attached to the substrate such that a second point on the nanoscale object is at a first distance from the surface of the substrate (e.g., height) may be flexed to vary the distance between the surface of the substrate and the second point on the nanoscale object. For instance, a glass micropipette can be pressed on and/or retracted from the nanoscale object to vary the distance between the second point on the nanoscale object and the substrate surface. A flexible substrate may be advantageous, for example, when probing a moving cell with the nanoscale object. For example, when probing a beating (i.e., pulsating) cardiomyocyte, the flexible substrate can allow the nanoscale object to flex with the movement of the cell. This property can be advantageous since it can reduce the probability of the nanoscale object breaking. Additionally, this property can reduce the probability of the nanoscale object causing damage to the cell (e.g., tears to the membrane). Examples of systems and methods involving flexible substrates and nanoscale objects can also be seen in U.S. application Ser. No. 10/995,075, filed Nov. 22, 2004, entitled "Nanoscale Arrays, Robust Nanostructures, and Related Devices," by Whang, et al., published as U.S. Pat. Apl. Pub. No. 2005-0253137 on Nov. 17, 2005, incorporated herein by reference.

In some embodiments, a device comprising a plurality of nanoscale objects may be used for multiplex assays. For example, a device can be used to assay a plurality of cells essentially simultaneously. In another example, a device may be used to assay a plurality of regions of a cell essentially simultaneously. Such an assay may be advantageous for determining, for example, how electrical potential inside a cell varies between a first region and a second region.

Nanoscale objects of the invention can be used to probe biological materials, such as cells, using a variety of techniques. U.S. Pat. No. 7,301,199, issued Nov. 27, 2007 to Lieber, et al., and U.S. patent number 7,129,554, issued Oct. 31, 2006 to Lieber, et al., both incorporated herein by reference, describe techniques for making and using nanoscale objects, including arranging nanoscale objects in devices for determination of various species. Some of those techniques can be useful for probing biological species such as cells in accordance with the present invention.

A nanoscale object in contact with a lipid bilayer may be used to communicate electrically, e.g., for determination of some aspect of the lipid bilayer or a related cell. For example, the nanoscale object may be capable of sending and/or receiving an electrical current, and/or passing an electrical current through the nanowire that may be modified for determination. Generally, a cell may be probed by determining a signal or a change in a signal, such as electrical potential or electrical current. The signal amplitude, shape, sign, etc. may all be detected individually or together. In some embodiments, the signal corresponding to a first property (i.e., electrical potential or electrical current) may be correlated with a second property. For example, the electrical potential detected by the nanoscale object may be correlated with pH. Thus, in some embodiments, the nanoscale object may be used to detect the pH within a cell. In some embodiments, the signal detected by the nanoscale object may be recorded.

In some embodiments, the nanoscale object may transmit and/or receive a current greater than 0.1 picoamps, greater than 1 picoamp, greater than 10 picoamps, greater than 100 picoamps, greater than 1 nanoamp, greater than 10 nanoamps, greater than 100 nanoamps, greater than 1 microamp, greater than 10 microamps, greater than 100 microamps, or even more. In some embodiments, the nanoscale object transmit a current between 0.1 picoamps and 100 microamps, between 0.1 picoamps and 100 picoamps, between 10 picoamps and 10 nanoamps, between 1 nanoamp and 1 microamp, or between 100 nanoamps and 100 microamps.

In some cases, the nanoscale object may be capable of detecting an electric potential, e.g., the nanoscale object may be, or include, a field effect transistor (FET). In some embodiments, the nanoscale object may be a two terminal FET device. In some cases, the nanoscale object may detect an electric potential of greater than 0.1 microvolts, greater than 1 microvolt, greater than 10 microvolts, greater than 100 microvolts, greater than 1 millivolt, greater than 10 millivolts, greater than 100 millivolts, greater than 1 volt, or even greater. In some embodiments, the nanoscale object may detect an electric potential between 0.1 microvolts and 1 volt, between 0.1 microvolts and 100 microvolts, between 10 microvolts and 10 millivolts, or between 1 millivolt and 1 volt. In the case of a FET device, the nanoscale object may, in some embodiments, perform as a gate in the transistor. The nanoscale object may allow an increase or decrease in the flow of current between the source and drain of the transistor in response to a threshold electrical potential. The threshold electrical potential may be within any of the voltage ranges listed above. In some embodiments, the nanoscale object can detect the electrical potential intracellularly by being in contact with the cytosol.

In some embodiments, the nanoscale object may used to be communicate electrically with a cell. For example, the nanoscale object may be used to transmit a current to the cell. In some embodiments, the transmitting a current to a cell may induce an action potential.

In some cases, the nanoscale object may be used to determine electrical activity in a cell. Advantageously, the nanoscale object may be used in certain embodiments in place of a patch clamp and/or voltage clamp. In some embodiments, the nanoscale object may be used to determine electric activity in a cell using field effect. Also advantageously, it is believed that the nanoscale objects are less disruptive to cells because of the small size of the nanoscale objects and/or surface functionalization of the nanoscale objects, at least in some cases.

In some embodiments, a nanoscale object may be used to probe a micelle, a liposome, a cell, or any entity having an interface. An interface may be formed, for example, by an amphiphilic material (e.g., a phospholipid or surfactant). In another example, an interface may be formed by oil-water mixture, such as in an emulsion. In some embodiments, the interface in a lipid bilayer. A nanoscale object may be used to probe any type of cell. The cell may be an isolated cell or may be part of a group of cells, such as in a tissue or biofilm. A cell may be a human cell, an animal cell, a non-human mammalian cell, a bacterial cell, a eukaryotic cell, or an archaeal cell. Non-limiting examples of cells include neurons, cardiomyocytes, muscle cells, and pancreatic beta cells.

In another aspect, the devices and methods described herein may be used as a tool for drug discovery. For example, an assay may be set up where cells are treated with one or more candidate drugs (e.g., a library of drug candidates) and the effect of each drug candidate, alone or in combination with another drug candidate and/or known drug (i.e., pharmaceutical agent), on the electrical activity of the cell may be determined.

Figure 8:
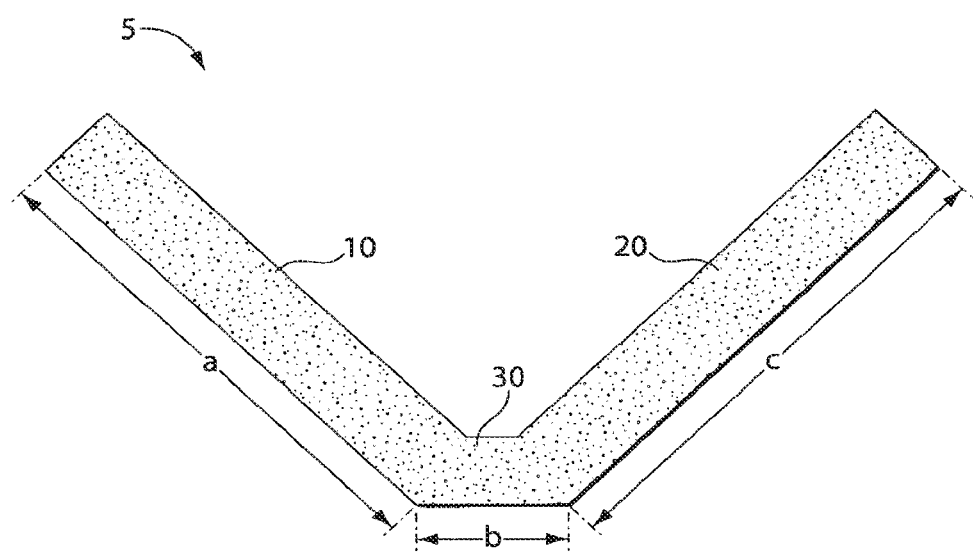
FIG. 8 illustrates a kinked nanoscale, wire, in another embodiment of the invention.

As mentioned, in some embodiments, the nanoscale object (e.g., nanoscale wire) may have at least one "kink." As used herein, a kink is a relatively sharp transition or turning between a first substantially straight portion of a wire and a second substantially straight portion of a wire. The transition may be defined by a transition region linearly defined along the length of the wire, where the region has a maximum linear length that is less than about 5% of the linear length of the average of the first and second substantially straight portion of the regions immediately surrounding the transition region. In some cases, the transition region may have a linear length that is less than about 5%, less than about 3%, less than about 1%, less than about 0.5%, less than about 0.3%, less than about 0.1%, less than about 0.03%, or less than about 0.01% of the linear length of the substantially straight portions surrounding the transition region. As an illustrative example, with reference to FIG. 8, wire 5 includes a first straight portion 10 on the left and a second straight portion 20 on the right of a transition region 30. The linear length of portion 10 is "a," and the linear length of portion 20 is "b." The maximum linear length of portion 30, the transition or "kinked" region, is the longest linear length through this region, given by "c" in FIG. 8.

In some embodiments, a semiconductor nanoscale wire comprises or consists essentially of one crystallographic orientation. For example, the semiconductor nanoscale wire may comprise or consist essentially of a <110>crystallographic orientation, a <112> crystallographic orientation, or a <11$\bar{2}$0> crystallographic orientation. It should be noted that the kinked region need not have the same crystallographic orientation as the rest of the semiconductor nanoscale wire. For instance, the semiconductor nanoscale wire may have a <112> crystallographic orientation while containing one or more kinked regions having a <110> crystallographic orientation. Those of ordinary skill in the art will be able to determine the crystallographic orientation of a nanoscale wire, or portions thereof, using routine techniques such as lattice-resolved TEM images or selected area electron diffraction (SAED) patterns using the nanoscale wire.

In some embodiments, at least some of the kinked regions of a semiconductor nanoscale wires may be at an angle of about 120°. Without wishing to be bound by any theory, the approximately 120° angle may be due to the fact that certain of the semiconductor nanoscale wires may consist essentially of the same crystallographic orientation; due to the packing of atoms along the same crystallographic orientation, only certain kink angles, such as 120° angles, may be allowed in order to ensure that the nanoscale wire exhibits the same crystallographic orientation on both sides of the kink. In addition, as discussed below, in some embodiments, during growth of the nanoscale wire, only certain growth directions may be allowed, and the growth directions are at 120° relative to each other. In addition, in certain embodiments, due to the same crystallographic orientation, the semiconductor nanoscale wire may be substantially planar, i.e., the semiconductor nanoscale wire can be generally contained within a plane, even in embodiments where multiple kinked regions are found in the nanoscale wire. Non-limiting examples of such planar nanoscale wires are shown in FIGS. 1C and 1D. Kinking angles in a semiconductor nanoscale wire may be determined using any suitable technique, e.g., using imaging techniques such as TEM imaging techniques.

Figure 9A:
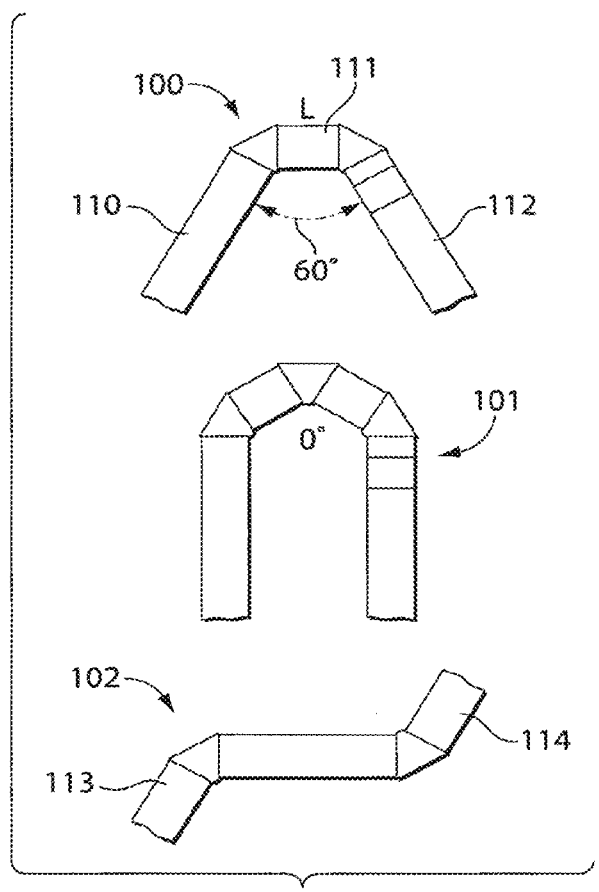
FIG. 9A shows schematics of bent nanoscale objects, according to an embodiment.

In some embodiments, a nanoscale object (e.g., nanoscale wire) may comprise more than one kink, as described above. Referring now to FIG. 9A, 100 depicts nanoscale object having a "cis" conformation, where 110 and 112 are on the same side. Also as shown in FIG. 9A, 102 depicts a nanoscale object having a "trans" conformation, where 113 and 114 are on opposite sides. In some cases, a combination of approximately 120° angle kinks can be used to form nanoscale objects of various shapes. For example, 100 comprises two approximately 120° angle kinks that result in 100 having an approximately 60° angle kink. In another example, 101 comprises three approximately 120° angle kinks that result in 101 having an approximately 0° angle kink. One of ordinary skill in the art will recognize that nanoscale objects with other shapes and angles can be fabricated in other embodiments.

In some cases, at least a portion of a nanoscale wire may be doped, and the nanoscale wire may be doped using techniques such as those known to ordinary skill in the art. Non-limiting examples of such doping techniques are discussed below. In one set of embodiments, different portions of the nanoscale wire may be doped or undoped, and/or different portions of the nanoscale wire may have different dopants, and/or different concentrations of dopants. For instance, in some embodiments, the nanoscale wire may include a first portion having a first doping characteristic, and a second portion having a second doping characteristic. The first portion and the second portion may be separated by one or more kinks within the nanoscale wire. Non-limiting examples of methods of growing such nanoscale wires are discussed below.

Certain aspects of the invention are generally directed to fabricating semiconductor nanoscale wires and other nanoscale objects such as those described herein. Techniques useful for fabricating nanoscale wires include, but are not limited to, vapor phase reactions (e.g., chemical vapor deposition ("CVD") techniques such as metal-catalyzed CVD techniques, catalytic chemical vapor deposition ("C-CVD") techniques, organometallic vapor phase deposition-MOCVD techniques, atomic layer deposition, chemical beam epitaxy, etc.), solution phase reactions (e.g., hydrothermal reactions, solvothermal reactions), physical deposition methods (e.g., thermal evaporation, electron-beam evaporation, laser ablation, molecular beam epitaxy), vapor-liquid-solid ("VLS") growth techniques, laser catalytic growth ("LCG") techniques, surface-controlled chemical reactions, or the like, for instance, as disclosed in Ser. No. 10/196,337, entitled, "Nanoscale Wires and Related Devices," filed Jul. 16, 2002, published as Publication No. 2003/0089899 on May 15, 2003, incorporated herein by reference. The nanoscale wires may be either grown in place or deposited after growth. For instance, the nanoscale wires may be grown on a substrate using techniques such as photolithography, e.g., using sub-micron photolithography, extreme-UV lithography or nanoimprint lithography.

In certain embodiments, a nanoscale wire containing one or more kinks can be grown using certain vapor-liquid-solid ("VLS") growth techniques. For instance, in one set of embodiments, a catalyst particle may be used to grow a first portion of a nanoscale wire, for instance, by exposing the catalyst particle to a first reactant, such as a gaseous reactant. Such a wire may be axially extended in a first direction. Exposure of the catalyst particle to the first reactant may then be stopped, which may stop axial growth of the wire. The catalyst particle can then be perturbed and/or supersaturated to restart growth of the wire. For instance, the catalyst particle may be exposed to exposed to a second reactant (which may be the same or different than the first reactant) and supersaturated and/or nucleated to restart nanoscale wire growth. In some cases, the direction of growth of the nanoscale wire may be altered, for example, by altering the direction of flow of the second reactant, relative to the first reactant.

In some embodiments, the nanoscale wire may be doped during growth of the wire, and in certain cases, the dopant may be changed, e.g., added or removed, and/or the concentration of the dopant may be changed, and/or the dopant may be removed and a second dopant added, etc. Thus, as a non-limiting example, the growing nanoscale wire may be exposed to a first dopant in the first reactant and to a second dopant in the second reactant to create a semiconductor nanoscale wire having a first portion having a first doping characteristic, and a second portion having a second doping characteristic, e.g., as previously described.

This process may also be repeated as many times as desired to grow nanoscale wires having any suitable number of kinks. In addition, the length of each of the substantially straight segments may be controlled, for example, by controlling the length of time the nanoscale wire is exposed to a reactant. In some embodiments, the angle of the kink may be controlled by the crystallographic orientation of the nanoscale wire, e.g., such that an angle of about 120° is created at the kink region, as described above.

As mentioned, certain nanoscale wires may be grown using a vapor-liquid-solid (VLS) mechanism. One feature of the VLS growth process is that equilibrium phase diagrams can be used to select catalysts and growth conditions, and thereby enable rational synthesis of nanoscale wire materials. Semiconductor nanoscale wires of the III-V materials GaAs, GaP, GaAsP, InAs, InP and InAsP, the II-VI materials ZnS, ZnSe, CdS and CdSe, and IV-IV alloys of SiGe can be synthesized in high yield and purity using VLS techniques. Other semiconductors, such as GaAs and CdSe, can also be grown. The nanoscale wires may be prepared as single crystals with dimensions such as those described herein.

Generally, the size of the nanoscale wire is controlled, at least in part, by the size of the catalyst particle used to grow the nanoscale wire. The catalyst particle may be prepared using any suitable technique, for example, using the LCG method, which uses laser ablation to generate nanometer diameter catalytic clusters or particles. This methodology allows the direct formation of adjacent regions having different compositions within a nanoscale wire, such as a p/n junction, and/or adjacent regions differing in concentration of a particular element or composition. In these techniques, a nanoparticle catalyst is used during growth of the nanoscale wire, which may be further subjected to different semiconductor reagents during growth. Alteration of the semiconductor reagents may allow for the formation of abrupt or gradual changes in the composition of the growing semiconductor material, allowing heterostructured materials to be synthesized.

Techniques for doping after growth of the nanoscale wires may also be used, in addition to (or instead of) doping during growth. For example, a nanoscale wire such as those described herein may be first synthesized, then doped post-synthetically with various dopants as discussed herein. For example, a p/n junction can be created by introducing p-type and n-type dopants on a single nanoscale wire. The p/n junction can then be further annealed to allow the dopants to migrate further into the nanoscale wire to form a bulk-doped nanoscale wire.

As mentioned, the nanoscale wire may be doped during growth of the nanoscale wire. Doping the nanoscale wire during growth may result in the property that the doped nanoscale wire is bulk-doped. Furthermore, such doped nanoscale wires may be controllably doped, such that a concentration of a dopant within the doped nanoscale wire can be controlled and therefore reproduced consistently, making possible the commercial production of such nanoscale wires. Additionally, the dopant may be systematically altered during the growth of the nanoscale wire, for example, so that the final nanoscale wire has a first doped region comprising a first dopant and a second doped region differing in composition from the first region, for example, by comprising a second dopant, comprising the first dopant at a different concentration, or omitting the first dopant.

In some embodiments, dopants may be introduced during vapor phase growth of nanoscale wires. For instance, laser vaporization of a composite target composed of a desired material (e. g. silicon or indium phosphide) and/or a catalytic material (e. g. gold) may create a hot, dense vapor. The vapor may condense into liquid nanoclusters through collision with a buffer gas. Growth may begin when the liquid nanoclusters become supersaturated with the desired phase and can continue as long as reactant is available. Growth may terminate when the nanoscale wire passes out of the hot reaction zone or when the temperature is decreased.

Vapor phase semiconductor reactants required for nanoscale wire growth may be produced by laser ablation of solid targets, vapor-phase molecular species, or the like. To create a single junction within a nanoscale wire, the addition of the first reactant may be stopped during growth, and then a second reactant may be introduced for the remainder of the synthesis. Repeated modulation of the reactants during growth may also be used, which may produce nanoscale wire superlattices. Different catalysts suitable for growth may be used, for example, a gold catalyst can be used in a wide-range of III-V and IV materials. Nearly monodisperse metal clusters or particles may be used to control the diameter, and, through growth time, the length various semiconductor nanoscale wires.

As another example, such methods may be used to create nanoscale wires having a multishell configuration. For example, by altering the synthetic conditions during growth, homogeneous reactant decomposition may occur on the surface of the nanoscale wire. Control of the synthetic conditions may lead to a shell forming on the surface of at least a portion of the nanoscale wire, and in some embodiments, the synthetic reaction conditions may be controlled to cause the formation of a thin, uniform shell, a shell having a thickness of one atomic layer, or less in some cases. In other embodiments, by modulating or altering the reactants during growth, more than one shell may be built up on the outer surface of the nanoscale wire. As one example, a silicon nanoscale wire core may be grown, and additional semiconductor materials may be deposited onto at least a portion of the surface, for example, a germanium shell, or a silicon shell doped with a dopant such as boron, or other dopants as described elsewhere in this application. The boundaries between the shells may be atomically abrupt, or may be graduated in some fashion, depending on how reactants such as, for example, silane, germane, or diborane are introduced into the laser catalytic growth system. Arbitrary sequences of Si, Ge, and alloy overlayers on both Si and Ge nanowire cores may also be prepared. Other factors may also contribute to the growing nanoscale wire, such as, for example, the reaction temperature, or the sample position within the furnace. By varying these parameters, the ratio of axial growth to radio growth may be controlled as desired.

Any catalyst able to catalyze the production of nanoscale wires may be used, e.g., as catalyst particles. Gold may be used in certain embodiments. A wide range of other materials may also be contemplated, for example, a transition metal such as silver, copper, zinc, cadmium, iron, nickel, cobalt, and the like. Generally, any metal able to form an alloy with the desired semiconductor material, but does not form a more stable compound than with the elements of the desired semiconductor material may be used as the catalyst.

The buffer gas may be any inert gas, for example, $N_2$ or a noble gas such as argon. In some embodiments, a mixture of $H_2$ and a buffer gas may be used to reduce undesired oxidation by residual oxygen gas.

A reactive gas used during the synthesis of the nanoscale wire may also be introduced when desired, for example, ammonia for semiconductors containing nitrogen, such as gallium nitride. Nanoscale wires may also be flexibly doped by introducing one or more dopants into the composite target, for example, a germanium alloy during n-type doping of InP. The doping concentration may be controlled by controlling the relative amount of doping element, for example, between 0% and about 10% or about 20%, introduced in the composite target.

Laser ablation may also be used to generate liquid nanoclusters that subsequently define the size and/or direct the growth direction of the nanoscale wires. The diameters of the resulting nanoscale wires may be determined by the size of the catalyst cluster or particle, which may be varied by controlling the growth conditions, such as the pressure, the temperature, the flow rate and the like. For example, lower pressure may produce nanoscale wires with smaller diameters in certain cases. Further diameter control may be performed by using uniform diameter catalytic clusters or particles.

If uniform diameter nanoclusters (e.g., less than 10% or less than 20% variation depending on the uniformity of the nanoclusters) are used as the catalytic cluster, nanoscale wires with uniform size (diameter) distribution can be produced in some embodiments, where the diameter of the nanoscale wires is determined by the size of the catalytic clusters. By controlling the growth time or the position of the sample within the reactor, nanoscale wires with different lengths and/or different shell thicknesses may be grown.

Nanoscale wires having uniform diameters or size distributions may be produced in embodiments where the diameter of the nanoscale wire is determined by the size of the catalytic cluster. For example, uniform diameter nanoclusters (for example, having a variation of less than about 10% or less than about 20% in the average diameter) may be used as the starting catalytic clusters.

The diameters of the resulting nanoscale wires may be determined by the size of the catalyst cluster, which in turn may be determined using routine experiments that vary the growth conditions, such as background pressure, temperature, flow rate of reactants, and the like. For example, lower pressure generally produces nanoscale wires with smaller diameters. Further diameter control may be achieved by using uniform diameter catalytic clusters.

The catalytic clusters or the vapor phase reactants may be produced by any suitable technique. For example, laser ablation techniques may be used to generate catalytic clusters or vapor phase reactant that may be used. Other techniques may also be contemplated, such as thermal evaporation techniques.

According to another aspect, semiconductor nanoscale wires such as those described herein can be used in a variety of electronic devices. Techniques for assembling one or more nanoscale wires on a surface, e.g., as part of an electronic device, are known to those of ordinary skill in the art, and include, but are not limited to, electric field alignment, fluid flow, surface regions that selectively attract nanoscale wires, biomolecular recognition, SAMs, microcontact printing, chemically patterned surfaces, or the like. Non-limiting examples of these and other techniques are disclosed in Ser. No. 10/196,337, entitled, "Nanoscale Wires and Related Devices," filed Jul. 16, 2002, published as Publication No. 2003/0089899 on May 15, 2003, incorporated herein by reference in its entirety.

For example, nanoscale wires such as those described herein may be used in a wide variety of devices. Such devices may include electrical devices, optical devices, optronic devices, spintronic devices, mechanical devices or any combination thereof, for example, optoelectronic devices, and electromechanical devices. Functional devices assembled from the nanoscale wires of the present invention may be used to produce various computer or device architectures. Non-limiting examples of these and other devices are disclosed in Ser. No. 10/196,337, entitled, "Nanoscale Wires and Related Devices," filed Jul. 16, 2002, published as Publication No. 2003/0089899 on May 15, 2003, incorporated herein by reference.

The following definitions will aid in the understanding of the invention. However, all definitions as used herein are solely for the purposes of this application. These definitions should not necessarily be imputed to other commonly-owned applications, whether related or unrelated to this application.

Certain devices of the invention may include wires or other components of scale commensurate with nanometer-scale wires, which includes nanotubes and nanowires. In some embodiments, however, the invention comprises articles that may be greater than nanometer size (e. g., micrometer-sized). As used herein, "nanoscopic-scale," "nanoscopic," "nanometer-scale," "nanoscale," the "nano-" prefix (for example, as in "nanostructured"), and the like generally refers to elements or articles having widths or diameters of less than about 1 micrometer, and less than about 100 nm in some cases. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater).

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, for example, ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like.

As used herein, "nanoscopic-scale," "nanoscopic," "nanometer-scale," "nanoscale," the "nano-" prefix, and the like generally refers to elements or articles having widths or diameters of less than about 1 µm, preferably less than about 100 nm in some cases. In all embodiments, specified widths can be smallest width (i.e. a width as specified where, at that location, the article can have a larger width in a different dimension), or largest width (i.e. where, at that location, the article's width is no wider than as specified, but can have a length that is greater).

As used herein, a "wire" generally refers to any material having a conductivity of or of similar magnitude to any semiconductor or any metal, and in some embodiments may be used to connect two electronic components such that they are in electronic communication with each other. For example, the terms "electrically conductive" or a "conductor" or an "electrical conductor" when used with reference to a "conducting" wire or a nanoscale wire, refers to the ability of that wire to pass charge. Typically, an electrically conductive nanoscale wire will have a resistivity comparable to that of metal or semiconductor materials, and in some cases, the electrically conductive nanoscale wire may have lower resistivities, for example, a resistivity lower than about $10^{-3}$ Ohm m, lower than about $10^{-4}$ Ohm m, or lower than about $10^{-6}$ Ohm m or $10^{-7}$ Ohm m.

A "nanoscopic wire" (also known herein as a "nanoscopic-scale wire" or "nanoscale wire") generally is a wire, that at any point along its length, has at least one cross-sectional dimension and, in some embodiments, two orthogonal cross-sectional dimensions less than 1 µm, preferably less than about 500 nm, preferably less than about 200 nm, more preferably less than about 150 nm, still more preferably less than about 100 nm, even more preferably less than about 70, still more preferably less than about 50 nm, even more preferably less than about 20 nm, still more preferably less than about 10 nm, and even less than about 5 nm. In other embodiments, the cross-sectional dimension can be less than 2 nm or 1 nm. In one set of embodiments, the nanoscale wire has at least one cross-sectional dimension ranging from 0.5 nm to 200 nm. In some cases, the nanoscale wire is electrically conductive.

In some embodiments, the nanoscale wire is cylindrical. In other embodiments, however, the nanoscale wire can be faceted, i.e., the nanoscale wire may have a polygonal cross-section. Where nanoscale wires are described having, for example, a core and a shell, the above dimensions generally relate to those of the core. The cross-section of a nanoscopic wire may be of any arbitrary shape, including, but not limited to, circular, square, rectangular, annular, polygonal, or elliptical, and may be a regular or an irregular shape. The nanoscale wire may be solid or hollow.

Any nanoscale wire or other nanoscale object can be used in any of the embodiments described herein, including carbon nanotubes, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscopic-scale dimension, also can be used in some instances, e.g. inorganic structures such as main group and metal atom-based wire-like silicon, transition metal-containing wires, gallium arsenide, gallium nitride, indium phosphide, germanium, cadmium selenide structures. A wide variety of these and other nanoscale wires can be grown on and/or applied to surfaces in patterns useful for electronic devices in a manner similar to technique described herein involving nanoscale wires, without undue experimentation.

The nanoscale objects (e.g., nanoscale wires), in some cases, may be formed having dimensions of at least about 1 micrometer, at least about 3 micrometers, at least about 5 micrometers, or at least about 10 micrometers or about 20 micrometers in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

As used herein, a "nanotube" (e.g. a carbon nanotube) is a nanoscopic wire that is hollow, or that has a hollowed-out core, including those nanotubes known to those of ordinary skill in the art. "Nanotube" is abbreviated herein as "NT." Nanotubes are used as one example of small wires for use in the invention and, in certain embodiments, devices of the invention include wires of scale commensurate with nanotubes.

A "nanowire" (e. g. comprising silicon or another semiconductor material) is a nanoscopic wire that is generally a solid wire, and may be elongated in some cases. Preferably, a nanowire (which is abbreviated herein as "NW") is an elongated semiconductor, i.e., a nanoscale semiconductor. A "non-nanotube nanowire" is any nanowire that is not a nanotube. In one set of embodiments of the invention, a non-nanotube nanowire having an unmodified surface is used in any arrangement of the invention described herein in which a nanowire or nanotube can be used.

Many nanoscopic wires as used in accordance with the present invention are individual nanoscopic wires. As used herein, "individual nanoscopic wire" means a nanoscopic wire free of contact with another nanoscopic wire (but not excluding contact of a type that may be desired between individual nanoscopic wires, e.g., as in a crossbar array). For example, an "individual" or a "free-standing" article may, at some point in its life, not be attached to another article, for example, with another nanoscopic wire, or the free-standing article maybe in solution. This is in contrast to nanotubes produced primarily by laser vaporization techniques that produce materials formed as ropes having diameters of about 2 nm to about 50 nm or more and containing many individual nanotubes (see, for example, Thess, et al., "Crystalline Ropes of Metallic Carbon Nanotubes," *Science*, 273:483-486 (1996)). This is also in contrast to conductive portions of articles which differ from surrounding material only by having been altered chemically or physically, in situ, i.e., where a portion of a uniform article is made different from its surroundings by selective doping, etching, etc. An "individual" or a "free-standing" article is one that can be (but need not be) removed from the location where it is made, as an individual article, and transported to a different location and combined with different components to make a functional device such as those described herein and those that would be contemplated by those of ordinary skill in the art upon reading this disclosure.

As used herein, an "elongated" article (e. g. a semiconductor or a section thereof) is an article for which, at any point along the longitudinal axis of the article, the ratio of the length of the article to the largest width at that point is greater than 2:1. This ratio is termed the "aspect ratio."

In some embodiments, at least a portion of a nanoscopic wire may be a bulk-doped semiconductor. As used herein, a "bulk-doped" article (e.g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles such as carbon nanotubes are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. In particular, in some embodiments, a bulk-doped semiconductor may comprise two or more bulk-doped regions. Thus, as used herein to describe nanoscopic wires, "doped" refers to bulk-doped nanoscopic wires, and, accordingly, a "doped nanoscopic (or nanoscale) wire" is a bulk-doped nanoscopic wire. "Heavily doped" and "lightly doped" are terms the meanings of which are clearly understood by those of ordinary skill in the art. In some cases, one or more regions may comprise a single monolayer of atoms ("delta-doping"). In certain cases, the region may be less than a single monolayer thick (for example, if some of the atoms within the monolayer are absent). As a specific example, the regions may be arranged in a layered structure within the nanoscale wire, and one or more of the regions may be delta-doped or partially delta-doped.

As used herein, a "width" of an article is the distance of a straight line from a point on a perimeter of the article, through the center of the article, to another point on the perimeter of the article. As used herein, a "width" or a "cross-sectional dimension" at a point along a longitudinal axis of an article is the distance along a straight line that passes through the center of a cross-section of the article at that point and connects two points on the perimeter of the cross-section. The "cross-section" at a point along the longitudinal axis of the article is a plane at that point that crosses the article and is orthogonal to the longitudinal axis of the article. The "longitudinal axis" of an article is the axis along the largest dimension of the article. Similarly, a "longitudinal section" of an article is a portion of the article along the longitudinal axis of the article that can have any length greater than zero and less than or equal to the length of the article. Additionally, the "length" of an elongated article is a distance along the longitudinal axis from end to end of the article.

As used herein, a "cylindrical" article is an article having an exterior shaped like a cylinder, but does not define or reflect any properties regarding the interior of the article. In other words, a cylindrical article may have a solid interior or may have a hollowed-out interior. Generally, a cross-section of a cylindrical article appears to be circular or approximately circular, but other cross-sectional shapes are also possible, such as a hexagonal shape. The cross-section may have any arbitrary shape, including, but not limited to, square, rectangular, or elliptical. Regular and irregular shapes are also included.

As used herein, a first article (e. g., a nanoscopic wire or larger-sized structure) "coupled" to a second article is disposed such that the first article either physically contacts the second article or is proximate enough to the second article to influence a property (e. g., an electrical property, an optical property, or a magnetic property) of the second article. The term "electrically coupled" when used with reference to a nanoscopic wire and an analyte or another moiety such as a reaction entity, refers to an association between any of the analyte, other moiety, and the nanoscopic wire such that electrons can move from one to the other, or in which a change in an electrical characteristic of one can be determined by the other. This may include electron flow between these entities, or a change in a state of charge, oxidation state, redox potential, and the like. As examples, electrical coupling can include direct covalent linkage between the analyte or other moiety and the nanoscopic wire, indirect covalent coupling (e.g. via a linking entity), direct or indirect ionic bonding, or other types of bonding (e.g. hydrophobic bonding). In some cases, no actual bonding may be required and the analyte or other moiety may simply be contacted with the nanoscopic wire surface. There also need not necessarily be any contact between the nanoscopic wire and the analyte or other moiety, in embodiments where the nanoscopic wire is sufficiently close to the analyte to permit electron tunneling or other field effects between the analyte and the nanoscopic wire.

As used herein, an "array" of articles (e.g., nanoscopic wires) comprises a plurality of the articles, for example, a series of aligned nanoscale wires, which may or may not be in contact with each other. As used herein, a "crossed array" or a "crossbar array" is an array where at least one of the articles contacts either another of the articles or a signal node (e.g., an electrode).

As used herein, a "semiconductor" is given its ordinary meaning in the art, i.e., an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, phosphorous, or compound semiconductors such as CdS. The semiconductor may be undoped or doped (e.g., p-type or n-type).

As used herein, a "single crystal" item (e.g., a semiconductor) is an item that has covalent bonding, ionic bonding, or a combination thereof throughout the item. Such a single crystal item may include defects in the crystal, but is distinguished from an item that includes one or more crystals, not ionically or covalently bonded, but merely in close proximity to one another.

In some embodiments, the invention may be part of a system constructed and arranged to determine an analyte in a sample to which the nanoscopic wire is exposed. "Determine," and similar terms in this context, means to determine the quantity and/or presence of the an entity such as an analyte in a sample. Determining steps may include, for example, electronic measurements, piezoelectric measurements, electrochemical measurements, electromagnetic measurements, photodetections, mechanical measurements, acoustic measurements, gravimetric measurements and the like. The presence of an analyte can be determined by determining a change in a characteristic in a nanoscopic wire, for example, an electrical characteristic or an optical characteristic, and this change may be detectable. "Determining" may refer to detecting or quantifying interaction between species, e.g., detection of binding between two species.

The term "reaction entity" refers to any entity that can interact with another entity such as analyte (which can be a chemical or biological species, e.g.) in such a manner to cause a detectable change in a property of a nanoscopic wire. The reaction entity may enhance the interaction between the nanoscopic wire and the analyte, or generate a new chemical species that has a higher or lower affinity to the nanoscopic wire, or to enrich the analyte around the nanoscopic wire. The reaction entity can comprise a binding partner to which the analyte binds. The reaction entity, when it comprises a binding partner, can comprise a specific binding partner of the analyte. For example, the reaction entity may be a nucleic acid, an antibody, a sugar, a carbohydrate, or a protein. In other embodiments, the reaction entity may be a polymer, a catalyst, or a quantum dot. A reaction entity that includes a catalyst may catalyze a reaction involving the analyte, resulting in a product that causes a detectable change in the nanoscopic wire, for example, via binding to an auxiliary binding partner of the product electrically coupled to the nanoscopic wire. Another examplary reaction entity is a reactant that reacts with the analyte, producing a product that can cause a detectable change in the nanoscopic wire. The reaction entity may define at least a portion of a shell or a coating on or surrounding at least a part of the nanoscopic wire. As one example, the shell may include a polymer that recognizes molecules in, for example, a gaseous or liquid sample, causing a change in the conductivity of the polymer which, in turn, causes a detectable change in the nanoscopic wire. In some cases, the reaction entity may comprise a nanoparticle, for example, a nanoparticle having binding partners immobilized thereto.

The term "quantum dot" is given its ordinary meaning in the art, and generally refers to semiconductor or metal nanoparticles (for example, a cadmium selenide nanoparticle) that absorb light and re-emit light in a different color. The wavelength of the emitted light may depend on the size of the quantum dot. For example, a 2 nm quantum dot may be able to emit green light, while a 5 nm quantum dot may be able to emit red light.

As used herein, "attached to," in the context of a species relative to another species or to a surface of an article, means that the species is chemically or biochemically linked via covalent attachment, attachment via specific biological binding (e.g., biotin/streptavidin), coordinative bonding such as chelate/metal binding, or the like. For example, "attached" in this context includes multiple chemical linkages, multiple chemical/biological linkages, etc.

The term "binding partner" refers to a chemical or biological species, such as a protein, antigen, antibody, small molecule, etc., that can undergo binding with another entity, e.g. an analyte, or its respective "binding partner." The term includes specific, semi-specific, and non-specific binding partners, as known to those of ordinary skill in the art. As one example, Protein A is usually regarded as a "non-specific" or semi-specific binder. The term "specifically binds," when referring to a binding partner (e.g., a protein, a nucleic acid, an antibody, or the like.), may refer to a reaction that is determinative of the presence and/or identity of one or more other members of the binding pair in a mixture of heterogeneous molecules (e.g., including proteins and other biologics). Thus, for example, in the case of a receptor/ligand binding pair, the ligand would specifically and/or preferentially select its receptor from a complex mixture of molecules, or vice versa. Other examples include an enzyme that would specifically bind to its substrate, a nucleic acid that would specifically bind to its complement, or an antibody that would specifically bind to its antigen. Other examples include nucleic acids that specifically bind or hybridize to their complements, antibodies that specifically bind to their antigens, and the like. The binding may be by one or more of a variety of mechanisms including, but not limited to, ionic interactions, covalent interactions, hydrophobic interactions, van der Waals interactions, or the like.

The term "fluid" generally refers to a substance that tends to flow and to conform to the outline of its container. Typically, fluids are materials that are unable to withstand a static shear stress. When a shear stress is applied to a fluid, it experiences a continuing and permanent distortion. Typical fluids include liquids and gasses, but may also include free flowing solid particles, viscoelastic fluids, and the like.

The term "sample" can be any cell, tissue, or fluid that can be derived from or originates from a biological source (a "biological sample"), or other similar media, biological or non-biological, and that can be evaluated in accordance with the invention, such as a bodily fluid, environmental matter, water, or the like. A sample can include, but is not limited to, a biological sample drawn from an organism (e.g. a human, a non-human mammal, an invertebrate, a plant, a fungus, an algae, a bacteria, a virus, etc.); a sample drawn from food designed for human consumption, a sample including food designed for animal consumption such as livestock feed, milk; an organ donation sample, a sample of blood destined for a blood supply; a sample from a water supply, and the like. One example of a sample is a sample drawn from a human or animal to determine the presence or absence of a specific nucleic acid sequence.

A "sample suspected of containing" a particular component means a sample with respect to which the content of the component is unknown. For example, a fluid sample from a human suspected of having a disease, such as a neurodegenerative disease or a non-neurodegenerative disease, but not known to have the disease, defines a sample suspected of containing neurodegenerative disease. "Sample," in this context, includes naturally-occurring samples, such as physiological samples from humans or other animals, samples from food, livestock feed, and the like. Typical samples taken from humans or other animals include tissue biopsies, cells, whole blood, serum or other blood fractions, urine, ocular fluid, saliva, cerebro-spinal fluid, fluid or other samples from tonsils, lymph nodes, needle biopsies, etc.

The terms "polypeptide," "peptide," and "protein," may be used interchangeably herein to refer to a polymer of amino acid residues. The terms generally apply to amino acid polymers in which one or more amino acid residues is a naturally occurring or artificially created amino acid. The term also includes variants on the traditional peptide linkage joining the amino acids making up the polypeptide, such as an ester linkage.

The terms "nucleic acid," "oligonucleotide," and their grammatical equivalents herein generally refer to at least two nucleotides covalently linked together. A nucleic acid of the present invention is preferably single-stranded or double stranded, and may generally contain phosphodiester bonds, although in some cases, as outlined below, nucleic acid analogs are included that may have alternate backbones, comprising, for example, phosphoramide (Beaucage et al. (1993) *Tetrahedron* 49 (10):1925 and references therein); Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research," Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp. 169-176). Several nucleic acid analogs are described in Rawls, *C & E News* Jun. 2, 1997 page 35. These modifications of the ribose-phosphate backbone may be performed, for example, to facilitate the addition of additional moieties such as labels, or to increase the stability and half-life of such molecules in physiological environments. Similarly, "polynucleotides" or "oligonucleotides" may generally refer to a polymer of nucleotides, which may include natural nucleosides (for example, adenosine, thymidine, guanosine, cytidine, uridine, deoxyadenosine, deoxythymidine, deoxyguanosine and deoxycytidine), nucleoside analogs (for example, 2-aminoadenosine, 2-thiothymidine, inosine, pyrrolopyrimidine, 3-methyladenosine, C5-bromouridine, C5-fluorouridine, C5-iodouridine, C5-propynyluridine, C5-propynylcytidine, C5-methylcytidine, 7-deazaadenosine, 7-deazaguanosine, 8-oxoadenosine, 8-oxoguanosine, O6-methylguanosine or 2-thiocytidine), chemically or biologically modified bases (for example, methylated bases), intercalated bases, modified sugars (2'-fluororibose, arabinose, or hexose), or modified phosphate groups (for example, phosphorothioates or 5'-N-phosphoramidite likages).

As used herein, an "antibody" refers to a protein or glycoprotein consisting of one or more polypeptides substantially encoded by immunoglobulin genes or fragments of immunoglobulin genes. The recognized immunoglobulin genes include, for example, the kappa, lambda, alpha, gamma, delta, epsilon and mu constant region genes, as well as other immunoglobulin variable region genes. Light chains may be classified as either kappa or lambda. Heavy chains may be classified as gamma, mu, alpha, delta, or epsilon, which in turn may define the immunoglobulin classes, for example, IgG, IgM, IgA, IgD and IgE, respectively. A typical immunoglobulin (antibody) structural unit may be a tetramer. Each tetramer may be composed of two identical or similar pairs of polypeptide chains, each pair having one "light" (about 25 kD) and one "heavy" chain (about 50-70 kD). The N-terminus of each chain may define a variable region of about 100 to 110 or more amino acids primarily responsible for antigen recognition. The terms variable light chain (VL) and variable heavy chain (VH) refer to these light and heavy chains, respectively, and are well-known to those of ordinary skill in the art.

Antibodies may exist as intact immunoglobulins or as a number of well characterized fragments produced by digestion with various peptidases. Thus, as one example that would be understood by one of ordinary skill in the art, pepsin may digest an antibody below (i.e. toward the Fc domain) the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region thereby converting the (Fab')2 dimer into an Fab' monomer. The Fab' monomer may be a Fab with part of the hinge region (see, Paul (1993) *Fundamental Immunology*, Raven Press, N.Y. for a more detailed description of other antibody fragments). While various antibody fragments may be defined in terms of the digestion of an intact antibody, one of skill will appreciate that such fragments may be synthesized de novo either chemically, by utilizing recombinant DNA methodology, by "phage display" methods (see, e.g., Vaughan et al. (1996) *Nature Biotechnology*, 14 (3): 309-314, and PCT/US96/10287) or other similar techniques. Antibodies may also include single chain antibodies, e.g., single chain Fv (scFv) antibodies in which a variable heavy and a variable light chain are joined together (directly or through a peptide linker) to form a continuous polypeptide.

As used herein, "plurality" means two or more.

As used herein, a "set" of items may include one or more of such items.

As used herein, the terms "comprising," "including," "carrying," "having," "containing," "involving," and the like are to be understood to be open-ended, i.e., to mean including but not limited to.

The present invention, in many embodiments, includes nanoscopic wires, each of which can be any nanoscopic wire, including nanorods, nanowires, organic and inorganic conductive and semiconducting polymers, nanotubes, semiconductor components or pathways and the like. Other nanoscopic-scale conductive or semiconducting elements that may be used in some instances include, for example, inorganic structures such as Group IV, Group III/Group V, Group II/Group VI elements, transition group elements, or the like, as described below. For example, the nanoscale wires may be made of semiconducting materials such as silicon, indium phosphide, gallium nitride and others. The nanoscale wires may also include, for example, any organic, inorganic molecules that are polarizable or have multiple charge states. For example, nanoscopic-scale structures may include main group and metal atom-based wire-like silicon, transition metal-containing wires, gallium arsenide, gallium nitride, indium phosphide, germanium, or cadmium selenide structures.

The nanoscale wires may include various combinations of materials, including semiconductors and dopants. The following are non-comprehensive examples of materials that may be used as dopants. For example, the dopant may be an elemental semiconductor, for example, silicon, germanium, tin, selenium, tellurium, boron, diamond, or phosphorous. The dopant may also be a solid solution of various elemental semiconductors. Examples include a mixture of boron and carbon, a mixture of boron and $P(BP_6)$, a mixture of boron and silicon, a mixture of silicon and carbon, a mixture of silicon and germanium, a mixture of silicon and tin, or a mixture of germanium and tin.

In some embodiments, the dopant or the semiconductor may include mixtures of Group IV elements, for example, a mixture of silicon and carbon, or a mixture of silicon and germanium. In other embodiments, the dopant or the semiconductor may include a mixture of a Group III and a Group V element, for example, BN, BP, BAs, AN, AlP, AlAs, AlSb, GaN, GaP, GaAs, GaSb, InN, InP, InAs, or InSb. Mixtures of these may also be used, for example, a mixture of BN/BP/BAs, or BN/AlP. In other embodiments, the dopants may include alloys of Group III and Group V elements. For example, the alloys may include a mixture of AlGaN, GaPAs, InPAs, GaInN, AlGaInN, GaInAsP, or the like. In other embodiments, the dopants may also include a mixture of Group II and Group VI semiconductors. For example, the semiconductor may include ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, (ZnCd)Se, or Zn(SSe), or the like. Additionally, alloys of different groups of semiconductors may also be possible, for example, a combination of a Group II-Group VI and a Group III-Group V semiconductor, for example, $(GaAs)_x(ZnS)_{1-x}$. Other examples of dopants may include combinations of Group IV and Group VI elemnts, such as GeS, GeSe, GeTe, SnS, SnSe, SnTe, PbO, PbS, PbSe, or PbTe. Other semiconductor mixtures may include a combination of a Group I and a Group VII, such as CuF, CuCl, CuBr, CuI, AgF, AgCl, AgBr, AgI, or the like. Other dopant compounds may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO$, $(Cu, Ag)(Al, Ga, In, Tl, Fe)(S, Se, Te)_2$ and the like.

For Group IV dopant materials, a p-type dopant may be selected from Group III, and an n-type dopant may be selected from Group V, for example. For silicon semiconductor materials, a p-type dopant may be selected from the group consisting of B, Al and In, and an n-type dopant may be selected from the group consisting of P, As and Sb. For Group III-Group V semiconductor materials, a p-type dopant may be selected from Group II, including Mg, Zn, Cd and Hg, or Group IV, including C and Si. An n-type dopant may be selected from the group consisting of Si, Ge, Sn, S, Se and Te. It will be understood that the invention is not limited to these dopants, but may include other elements, alloys, or materials as well.

Controlled doping of nanoscale wires can be carried out to form, e.g., n-type or p-type semiconductors. One set of embodiments involves use of at least one semiconductor, controllably-doped with a dopant (e.g., boron, aluminum, phosphorous, arsenic, etc.) selected according to whether an n-type or p-type semiconductor is desired. A bulk-doped semiconductor may include various combinations of materials, including other semiconductors and dopants. For instance, the nanoscopic wire may be a semiconductor that is doped with an appropriate dopant to create an n-type or p-type semiconductor, as desired. As one example, silicon may be doped with boron, aluminum, phosphorous, or arsenic. In various embodiments, this invention involves controlled doping of semiconductors selected from among indium phosphide, gallium arsenide, gallium nitride, cadmium selenide. Dopants including, but not limited to, zinc, cadmium, or magnesium can be used to form p-type semiconductors in this set of embodiments, and dopants including, but not limited to, tellurium, sulfur, selenium, or germanium can be used as dopants to form n-type semiconductors from these materials. These materials may define direct band gap semiconductor materials and these and doped silicon are well known to those of ordinary skill in the art. The present invention contemplates use of any doped silicon or direct band gap semiconductor materials for a variety of uses.

Nanotubes that may be used in the present invention include single-walled nanotubes (SWNTs) that exhibit unique electronic, and chemical properties that may be particularly suitable for molecular electronics. Structurally, SWNTs may be formed of a single graphene sheet rolled into a seamless tube with a diameter that may be, for example, on the order of about 0.5 nm to about 5 nm, and a length that can exceed about 10 µm, about 20 µm, or more in some cases. Depending on diameter and helicity, SWNTs may behave as a one-dimensional metal or a semiconductor material, and may also be formed as a mixture of metallic and semiconducting regions. Methods of manufacture of nanotubes, including SWNTs, and characterization are known. Methods of selective functionalization on the ends and/or sides of nanotubes also are known, and the present invention makes use of these capabilities for use in molecular electronics. The basic structural and electronic properties of nanotubes can be used to create connections or input/output signals, and nanotubes have a size consistent with molecular or nanoscopic-scale architecture.

The present invention contemplates, in one aspect, a nanoscale wire, for example, with a smallest width of less than 500 nm, having two or more regions having different compositions. The regions may be positioned radially, as in a core/shell arrangement, or longitudinally from each other. Combinations of these arrangements are also possible. Each regions may have any shape or dimension, as long as at least one of the regions is nanoscopically-sized. For example, the region may have a smallest dimension of less than 1 µm, less than 100 nm, less than 10 nm, or less than 1 nm. In some cases, one or more regions may comprise a single monolayer of atoms ("delta-doping"). In certain cases, the region may be less than a single monolayer thick (for example, if some of the atoms within the monolayer are absent).

As used herein, regions differing in composition may comprise different materials or elements, or may comprise the same materials or elements, but at different ratios or concentrations. Each region may be of any size or shape within the wire, for example, the regions may be adjacently positioned along the longitudinal axis of the nanoscale wire. The junctions may be, for example, a p/n junction, a p/p junction, an n/n junction, a p/i junction (where i refers to an intrinsic semiconductor), an n/i junction, an i/i junction, or the like. The junction may also be a Schottky junction. The junction may also be a semiconductor/semiconductor junction, a semiconductor/metal junction, a semiconductor/insulator junction, a metal/metal junction, a metal/insulator junction, an insulator/insulator junction, or the like. The junction may also be a junction of two materials, a doped semiconductor to a doped or an undoped semiconductor, or a junction between regions having different dopant concentrations. The junction may also be a defected region to a perfect single crystal, an amorphous region to a crystal, a crystal to another crystal, an amorphous region to another amorphous region, a defected region to another defected region, an amorphous region to a defected region, or the like.

More than two regions may be present, and these regions may have unique compositions or may comprise the same compositions. As one example, a wire may have a first region having a first composition, a second region having a second composition, and a third region having a third composition or the same composition as the first composition. Specific non-limiting examples include gallium arsenide/gallium phosphide compositionally modulated superlattices containing from 2 to 21 layers, or n-silicon/p-silicon and n-indium phosphide/p-indium phosphide modulation doped nanoscale wires.

The regions of the nanoscale wire may be distinct from each other with minimal cross-contamination, or the composition of the nanoscale wire may vary gradually from one region to the next. The regions may be both longitudinally arranged relative to each other, or radially arranged (e.g., as in a core/shell arrangement) on the nanoscale wire. As one example, the nanoscale wire may have multiple regions of alternating semiconductor materials arranged longitudinally, each having a segment length of about 500 nm. In another example, a nanoscale wire may have two regions having different compositions arranged longitudinally, surrounded by a third region or more having a composition different from that of the other regions. As a specific example, the regions may be arranged in a layered structure within the nanoscale wire, and one or more of the regions may be delta-doped or partially delta-doped.

In some embodiments, the junction between two differing regions (e.g., between different longitudinal regions of a core or shell, or between a core and shell, or between two different shells) may be "atomically-abrupt," where there is a sharp transition at the atomic scale between two adjacent regions that differ in composition. However, in other embodiments, the junction between two differing regions may be more gradual. For example, the "overlap region" between the adjacent regions may be a few nanometers wide, for example, less than about 10 nm, less than about 20 nm, less than about 40 nm, less than about 50 nm, less than about 100 nm, or less than about 500 nm. In certain embodiments, the overlap region between a first region having a composition and a second region having a composition different from the first region (i.e., different concentrations or different species) can be defined as the distance between where the composition of the overlap region ranges between about 10 vol % and about 90 vol % of the composition of the first region, with the remainder having a complementary amount of the composition of the second region. In certain embodiments of the invention, nanoscale wires having more than one junction between two regions having different compositions are also contemplated. For example, a nanoscale wire may have 2, 3, 4, or more overlap regions. The number of periods and the repeat spacing may be constant or varied during growth.

In some embodiments, a gradual change in composition between two adjacent regions may relieve strain and may enable the defect free junctions and superlattices. However, in other embodiments, atomically-abrupt interfaces may be desirable, for example, in certain photonic and electronic applications. The nature of the interface between the two adjacent regions may be controlled by any suitable method, for example, by using different nanocluster catalysts or varying the growth temperature when reactants are switched during synthesis. Nanoscale wires having atomically abrupt regions may be fabricated, for example, by reducing the diameter of the nanoscale wire, for example, by reducing the size of the starting nanocluster, or by controlling exposure of the growing wire to dopant gases, for example, by selectively purging or evacuating the region surrounding the wire between different gas exposures or reaction conditions. All of these embodiments can be provided with one, or multiple shells. These shells can be of the same or different composition relative to each other, and any of the shells can be of the same composition of a segment of the core, or of a different composition, or can contain the same or different concentration of a dopant as is provided in a section of the core. The shells may be grown using any suitable growth technique, for example, including the techniques described herein, such as CVD or LCG.

In some embodiments, devices make particular use of adjacent regions having different compositions within a nanoscale wire, for example, p-type and n-type semiconductor regions. A p/n junction may be defined by at least one n-type semiconductor and at least one p-type semiconductor positioned adjacent to each other within the nanoscale wire, where at least one portion of each region contacts at least one portion of the other region, and each semiconductor including portions that do not contact the other component.

In various embodiments, the doping of semiconductors in a nanoscale object (e.g., wire) may be controlled and altered. In certain embodiments, the nanoscale wires may be produced using techniques that allow for direct and controlled growth of the nanoscale wires. The direct growth of doped nanoscale wires may eliminate the need to use lithographic steps during production of the nanoscale wire, thus facilitating the "bottom-up" assembly of complex functional structures.

Light-emission sources are provided in which electrons and holes may combine to emit light. One embodiment of a light-emission source includes at least one p/n junction, in particular, a p/n junction within a single, free-standing nanoscale wire. When forward-biased (i.e., positive charge applied to the p-type region and a negative charge applied to the n-type region), electrons flow toward the junction in the n-type region and holes flow toward the junction in the p-type region. At the p/n junction, holes and electrons may combine, emitting light. Other techniques may be used to cause one or more nanoscale wires, or other semiconductors to emit light, as described below in more detail.

At the size scale of the invention (nanoscale) the wavelength of light emission may be controlled by controlling the size of the p/n junction, for example, the overlap region between the p-type region and the n-type region, the diameter of the nanoscale wire or by controlling the size of at least one, and preferably both components in embodiments having configurations involving crossed wires. Where nanowires are used, a nanowire with a larger smallest dimension will provide emission at a lower frequency. For example, in the case of a doped indium phosphide wire, at size scales associated with typical fabrication processes, the material may emit at 920 nm, depending on the dopant. At the size scales of the present invention, the wavelength of emission may be controlled to emit at wavelengths shorter than 920 nm, for example between 920 and 580 nm. Wavelengths can be selected within this range, such as 900, 850, 800, 750, 700 nm, etc., depending upon the wire size.

The nanoscale wires may also exhibit polarization anisotropy in some embodiments. The polarization anisotropy may arise from the large dielectric contrast inherent to the nanoscale wires having two or more regions having different compositions. In contrast, mixing of valence bands due to quantum confinement yields smaller polarization ratios (i.e., less than about 0.60) in single-region nanoscale wires. Thus, polarization-sensitive nanoscale photodetectors may be constructed using the nanoscale wires of the present invention, which may be used in integrated photonic circuits, near-field imaging, or other high-resolution or high-speed detectors.

The conductance (G) of an individual nanoscale wire may increase by about 2 to 3 orders of magnitude with increasing excitation power density in some cases. In some embodiments, polarization-sensitive photodetectors in which an individual nanoscale wire serves as the detection element may be constructed. These photodetectors may have a reproducible photoconductivity with a nearly instantaneous response time (i.e., with a response time of less than about 1 s, preferably less than about 1 ms, more preferably less than about 1 μs, still more preferably less than about 1 ns, and even more preferably less than about 1 ps, and even more preferably still less than about 1 fs. Preferably, the photoconductivity may also exhibit polarization anisotropy, where the parallel excitation is over an order of magnitude larger than the perpendicular excitation. Quantitatively, the photoconductivity anisotropy ratio, $\sigma=(G_{\|}-G_{\perp})/(G_{\|}+G_{195})$, where $G_{\|}$ is the conductance with parallel excitation and $G_{\perp}$ is the conductance with perpendicular excitation, may be between 0.91±0.07, with some nanodetectors exhibiting the theoretical maximum polarization of 0.96 in the case of certain indium phosphide wires. The active device nanoscale wire element of the present invention may also be sensitive to multiple wavelengths of light.

In some embodiment, information-recording devices may be fabricated based on semiconducting nanoscale wires. In certain embodiments, switching memory may be achieved based on the observation that the conductance of these semiconducting nanoscale wires can change significantly upon either a gate or bias voltage pulse when the surface of the nanoscale wires are appropriately modified, for example, with molecules, functional groups, or nanocrystals. Other properties of the nanoscale wire may also be used to record memory, for example, but not limited to, the redox state of the nanoscale wire, mechanical changes, magnetic changes, induction from a nearby field source, and the like.

Specifically, with respect to changes in conductance, subjection to positive or negative gate or bias voltage pulses may cause the change of charge states in the molecules or nanocrystals, and induces the device to make a fully reversible transition between low and high resistance states. The different states may hysterically persist in the set state, even after the voltage source is deactivated. This feature (change in electrical properties upon voltage pulse) may enable the fabrication of electrically erasable and rewritable memory switching devices in which the reversible states are indicated by the conductance of the nanoscale wires. In addition, the memory switching devices may be assembled specifically from nanoscale material building blocks, and may not be created in planar materials by lithography.

The following documents are incorporated herein by reference: U.S. patent application Ser. No. 09/935,776, filed Aug. 22, 2001, entitled "Doped Elongated Semiconductors, Growing Such Semiconductors, Devices Including Such Semiconductors, and Fabricating Such Devices," by Lieber, et al., published as U.S. Patent Application Publication No. 2002/0130311 on Sep. 19, 2002; U.S. patent application Ser. No. 10/196,337, filed Jul. 16, 2002, entitled "Nanoscale Wires and Related Devices," by Lieber, et al., now U.S. Pat. No. 7,301,199, issued Nov. 27, 2007; and U.S. patent application Ser. No. 12/310,764, filed Mar. 6, 2009, entitled "Branched Nanoscale Wires," by Lieber, et al.

The following examples are intended to illustrate certain embodiments of the present invention, but do not exemplify the full scope of the invention.

EXAMPLE 1

This example illustrates rational design and synthesis of 2D multiply-kinked nanowires (FIG. 1A), where kinks are introduced at defined positions during growth. These hierarchical nanowires were built-up from a "secondary building unit" ("SBU") of two straight single-crystalline arms connected by one fixed 120° angle joint (FIG. 1A). Two $<112>_c$ or $<110>_c$ vectors in a cubic crystal structure, or two $<11\text{-}20>_h$ or $<1\text{-}100>_h$ vectors in a hexagonal structure could form the 120° joint when rotating about the $<111>_c$ and $<0001>_h$ zone axes, respectively (FIG. 1A; FIG. 6). FIG. 1A shows a schematic of a coherently kinked nanowire and the secondary building unit (SBU) which contains two arms and one joint. The multiply-kinked nanowires (middle panel) were derived from the corresponding 1D nanowire by introducing the joints at the points indicated by dashed lines (upper panel). The subscript c and h denote cubic and hexagonal structures, respectively.

Figure 1B:
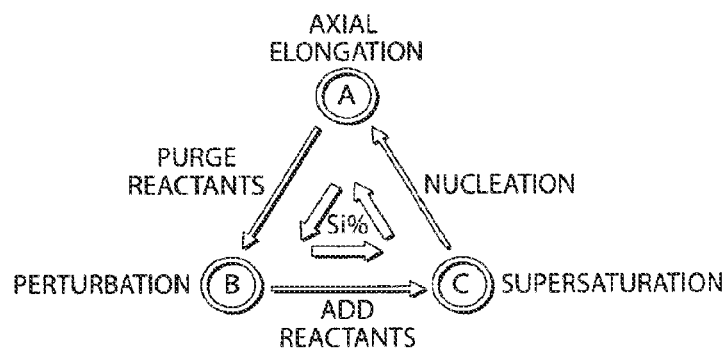
Figure 1C:
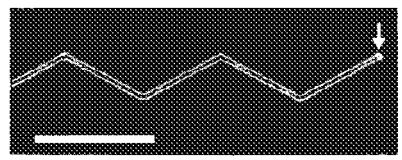
Figure 1D:
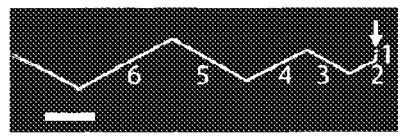

In this example, SBU formation involved three main steps during nanocluster-catalyzed growth (FIG. 1B); (A) axial growth of a 1D nanowire arm segment, (B) purging of gaseous reactants to suspend nanowire elongation, and (C) supersaturation and nucleation of nanowire growth following re-introduction of reactants. The gradient accompanying the innermost arrows indicates the change of silicon concentration in nanocluster catalyst during synthesis of a kinked silicon nanowire. As illustrated for the example case of silicon, the concentration of silicon-reactant dissolved in the nanocluster catalyst dropped during purging and then reached a maximum upon supersaturation. Steps (A)-(C) can also be iterated to link a number of SBUs generating a 2D chain structure (FIG. 1A).

This approach is first illustrated with the synthesis of 2D silicon nanowire chains. Roughly 80 nm diameter silicon nanowires with dominant <112> axial orientation were synthesized by gold nanocluster-catalyzed vapor-liquid-solid (VLS) methods (see below and FIG. 7). Scanning electron microscope (SEM) images of a typical kinked silicon nanowire structure (FIG. 1C, scale bar of 1 micrometer) produced by several iterations of the cycle discussed above, designed to yield equal-length segments, illustrate several features, as follows. The arrow highlights the position of the nanocluster catalyst. Well-defined 2D kinked nanowire structures were observed with nearly equal arm lengths, which were consistent with the constant segment growth times, and uniform diameters. Visible gold catalyst was visible at the nanowire tips (FIGS. 1C and 1D), and appeared to show uniform diameters, indicating that growth proceeded via the nanocluster-catalyzed VLS process during synthesis. FIG. 1D is an SEM image of a multiply-kinked silicon nanowire with decreasing arm segment lengths; scale bar is 1 micometer. The growth durations were 30, 60, 90, 120, 150, and 180 s for segments 1 to 6, respectively. The arrow highlights the position of the nanocluster catalyst. In addition, the joint angle appeared to be 120° and all SBUs appeared to be confined in a single 2D plane (FIG. 1A). Also, the yield of such a kinked 2D chain structure was higher than 40% for these 80 nm diameter nanowires with purge times of 15 seconds, while the remaining nanowires had a 1D morphology.

Figure 6A:
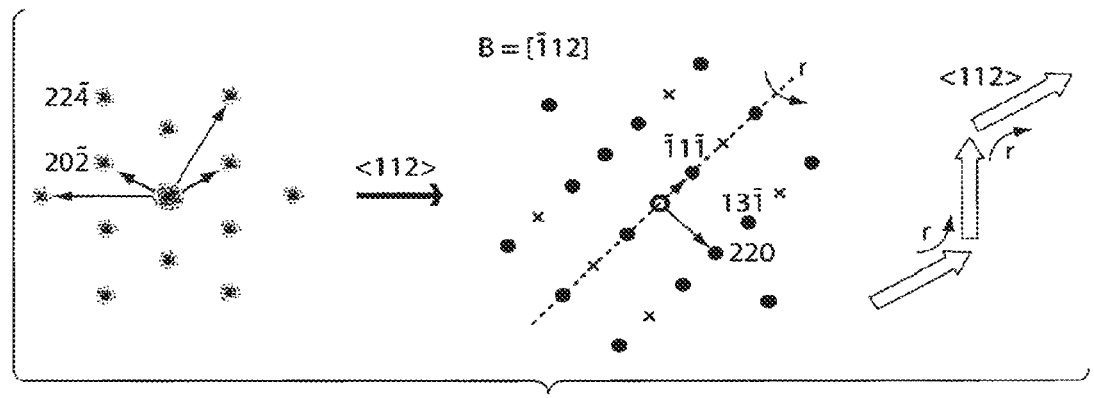
FIGS. 6A-6B illustrate kinked semiconductor nanowire superstructures, in another set of embodiments.

With respect to FIG. 6, FIG. 6A illustrates certain crystallographic parameters for rational synthesis of kinked semiconductor nanowires with cubic crystal structures. The group IV atoms (e.g., silicon and germanium) were arranged in a "diamond structure," while Group III(II) and Group V(VI) atoms adopted the "zinc-blende" or "sphalerite" structural motifs. The left panel in FIG. 6A depicts a schematic electron diffraction (ED) pattern from a cubic single crystal recorded along the [111] zone axis. Light and dark arrows mark a pair of <112> and <110> directions, respectively, with an angle of 120° separating identical directions in the (111) plane. This discussion is focused on nanowires with <112> orientations and those defined by the diamond crystal structure (e.g., silicon and germanium). The schematic [−112] zone ED pattern (middle panel), which corresponds to an ED pattern recorded from the cross section of a <112>-oriented silicon nanowire, identifies a single <111> axis. Inducing rotation about this <111> axis at controlled points in a nanowire would yield a 2D multi-kinked superstructures (right panel). It should also be noted that kink-arm growth was generally coherent, that is with preservation of the original <112> orientation of the silicon nanowire.

Figure 6B:
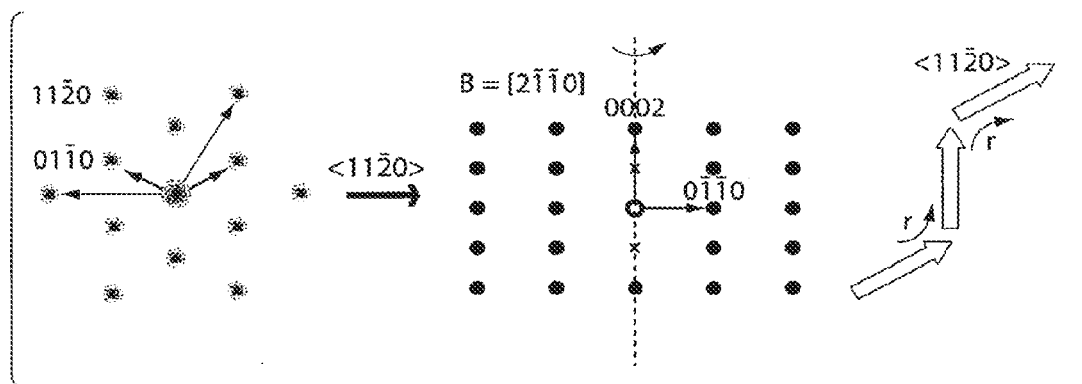

FIG. 6B illustrates certain crystallographic parameters for rational synthesis of kinked semiconductor nanowires with hexagonal crystal structures, for example, the "wurtzite" structures of the II-VI and III-V semiconductors cadmium sulfide and gallium nitride. A schematic ED pattern recorded along the [0001] zone axis (left panel) shows pairs of <11-20> or <1-100> directions with 120° between identical directions in the (0001) plane. Similar to the discussion of FIG. 6A, there was a single <0001> axis in <11-20>-oriented nanowires as visualized in the schematic [2-1-10] zone ED pattern 1 (middle panel). A 2D multi-kinked superstructures of <11-20>-oriented wurtzite nanowires (right panel) was formed by rotating about this <0001> axis. In the ED patterns, the zone axis is denoted as B, and x symbols mark double diffraction spots.

Figure 7:
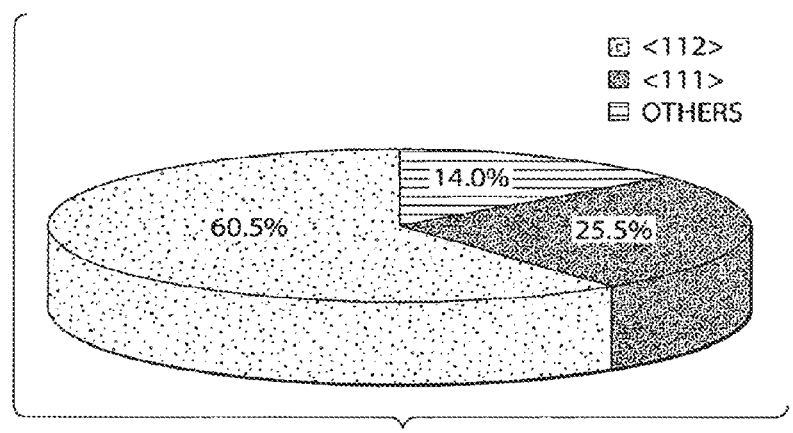
FIG. 7 illustrates growth orientation statistics for kinked nanoscale wires, according to one embodiment of the invention.

FIG. 7 shows growth orientation statistics for silicon nanowires. The silicon nanowires were grown using 80 nm diameter gold nanocluster catalysts at 455-460° C. and 40 torr total pressure. The flow rates of silane, phosphine and hydrogen were 1-2, 2-10 and 60 standard cubic centimeters per minute, respectively. Transmission electron microscopy (TEM) imaging and electron diffractions (ED) were used to identify the nanowire orientations. Under these growth conditions, <112>-oriented nanowires appeared to predominate.

EXAMPLE 2

To illustrate ab initio design and synthesis, in this example, kinked silicon nanowires were prepared in which the arm length was intentionally varied. A representative SEM image of a structure with 6-distinct segment lengths (FIG. 1D) revealed that the formation of well-defined SBU kinks appeared to be independent of the constituent segment lengths within a range of at least 180-2500 nm that were investigated.

Figure 1E:
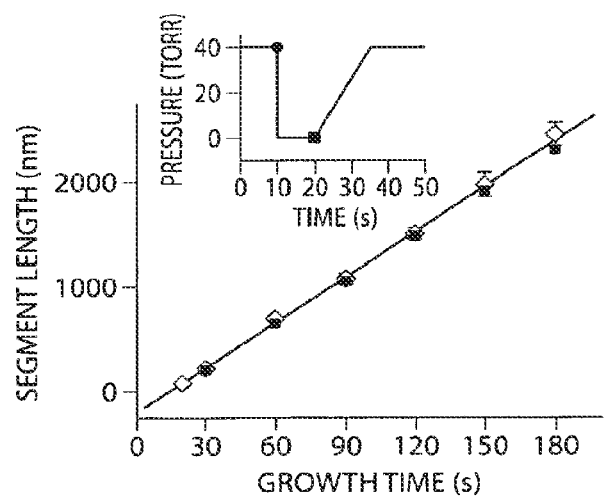

Analysis of the segment lengths in uniformly kinked nanowire samples yielded a linear dependence of segment length on the axial growth time (FIG. 1E), further supporting well controlled VLS growth. In FIG. 1E, each diamond represents average segment length data (error bars: ±1 standard deviation) from a sample containing nanowires with uniform segment lengths between kinks. The line is a linear fit to these data. The solid squares are data points taken from the nanowire shown in FIG. 1D. The inset shows growth pressure variation during kink synthesis. Solid spheres and squares denote the start of purging and re-introduction of reactants, respectively. The slope of the linear fit yielded a nanowire axial growth rate of 870 nm/min under current steady state conditions (FIG. 1E, inset; see also below). The differential segment length data extracted from FIG. 1D was also plotted (squares) and agreed with data acquired from the kinked nanowires with uniform segments, demonstrating control for independent syntheses and, correspondingly, the capability for ab initio design and synthesis. It should also be noted that these results show that segment length was determined by growth time.

EXAMPLE 3

Figure 2A:
FIGS. 2A-2F illustrate various nanoscale wires containing kinks, in certain embodiments of the invention.
Figure 2B:
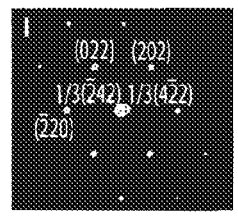
Figure 2C:
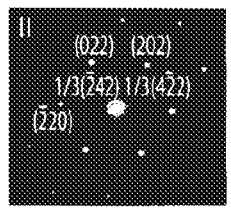

This example shows the atomic level structure of the 2D kinked nanowires using transmission electron microscopy (TEM). A representative TEM image (FIG. 2A) of a multiply-kinked silicon nanowire and selected area electron diffraction (SAED) patterns recorded from nonadjacent joints (FIGS. 2B-2C) showed that this nanostructure was single crystalline and that the arms and joints appeared to be free of bulk dislocations and defects. FIG. 2A is a bright-field TEM image of a multiply-kinked silicon nanowire; scale bar corresponds to 1 micrometer. The region I and region II dashed circles highlight nonadjacent kinks where diffraction data was recorded. The yellow arrow highlights the position of the nanocluster catalyst. FIG. 2B shows selected area electron diffraction (SAED) patterns recorded from regions I and II in FIG. 2A. The SAED patterns were recorded along the <111> zone axis. FIG. 2C is a TEM image of a single kink with crystallographic directions and facets indicated by arrows and dashed lines, respectively; the scale bar is 50 nm. The region I and region II open squares highlight regions of the joint and one arm where high resolution images were recorded.

The SAED patterns from kink positions I and II, which were separated by about 3 micrometers and 2 intervening kinks, could be indexed for the <111> zone axis and showed that the 2D chain structure extended in the {111} plane. This also confirmed that the segments grew along the <112> direction in a coherent manner. These observations were consistent with FIG. 1A.

Figure 2D:
Figure 2E:
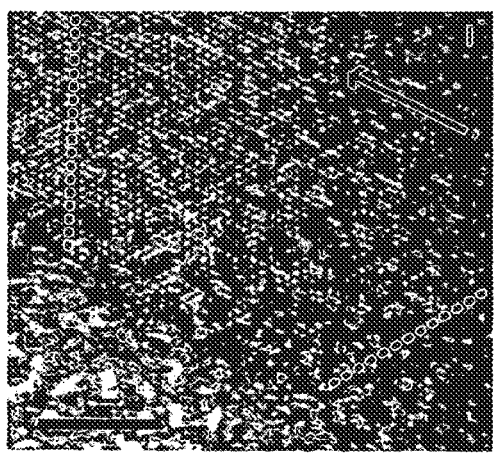
Figure 2F:
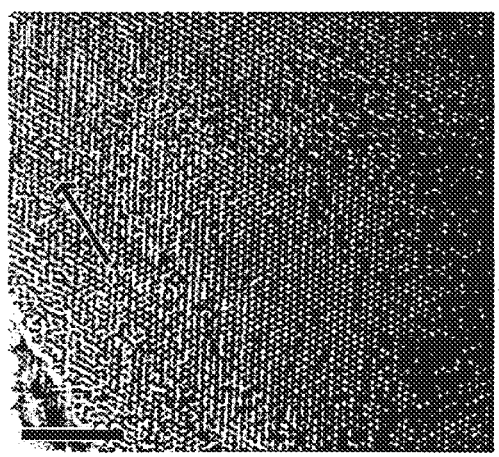

Lattice-resolved TEM images of a single kink from regions I and II in FIG. 2C (FIGS. 2D, 2E, and 2F) further illuminate key SBU features. The scale bars are 5 nm. Dashed lines and arrows denote crystallographic planes and growth directions, respectively. The images demonstrated that there are no atomic-scale twin defects or stacking faults, showing a single crystal structure across the complete arm-joint-arm junction. Furthermore, the SBU reported here preserves crystallographic orientation and composition in arms over multiple kinks. Also, the joint appeared to be a quasi-triangular structure with {111} top/bottom facets and {112} side facets joining the two arms. The outer nanowire edge facet appeared to change during growth of the kink, following $\{110\}_{arm}$ to $\{112\}_{joint}$ to $\{110\}_{arm}$.

EXAMPLE 4

Figure 3A:
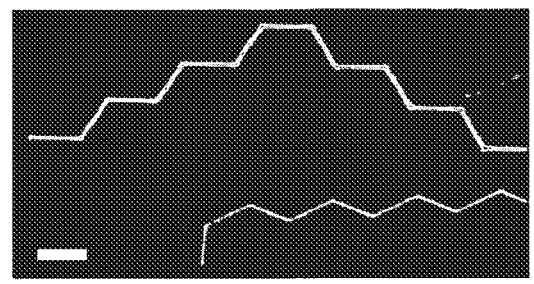
FIGS. 3A-3F illustrate various nanoscale wires containing kinks and growth therof, in another set of embodiments.

In this example, to show the mechanism and limits of the single crystalline kinked junction formation, the kink frequency was characterized as a function of certain parameters, including nanowire diameter and purge time. The kink frequency was defined in this particular example as $P_{kink}=N_k/N_t=N_k/(N_k+N_s)$, where $N_t$, $N_k$ and $N_s$ denoted the number of total designed junctions, observed kink junctions, and observed straight and node-like junctions, respectively. Under optimal growth conditions (see below), both 80 and 150 nm silicon nanowires (FIG. 3A) showed a high probability of kinks with a regular zigzag geometry. FIG. 3A shows SEM images of 150 (upper) and 80 nm (lower) diameter kinked silicon nanowires grown with periodic 15 s purges; scale bar is 1 micrometer.

Figure 3B:
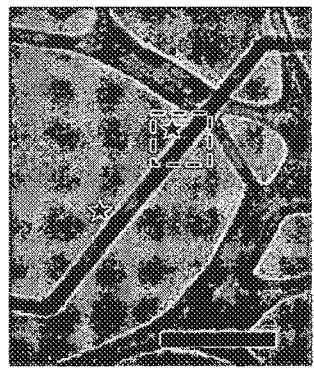
Figure 3C:
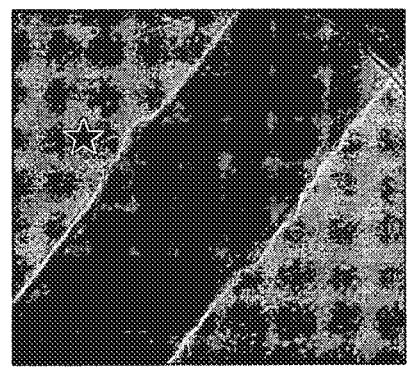

When the purge time of step-B (FIG. 1B) was reduced to 3 s or 1 s, nodes or incipient kinks (FIGS. 3B-3C) were observed at the positions expected for kinks based on elongation time and growth rate. FIGS. 3B and 3C are TEM images at low (FIG. 3B) and high (FIG. 3C) magnification of one 80 nm diameter silicon nanowire segment subjected to a 1 s purge. The stars mark incipient kinks or nodes, and the dashed square corresponds to the region where FIG. 3C was recorded. Scale bars are 500 and 50 nm. Higher resolution SEM or TEM defined the nodes as slightly larger diameter regions with lengths of ~50 nm.

Figure 3D:
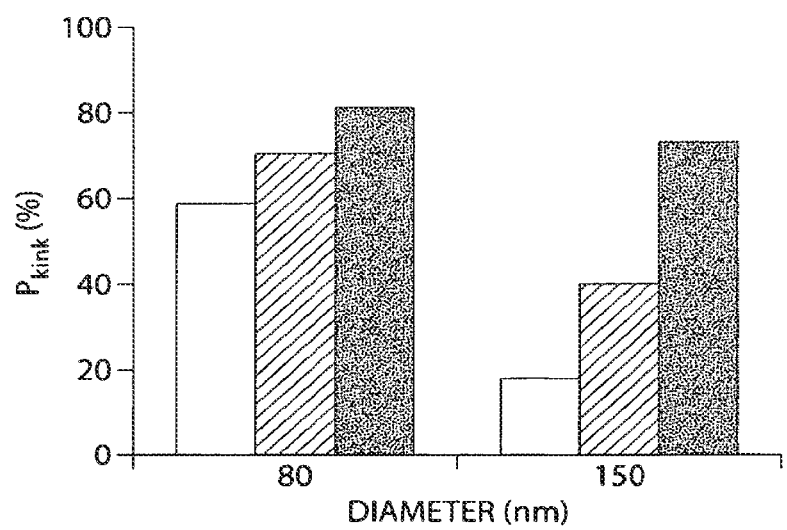

A summary of results for 80 and 150 nm diameters obtained for 1 s, 3 s, and 15 s purges (FIG. 3D) quantifies these observations and shows that this reduced kink frequency with decreasing purge times appeared to be more pronounced in larger diameter nanowire samples. Each of these was averaged over at least 15 multiply-kinked nanowires. These results are consistent with reactant depletion from the nanocluster catalyst being important for kink formation since the relative depletion will be smaller at fixed purge time in larger versus smaller diameter nanowires.

Figure 3E:
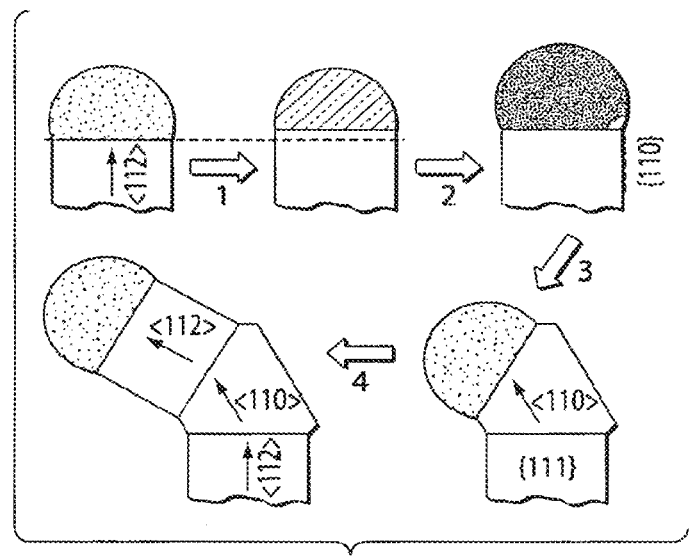

Overall, without wishing to be bound by any theory, the above studies suggest kink formation may potentially be explained by the step-wise model shown in FIG. 3E. Arrows 1-4 denote purge, reintroduction of reactant, joint growth and subsequent arm growth, respectively. In step 1 of this model, reactant is depleted from the catalyst during the purge, and if the concentration is reduced sufficiently, elongation will cease. When reactant is re-introduced in step 2, the catalyst can become supersaturated and undergo heterogeneous nucleation. For short purge times and larger diameter nanowires, the reactant concentration is sufficient for elongation to continue; however, this situation can lead to a flattening of the catalyst nanodroplet and increase in nanowire diameter consistent with formation of nodes (FIG. 3C, marked with stars). In step 3, growth proceeds with preservation of the most stable {111} facets, thus implying that the heterogeneous nucleation should occur preferentially at the active {110} edges of the three phase boundary. This model yields a transition from the <112> to <110> direction about the <111> axis. This growth along <110> is transient since this direction is not thermodynamically favorable in this diameter regime (FIG. 7), and in step 4, the kink is completed with a transition to another <112> direction thus completing a single SBU with coherent arm growth directions. <112> to <111> growth switching was not observed in these kinked structures, possibly because the growth of a <111> segment required the formation of six new {112} facets and the disappearance of two stable {111} facets of the initial <112> segment.

EXAMPLE 5

Figure 3F:
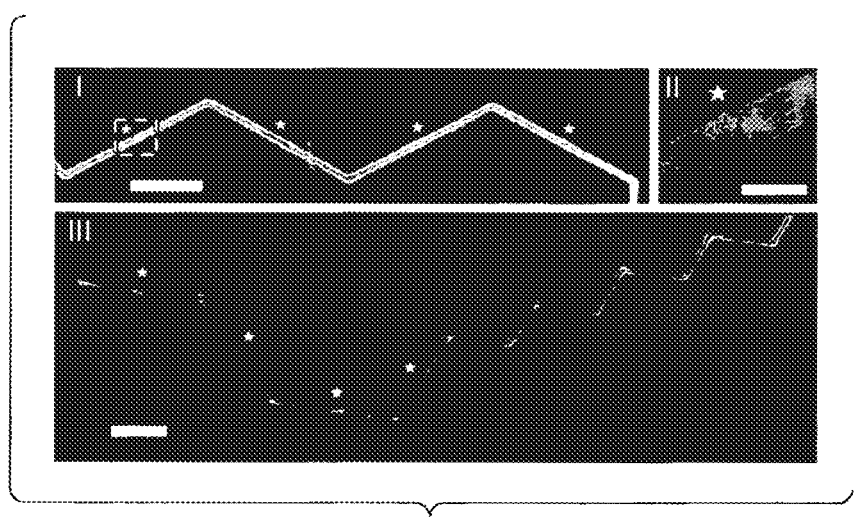

The model described in Example 4 may allow the design and synthesis of specific structures in silicon nanowires and, more generally, nanowire systems with distinct compositions. To illustrate this point, in this example, (kink-node)$_m$ and (kink-node)$_m$(kink)$_n$ modulated silicon nanowire structures were designed and synthesized, where m and n are indices denoting the number of times the structural unit's growth is repeated. 150 nm gold as catalysts were chosen, with 15 s and 1 s as purge durations (FIG. 3D) for the growth of kinks and nodes, respectively. Notably, SEM images of the (kink-node)$_m$ structure (FIGS. 3F, I and II) showed that the nodes (highlighted with stars) were reproducibly inserted between kinks over multiple modulations. FIG. 3F illustrates SEM images of 2D silicon nanowires with modulated kinks and incipient kinks (starred nodes). I corresponds to a designed (kink-node)$_m$ structure, II is zoom of one node from the region indicated by the dashed yellow square in I, and III corresponds to a, (kink-node)$_m$(kink)$_n$ structure, where m and n are integers. The scale bars in I, II and III are 1, 0.2 and 1 µm, respectively.

These results also showed that the formation of individual kinks or nodes can be independent of adjacent elements and may be controlled by growth conditions. This point and possible control is further demonstrated by the synthesis of coherent (kink)$_8$ SBUs following modulated (kink-node)$_4$ units (FIG. 3F, III). Interestingly, the observation of coherent zigzag chain structures suggests that "steering" of kinks is not random and might be due, for example, to a minimization of stress or maintenance of the centre-of-mass of the whole structure. These results highlight the potential of this approach to generate in a predictable manner complex 2D nanowire structures.

EXAMPLE 6

This model may also be used for the designed synthesis of 2D kinked nanowire structures in other materials. For example, SEM images (FIG. 4A) of Ge nanowires grown using the iterative approach of FIG. 1A (see below) show nanowires with well-defined kinks, where the kink angle, 120°, is consistent with that for the SBU. TEM images (FIG. 4B) further demonstrated that the growth direction of the arms of the 2D kinked Ge nanowires was along the <112> direction. This also shows that the joint was single crystalline. These structural details were consistent with the features observed in kinked silicon nanowires as discussed in the examples above (e.g., FIGS. 1 and 2). This model also shows the arm-joint-arm kink SBU could be realized in very different materials such as the wurtzite phase of the group II-VI semiconductor CdS. Notably, designed iterative modulation of the growth of <11-20> direction CdS nanowires may yield a regular 2D kinked structure with 120° kink angle as shown in FIG. 4C. TEM images (FIG. 4D) demonstrated that the CdS 2D kinked nanowire structure was single-crystalline with arms all along the <11-20> direction of the wurtzite phase. This approach could also be used for the designed synthesis of 2D kinked group III-V nanowire materials such as GaN nanowires, potentially with almost pure <11-20> orientation.

Figure 4A:
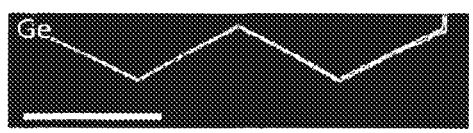
FIGS. 4A-4D illustrate various semiconductor nanoscale wires, in other embodiments of the invention.
Figure 4C:
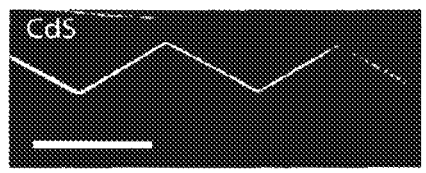
Figure 4B:
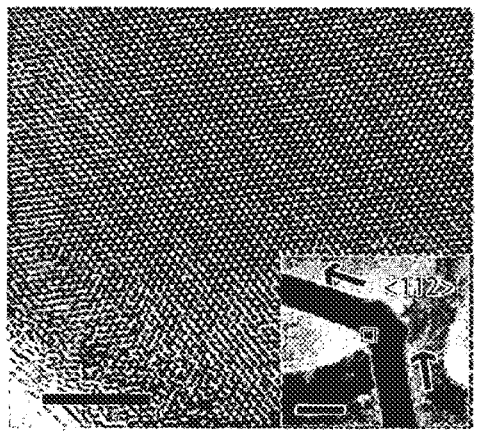
Figure 4D:
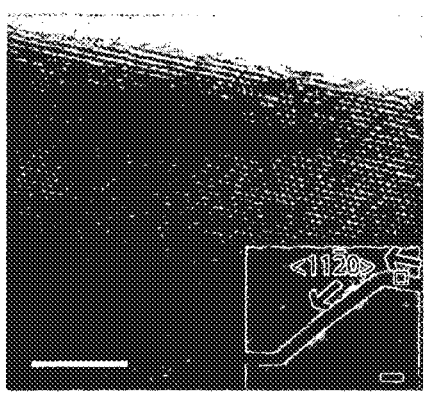

With respect to FIG. 4, FIG. 4A illustrates an SEM image of one multiply kinked germanium nanowire; scale bar is 1 micrometer. The dashed square highlights one SBU with a 120° arm-joint-arm angle. FIG. 4B illustrates a lattice-resolved TEM of the joint region of a representative germanium nanowire kink; scale bar is 5 nm. The inset highlights one SBU with arrows corresponding to <112> growth directions and the square indicates the region where the high-resolution image was recorded. The inset scale bar is 50 nm. FIG. 4C is an SEM image of one multiply kinked cadmium sulphide nanowire; scale bar is 1 micrometer. The dashed square highlights one SBU with a 120° arm-joint-arm angle. FIG. 4D is a lattice-resolved TEM of the arm region of a representative cadmium sulfide adjacent to the kink joint; scale bar is 5 nm. The inset highlights two SBU with arrows corresponding to <11-20> growth directions and the square indicates the region where the high-resolution image was recorded. Inset scale bar is 50 nm.

EXAMPLE 7

This example illustrates the use of approaches such as the ones described above to generate more complex nanowires with potentially unique function integrated at the nanoscale in the topologically-defined points of the kinks. This I shown by combining the iterative growth approach used in the previous examples with additional modulation of dopant to vary electronic characteristics in a well-defined manner with respect to the kinks.

Figure 5A:
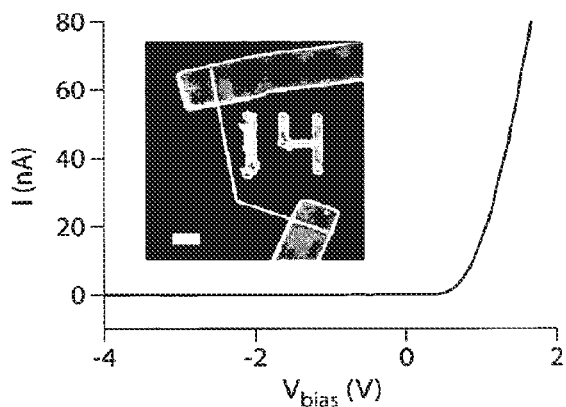
FIGS. 5A-5E illustrate various nanoelectronic devices containing nanoscale wires, in one set of embodiments.
Figure 5B:
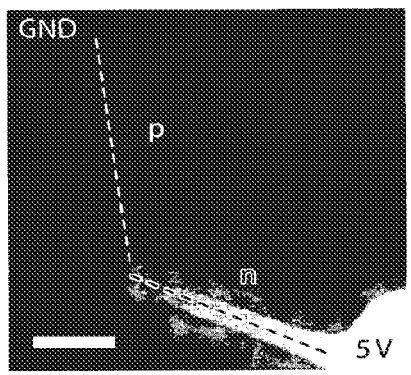

A kinked Si nanowire SBU with integrated n- and p-type arms was synthesized by switching phosphine and diborane dopants during the kink growth sequence (see below). Current-voltage (I-V) data recorded on a representative single kink device (FIG. 5A) revealed a current rectification in reverse bias with an onset at forward bias voltage of about 0.6 V, consistent with the synthesis of a well defined p-n diode within the kinked structure. The inset shows an SEM image of the device structure. The scale bar is 2 micrometers. Moreover, an electrostatic force microscopy image of a typical kinked p-n nanowire in reverse bias (FIG. 5B) showed that the voltage drop occurs primarily at the designed p-n junction localized and labeled by the kink during growth. In particular, this figure is an electrostatic force microscopy image of a p-n diode reverse-biased at 5 V. The AFM tip voltage was modulated by 3 V at the cantilever-tip resonance frequency. The signal brightness was proportional to the nanowire device surface potential, and showed an abrupt drop around the kink position. The dashed lines mark the nanowire position.

EXAMPLE 8

Figure 5C:
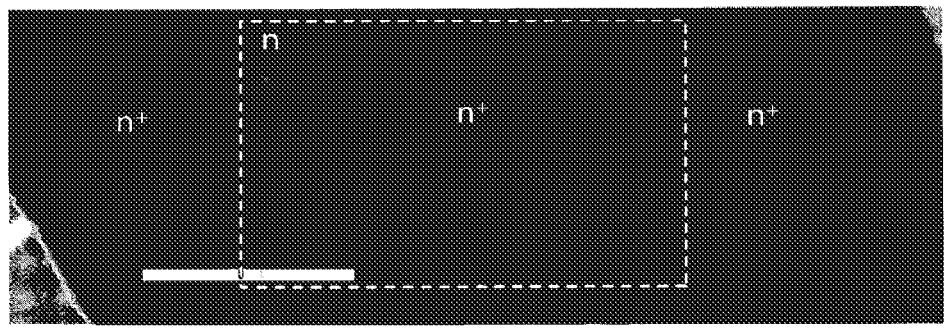
Figure 5D:
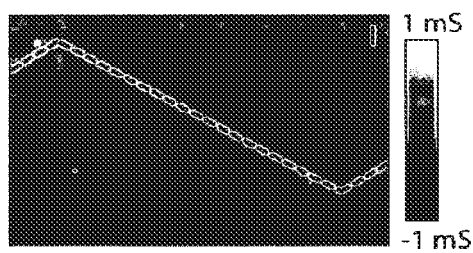
Figure 5E:
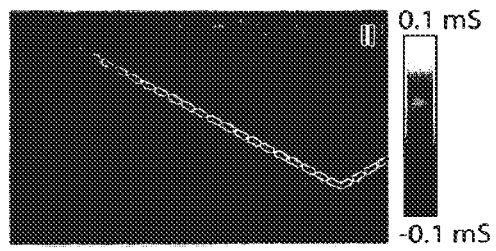

This example illustrates the design and synthesis of nanowires with distinct functionality at sequential kinks. A representative atomic force microscopy image of a double kink structure synthesized with n$^+$ and n dopant profiles at the two kink joints (FIG. 5C) showed that the characteristic SBU described above appeared to be generally unaffected by multiple modulations of dopant concentration. Notably, scanned gate microscopy data (FIG. 5D) demonstrated enhanced (decreased) nanowire conductance as the tip with positive (negative) gate potential was scanned across the designed n-type segment immediately adjacent to the upper-left kink junction, thus confirming the integration of an n-type field-effect transistor at a well-defined and recognizable point on the structure. The absence of gate response from the lower-right kink junction (FIG. 5D-5E) further showed that the single crystalline kink structure itself does not appear to alter the electrical transport properties. FIGS. 5C-5E are AFM and scanning gate microscopy images of one $n^+$-kink-$n^+$-kink-($n$-$n^+$) dopant modulated double-kinked silicon nanowire structure. The scale bar in FIG. 5C corresponds to 2 micrometers. The scanning gate images were recorded with a $V_{tip}$ of 10 V (I, FIG. 5D) and −10 V (II, FIG. 5E), respectively, and a $V_{sd}$ of 1 V. The dark and bright regions correspond to reduced and enhanced conductance, respectively. The dashed lines mark the nanowire position.

EXAMPLE 9

This example illustrates various methods used in Examples 1-8. Single-crystalline kinked nanowires were synthesized by the nanocluster-catalyzed VLS method described herein. Silicon nanowires were synthesized at 450-460° C. using monodisperse gold nanoclusters as catalysts, silane as the silicon reactant, hydrogen as the carrier gas, and phosphine and diborane as the n- and p-type dopants. The total pressure during growth was 40 ton and the minimum pressure during the purge cycle was about $3 \times 10^{-3}$ torr. These conditions yielded dominant growth direction of <112> (FIG. 7), and it should be noted that Si nanowires with <111> growth direction generally did not exhibit kinks for conditions optimized for the SBU in <112> oriented nanowires.

Germanium nanowires were synthesized with gold nanocluster catalysts at 270-290° C., using germane and other conditions similar to silicon. Cadmium sulfide nanowires were grown in a three-zone furnace by evaporating CdS power at 650-720° C., with nanowire growth by gold nanocluster catalyzed VLS method at 550-500° C. zone. The purge cycle for kinks in the Ge and CdS nanowires was typically 15 s.

Devices for electrical transport measurements were fabricated on silicon substrates (100 nm oxide/200 nm nitride, 0.005 Ohm cm resistivity, Nova Electronic Materials), where Ti/Pd (1.5 nm/100 nm) contacts were defined by electron beam lithography and deposited by thermal evaporation. Current-voltage (I-V) data were recorded using a semiconductor parameter analyzer with a probe station. Electrostatic force and scanned gate microscopy measurements were carried out with a Digital Instruments Nanoscope Ma MultiMode AFM and metal coated tips. The surface potential and conductance maps were acquired in lift mode with a lift height of 40 and 20 nm, respectively.

Nanowire synthesis. Single-crystalline kinked nanowires were synthesized by the nanocluster-catalyzed VLS method in quartz tube connected to gas manifold and vacuum pump and heated by a temperature controlled tube furnace. Monodisperse gold nanoparticles (Ted Pella) were dispersed on $SiO_2$/Si or sapphire growth substrates, which were placed within the central region of the quartz tube reactor. The silicon (Si) nanowires were synthesized at 450-460° C. using silane ($SiH_4$) as the silicon reactant source, hydrogen ($H_2$) as the carrier gas, and phosphine ($PH_3$, 1,000 p.p.m. in $H_2$) and diborane ($B_2H_6$, 100 p.p.m. in $H_2$) as the n- and p-type dopants. In a typical synthesis of uniform n-type, 80 nm kinked silicon nanowires, the flow rates of $SiH_4$, $PH_3$ and $H_2$ were 1-2, 2-10 and 60 standard cubic centimetres per minute, respectively, and the total pressure was 40 ton and purge duration was 15 s; the minimum pressure during the purge cycle was about $3 \times 10^{-3}$ torr. The dopant feed-in ratios (silicon:boron/phosphorus) in kinked p-n silicon nanowires were 500:1 for both p- and n-type segments. In $n^+$-kink-$n^+$-kink-($n$-$n^+$) dopant modulated silicon nanowires, the silicon-phosphorus feed-in ratios were 200:1 and 10000:1 for $n^+$- and n-type segments, respectively, and the n-segment was grown for 30 s.

Germanium nanowires were synthesized at 270-290° C., 40 torr, with germane ($GeH_4$, 10% in $H_2$) and $H_2$ as the reactant and carrier gas, respectively.

Cadmium sulfide nanowires were grown in a three-zone furnace by evaporating CdS power at 650-720° C., with nanowire growth by gold nanocluster catalyzed VLS method at 550-500° C. The purge cycle used to form kinks in the germanium and cadmium sulphide nanowires was typically 15 s.

Structure characterization. Zeiss Ultra55/Supra55VP field-emission SEMs and JEOL 2010 field emission TEM were used to carry out SEM and TEM analyses, respectively. For sample preparation, all kinked nanowires were gently sonicated in isopropyl alcohol and dispersed onto heavily doped silicon substrates (100 nm oxide/200 nm nitride, 1-10 Ohm cm resistivity, Nova Electronic Materials, Carrollton, Tex.) or lacey carbon grids (Ted Pella).

Device fabrication and measurement. Devices were fabricated on silicon substrates (Nova Electronic Materials, n-type 0.005 Ohm cm) with 100 nm thermal oxide and 200 nm silicon nitride at the surface. Devices were defined by electron-beam lithography followed by Ti/Pd (1.5 nm/100 nm) contact deposition in a thermal evaporator. Current-voltage (I-V) data were recorded using an Agilent semiconductor parameter analyzer (Model 4156C) with contacts to devices made using a probe station (Desert Cryogenics, Model TTP4). Electrostatic force microscopy and scanned gate microscopy measurements were carried out with a Digital Instruments Nanoscope IIIc MultiMode AFM and metal coated tips (Nanosensors, PPP-NCHPt). The electrostatic force microscopy surface potential maps and scanned gate microscopy conductance maps were acquired in lift mode with lift heights of 40 and 20 nm, respectively.

In the surface potential measurements, the p-n diode was reverse-biased at 5 V and the tip voltage was modulated by 3 V at the resonance frequency. In scanned gate measurements, the tip functions as a local gate $V_{tip}=\pm 10$ V, and the conductance versus position provided a measure of local accumulation or depletion of carriers in the device.

EXAMPLE 10

Figure 9B:
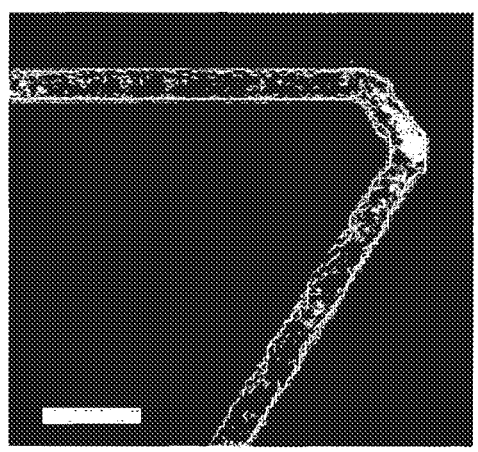
FIG. 9B shows an SEM image of a bent nanoscale object, according to an embodiment.

The example demonstrates fabrication of a two-terminal semiconductor device for interfacing single cells intracellularly. The device includes single crystalline kinked silicon nanowire structures with sharp junction angles (FIG. 9A) that were synthesized using a nanotectonic approach. Two or three 120° kinks with separation distances (L) less than 250 nm were sequentially introduced during the nanocluster catalyzed chemical vapour deposition process. A representative scanning electron microscopy (SEM) image of an 80 nm diameter, doubly kinked nanowire (FIG. 9B) shows well defined two adjacent 120° kinks with L~160 nm and an overall 60° junction angle, consistent with the schematic diagram (FIG. 9A, 100).

Figure 9C:
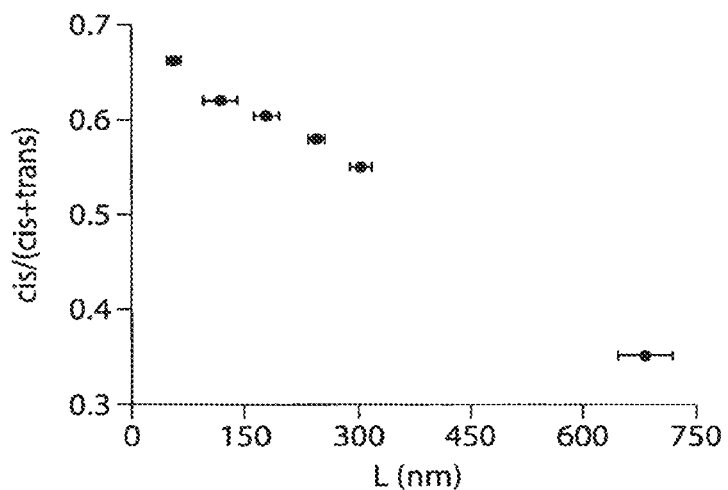
FIG. 9C shows a cis/(cis+trans) vs. L plot, according to an embodiment.
Figure 9D:
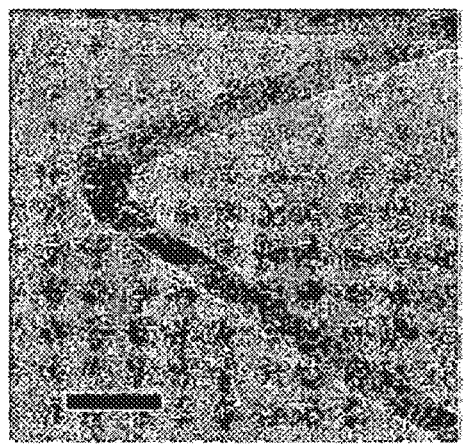
FIG. 9D shows a TEM image of a bent nanoscale object, according to an embodiment.

Similar to describing the molecule conformations, 'cis' and 'trans' crystal conformations were introduced to delineate doubly kinked nanowire structures where segments 110 and 112 are on the same (FIG. 9A, 100) and different (FIG. 9A, 102) sides of segment 111, respectively. One step in synthesizing the kinked nanowire structures with either 60° or 0° junction angles (FIG. 9A, 100 and 101) instead of the open structure (FIG. 9A, 102) was to grow the 'cis' forming kinks controllably. Next, the segment length (L) was varied from ~700 to 50 nm for doubly kinked silicon nanowires having a diameter of 80 nm. A plot of the cis/(cis+trans) ratio as a function of L in these doubly kinked structures (FIG. 9C) shows that the 'cis' conformation became dominant as L shrunk, and vice versa, indicating that sharp angle kinked nanowire structures (FIG. 9A, 100 and 101) can be selectively grown with reasonable yield. Significantly, the diameter and segment length of the 60° kinked silicon nanowires can be pushed down to ~18 and 15 nm (FIG. 9D, FIG. 13), respectively, suggesting a potential filamentous semiconductor probe with dimensions smaller than microtubules in single cells. Finally, dopant modulation in 60° kinked nanowires was achieved. Specifically, as used elsewhere in this example, a short (~200 nm) and lightly doped n-type field effect transistor (FET) was integrated near the tips of the 60° kinked nanowires, as confirmed by scanning gate microscopy measurement (FIG. 14B).

Figure 9E:
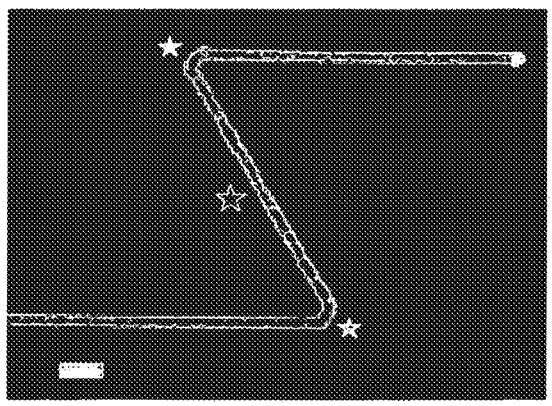
FIG. 9E shows an SEM image of a bent nanoscale object, according to an embodiment.
Figure 9F:
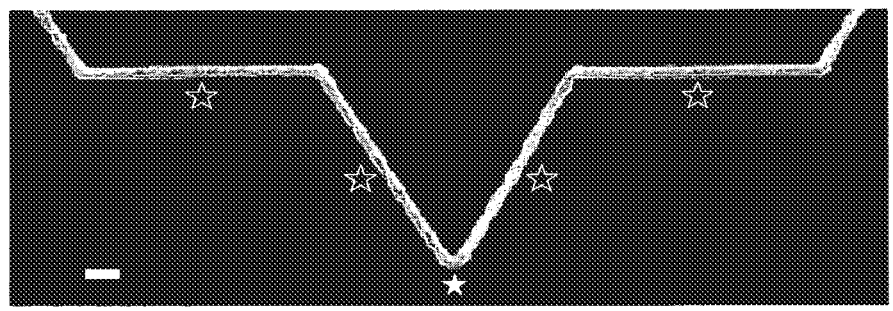
FIG. 9F shows an SEM image of a bent nanoscale object, according to an embodiment.
Figure 9G:
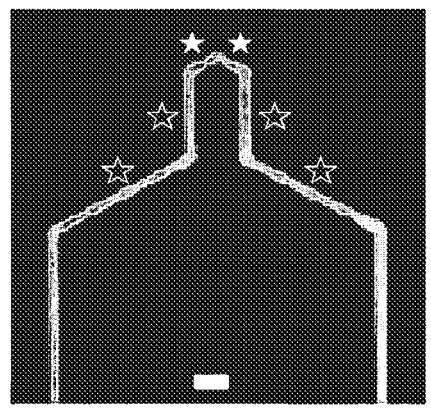
FIG. 9G shows an SEM image of a bent nanoscale object, according to an embodiment.

To address the potential of ab initio design and synthesis, kinked nanowire structures were prepared with double 60° junctions (FIG. 9E), integrated 60° and 120° junctions (FIG. 9F), and integrated 0° and 120° junctions (FIG. 9G). The segments that form 'cis' conformation (yellow stars) were shorter than 250 nm but were longer than 650 nm for 'trans' ones (magenta stars), consistent with the data shown in FIG. 9C and demonstrating the conformation control for independent syntheses.

Figure 10A:
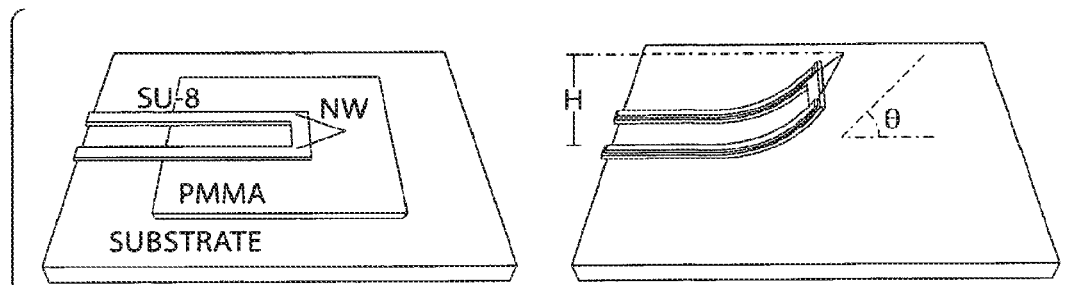
FIG. 10A shows schematics of device fabrication, according to an embodiment.
Figure 10B:
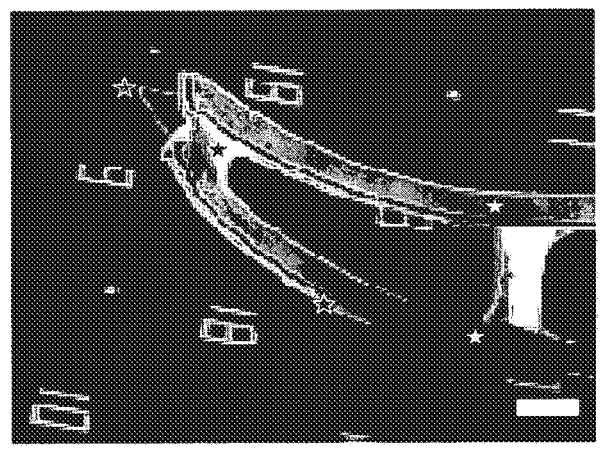
FIG. 10B shows an SEM image of a bent nanoscale object, according to an embodiment.
Figure 15A:
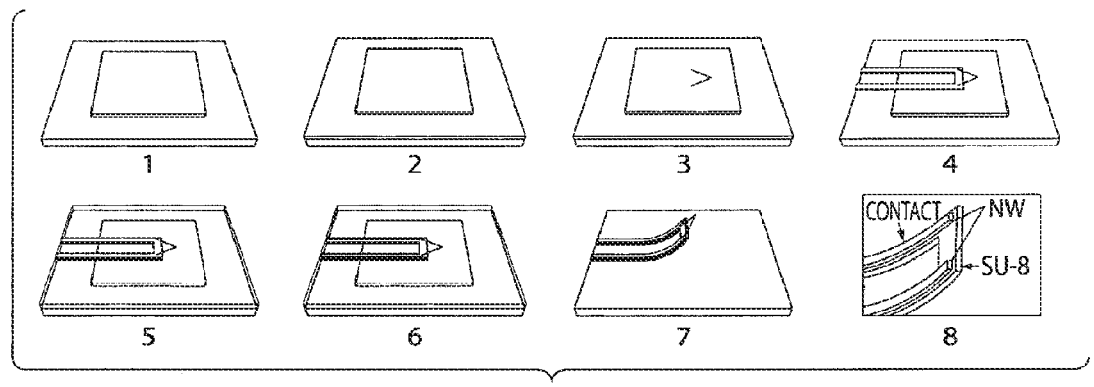
FIGS. 15A-15B shows a schematic of fabrication steps and shows a plot of dependence of the tip height and angle versus the length of relieved metal, according to an embodiment.
Figure 15B:
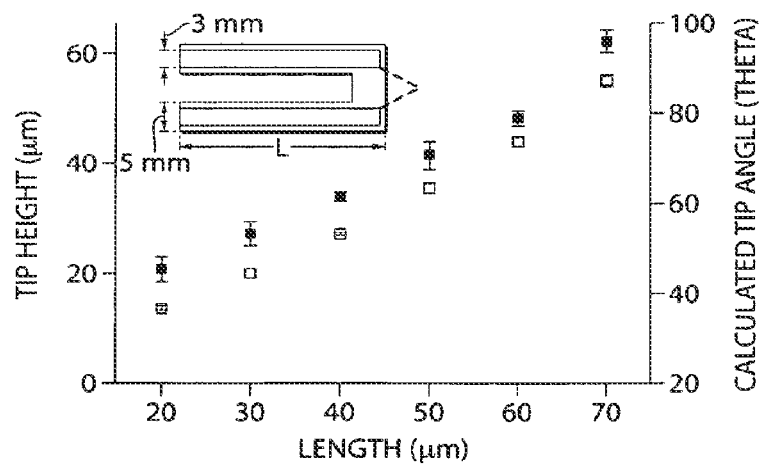

A free-standing and flexible nanowire field effect transistor device was designed for interfacing biological systems in three-dimensions (3D) (FIG. 10A, FIG. 15, and Methods). The approach to suspending the devices from the substrate utilized the interfacial stress between different materials to bend and actuate the micron-scale layered structures. The SEM and optical microscopy images of one free-standing device (FIG. 10B) highlight several important features. Firstly, the 60° kinked nanowire (stars on the left) was intact after fabrications with two terminals sandwiched between epoxy micro-ribbons (stars in the middle) and metal contacts (stars on the right), consistent with designs (FIG. 10A). Secondly, the tip height and angle (H, θ) (theta) of the device in air and in water were (25 micrometers, 43°) and (38 micrometers, 90°), respectively (FIG. 2B, II, III). The larger bending of the device in water might be a result of decrease in elastic modulus of epoxy ribbons and suggests that the nanowire probe device is intrinsically flexible and can potentially be triggered chemically. Thirdly, the probe orientation (H, θ) could be tuned arbitrarily and reproducibly by changing, e.g. the length of the free-standing part of hybrid structure (FIG. 15) and the thicknesses of each layers. Finally, the free-standing FET devices could be stored in air for at least 8 months without substantial change in probe orientations and electrical transport properties.

Figure 16A:
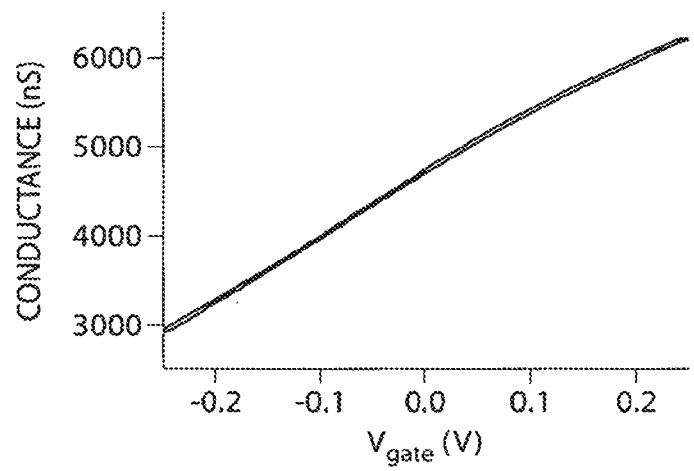
FIG. 16A shows a plot of conductance vs. water-gate voltage measurements for a typical free-standing nanowire probe device, according to an embodiment.

Mechanically elastic and electrically robust probe devices are of particular interest for a number of practical applications. In this regard, a glass micropipette was used to vary the probe tip height manually by pressing or lifting the soft epoxy backbones in phosphate buffered saline (PBS) solution (FIG. 10C, inset) while recording the device conductance and watergate sensitivity changes. The free-standing, nanoscale FET probe devices normally show a watergate sensivity of 4-8 microsiemens/V in PBS solution without deformations (FIG. 16A). Measurements of a typical device (FIG. 10C) yield a <20 nS conductance change within a ~18 micrometer deflection in H, corresponding to a <0.31% fluctuation in the total device conductance and a <3.2 mV potential change in PBS solution. Likewise, the device sensitivity remained stable with a maximum change of ~0.15 microsiemens/V, a 2.4% variation of total watergate sensitivity. In addition, both device orientation and electrical transport properties recovered to their initial states after the micropipette detached the probe device, and repetitive bending did not degrade the device performance.

Figure 10C:
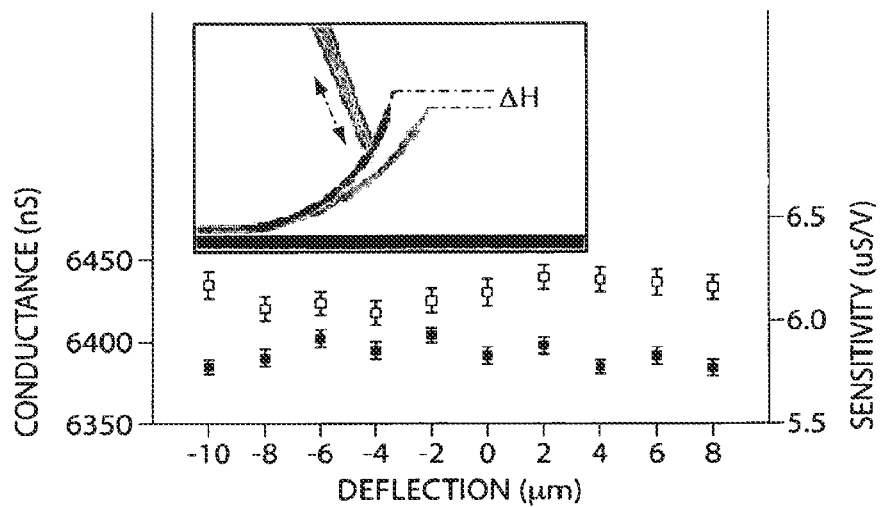
FIG. 10C shows a plot of device conductance and sensitivity under external bending and shows an experiment schematic of external bending (inset), according to an embodiment.
Figure 10D:
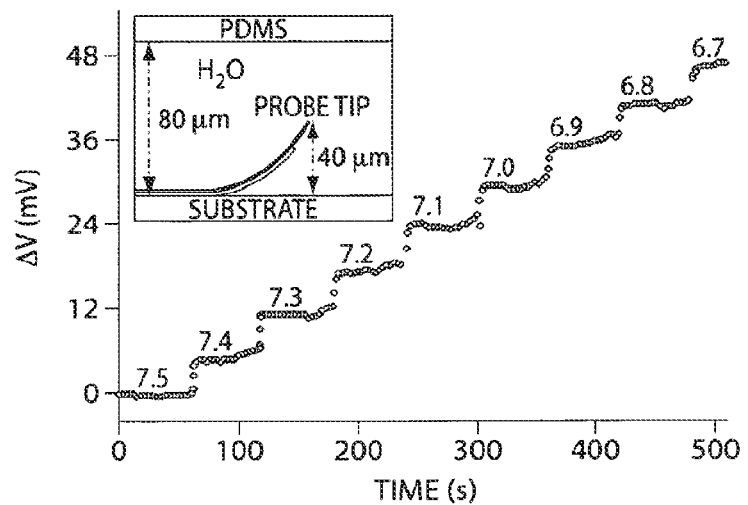
FIG. 10D shows a plot demonstrating nanoscale pH sensor properties and shows an experiment schematic, according to an embodiment.

To show that the free-standing FET devices can serve as a 3D 'point' sensor for biological and chemical species, a pH sensing cell comprising a microfluidic channel formed between a poly(dimethylsiloxane) (PDMS) mold and the nanowire probe/substrate was assembled (FIG. 10D, inset). Measurements of the calibrated nanowire surface potential as a function of time and solution pH (FIG. 10D) demonstrated that the potential increased stepwise with discrete changes in pH from 7.5 to 6.7 and that the potential was constant for a given pH. The pH sensitivity was ~58 mV/pH, which is close to the Nernstian limit. In addition, the changes in surface potential were also reversible for increasing and/or decreasing pH (FIG. 16B).

FIGS. 9A-9G. Synthesis of kinked silicon nanowire probes. (A) Schematics of 60° (top) and 0° (middle) multiply-kinked nanowires, and 'cis' (top) and 'trans' (bottom) configurations in nanowire structures. 1, 2, and 3 denote three sequential segments that are separated by two adjacent 120° kinks. L is the length of segment 2. (B) SEM image of a doubly-kinked nanowire with 'cis' configuration. (C) cis/(cis+trans) vs. L plot. (D) Transmission electron microscopy image of an ultrathin 60° kinked nanowire. (E) SEM image of a kinked nanowire with double 60° junctions. (F) and (G) SEM images of 60° (F.) and 0° (G) kinked nanowires with extended arm configurations. Scale bars, 200 nm in (B), (E), (F), and (G); 50 nm in (D).

FIGS. 10A-10D. Freestanding and flexible devices. (A) Schematics of device fabrication. The patterned PMMA and SU-8 epoxy micro-ribbons serve as sacrificial layer and flexible device support, respectively. The dimensions of the lightly doped n-type silicon segment are about 80×80×200 nm$^3$. H and θ (theta) are tip height and orientation, respectively. (B) SEM image of an as-made device. Left, center, and right stars mark the nanowire, SU-8, and metal layers, respectively. The scale bar is 5 micrometers. (C) Device conductance and sensitivity under external bending. The deflections were recorded as the change in tip height H. Inset, experiment schematics. (D) High performance 3D nanoscale pH sensor. Inset, experiment schematics. FIG. 13. TEM images of ultrathin 60° nanowire probes. The segment lengths between adjacent 120° cis-kinks in (A) and (C) are ~50 nm and ~15 nm, respectively. (B) and (D) are high-resolution TEM images recorded in the square regions of single 120° kinks marked in (A) and (C), respectively. HRTEM images show that the nanowires are single crystalline and that their arms follow the <112> growth orientation ((B), (D), arrows), as previously described in U.S. Provisional Patent Application Ser. No. 61/245,641, filed Sep. 24, 2009, entitled "Bent Nanowires," by Tian et al., which is incorporated herein by reference. All TEM images were acquired with the electron beam perpendicular to the 2D plane of the kinked nanowires. Scale bars, 50 nm in (A) and (C), and 2 nm in (B) and (D).

Figure 16B:
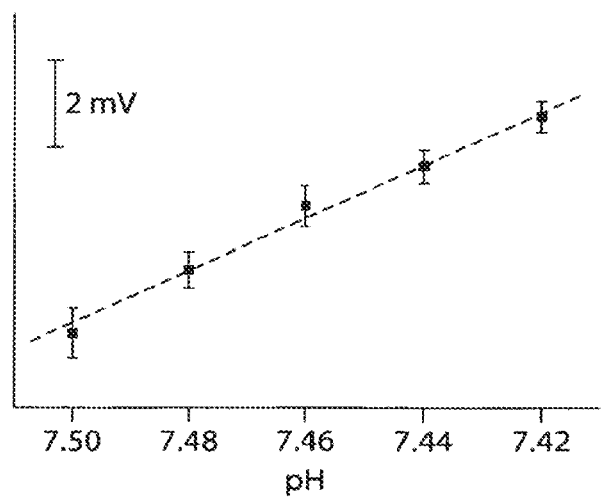
FIG. 16B shows a plot of calibrated nanowire surface potential change vs. solution pH, according to an embodiment.

FIGS. 16A and 16B. Kinked nanowire probe characterization in aqueous solution. (A) Conductance vs. water-gate voltage measurement for a typical free-standing nanowire probe device. The device sensitivity is 6.8 microsiemens/V in PBS solution. The data was recorded with a 100 mV DC source voltage, and the current was amplified with a home-built multi-channel current/voltage preamplifier, filtered with a 3 kHz low pass signal conditioner (CyberAmp 380), and digitized at a 50 kHz sampling rate (Axon Digi1440A). (B) Calibrated nanowire surface potential change vs. solution pH. The slope of the linear fit (dashed line) yields a pH sensor response of ~59.7 mV/pH. The sensitivity limit is ~0.02 pH, with S/N>1.3. The error bars denote ±1 standard deviation. Data was recorded in a microfluidic channel as illustrated in FIG. 10D, inset. The pH sensing measurements were conducted using a lock-in amplifier with a modulation frequency of 79 Hz, time constant of 30 ms, amplitude of 30 mV. The DC source-drain potential is zero. A Ag/AgCl reference electrode was used in (A) and (B).

EXAMPLE 11

Figure 11A:
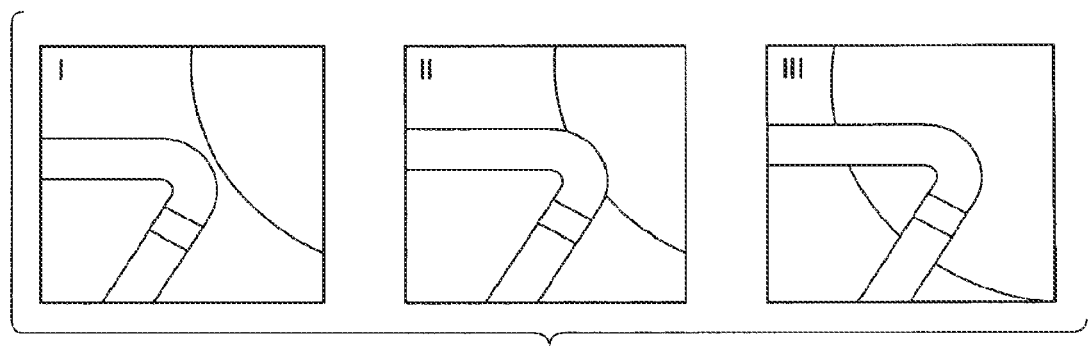
FIG. 11A shows schematics of nanowire entrance into a cell, according to an embodiment.
Figure 11B:
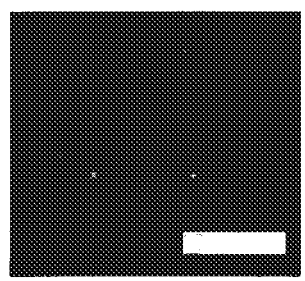
FIG. 11B shows a false colored fluorescence image of a lipid coated nanowire probe, according to an embodiment.

The possibility of establishing an electrical interface between single cells and solid state semiconductor devices intracellularly was investigated in this example (FIG. 11A). As stable and self-healing elements, phospholipid bilayers can fuse with each other. Thus, the 60° kinked nanowires were modified with phospholipids (1,2-dimyristoylsn-glycero-3-phosphocholine (DMPC)) by fusing unilamellar vesicles onto the negatively charged nanowire surface. Fluorescence microscopy images show that DMPC lipid bilayers formed a continuous shell on the silicon nanowire core (FIG. 11B). Without wishing to be bound by any theory, it is proposed that when a cell is brought into contact with the hybrid core-shell nanowire (FIG. 11A, I), the lipid bilayers from nanowire shell and cell membrane fuse together, which exposes the tip of the silicon core to the cytosol (FIG. 11A, II). Subsequently, the nanoscale FET sensor (shaded middle segment) enters the cell (FIG. 11A, III) and is sealed with the fused membrane.

Figure 11C:
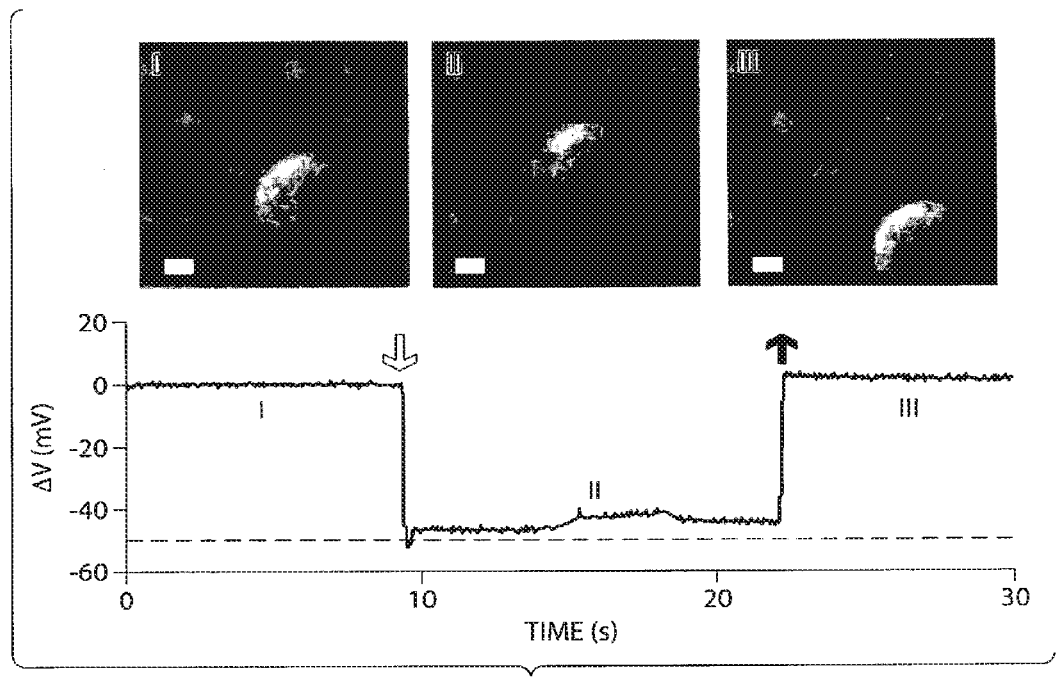
FIG. 11C shows differential interference contrast (DIC) microscopy images (upper panel) and shows a plot of electrical recording (lower panel) of an HL-1 cell interacting with a phospholipid coated 60° kinked nanowire probe, according to an embodiment.
Figure 11D:
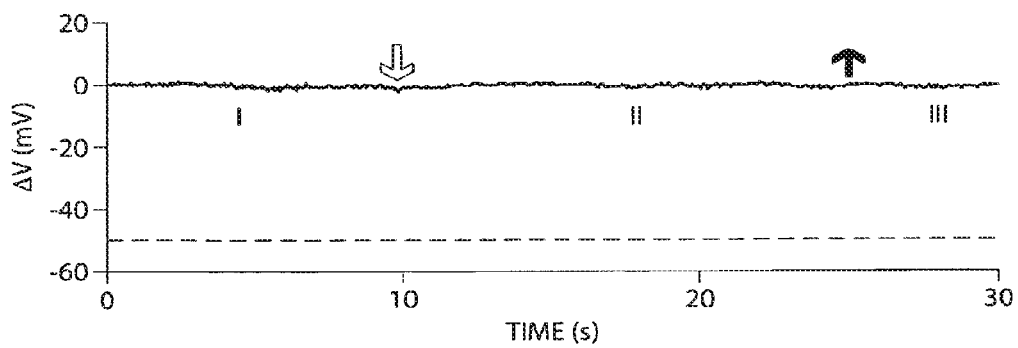
FIG. 11D shows a plot of electrical recording with a 60° kinked nanowire probe without phospholipids surface modification (refers to FIG. 11C, top panel), according to an embodiment.

As a proof-of-concept demonstration of intracellular electrical recording, the calibrated potential change of one kinked nanowire probe (FIGS. 11B and 11C) was monitored upon its cellular entrance into an isolated HL-1 cell (FIG. 11C, I, II, III). A glass micropipette (inner tip diameter, ~5 micrometers) was used to pick up one cell from suspension and hold its intracellular potential at −50 mV. Then, the same micropipette was used to approach the cell onto the lipid-coated nanowire tip at a speed of ~30 micrometers/s with an x-y-z micromanipulator. Measurement of the potential versus time from the FET device showed a sharp ~52 mV drop within 250 ms after cell/tip contact, and the potential maintained at ~46 mV before going back to the baseline when the cell was detached from the nanowire by pulling (~30 micrometers/s). Control experiments using a nanowire probe device without a lipid shell yielded <1.5 mV potential fluctuation upon cell/tip contact (FIG. 11D), which corroborates the proposed model (FIG. 11A) and suggests that membrane fusion is a possible mechanism of assisting device intracellular entrance. In addition, the marginal conductance/potential change (FIG. 11D) as the nanowire itself was deformed by the HL-1 cell, which further confirms that the free-standing nanoscale FET device is electrically robust (FIG. 10C).

FIGS. 11A-11D. Surface modification and cellular entrance. (A) Schematics of nanowire entrance into a cell. This diagram shows heavily doped nanowire segments (lighter shaded segments on the bent wire), active sensor segment (darker shaded segments), and the cytosol (upper quarter circle), and phospholipid bilayers (surrounding the wire and the cytosol), respectively. (B) Fluorescence image of a lipids coated nanowire probe. DMPC was doped with 1% NBD-dye labeled lipids and the hybrids were imaged through a 510/21 band pass filter. (C) Differential interference contrast (DIC) microscopy images (upper panel) and electrical recording (lower panel) of an HL-1 cell interacting with a 60° kinked nanowire probe: I) approaching, II) penetration, and III) withdrawal. Dashed line, micropipette holding potential. Scale bars: 5 micrometers. (D) Electrical recording with a 60° kinked nanowire probe without phospholipids surface modification. Down and up arrows in (C) and (D) mark the beginnings of cell penetration and withdrawal, respectively.

EXAMPLE 12

Figure 12A:
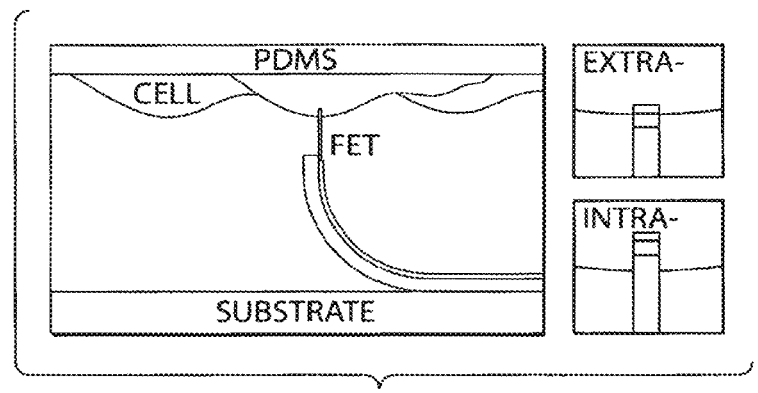
FIG. 12A shows schematics of cellular recording from cardiomyocyte monolayer on PDMS (left panel) and zoomed-in extra- and intracellular nanowire/cell interfaces (right panels), according to an embodiment.

The potential of the devices in interfacing with cultured electrogenic cells was evaluated in this example. To this end, interfaces between the freestanding FETs and embryonic chicken cardiomyocytes were established using a previously described method, in which the PDMS/cardiomyocyte cell substrates were positioned using a micromanipulator under an optical microscope to bring cells into direct contact with devices (FIG. 12A).

Figure 12B:
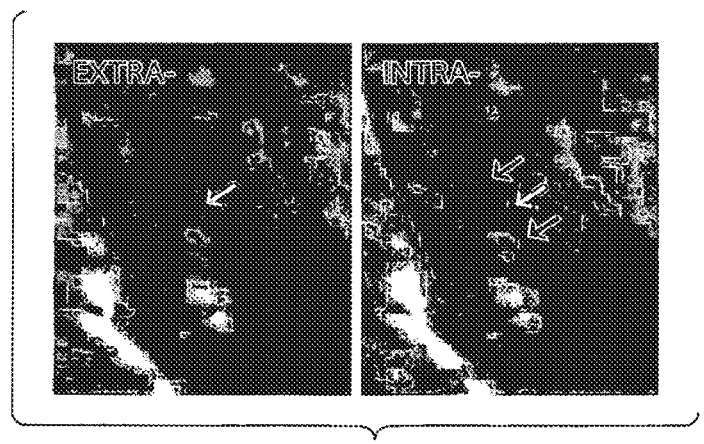
FIG. 12B shows DIC images of cells and a device used in extra- and intracellular measurements, according to an embodiment.
Figure 12C:
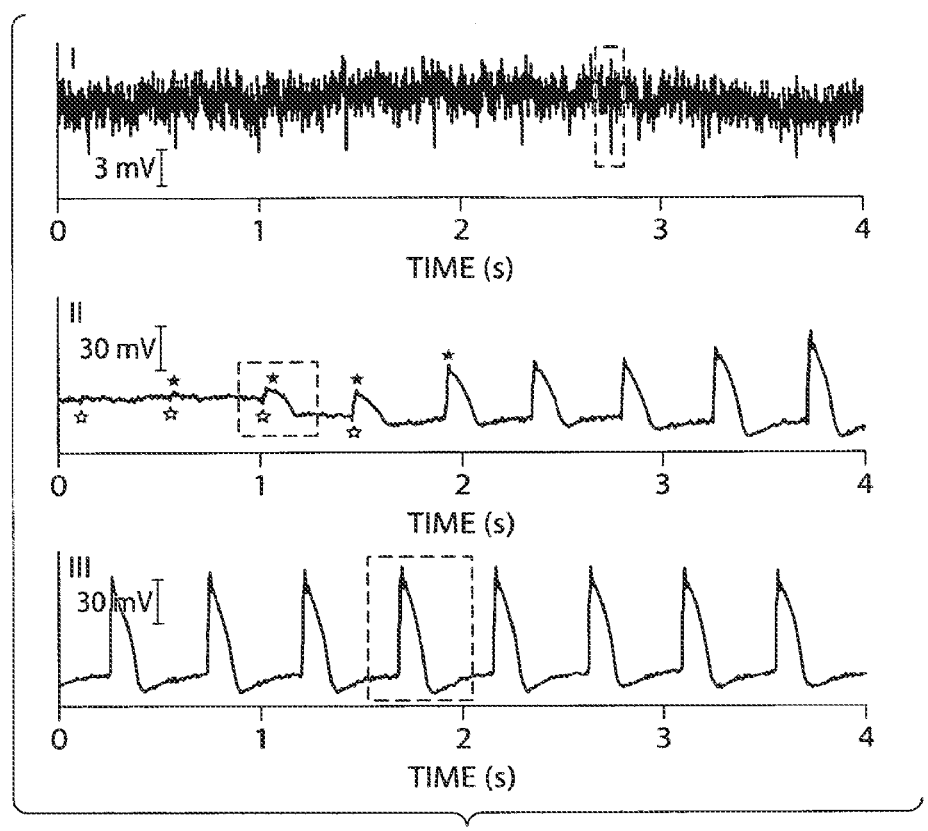
FIG. 12C shows plots of electrical recordings from beating cardiomyocytes, according to an embodiment.
Figure 12D:
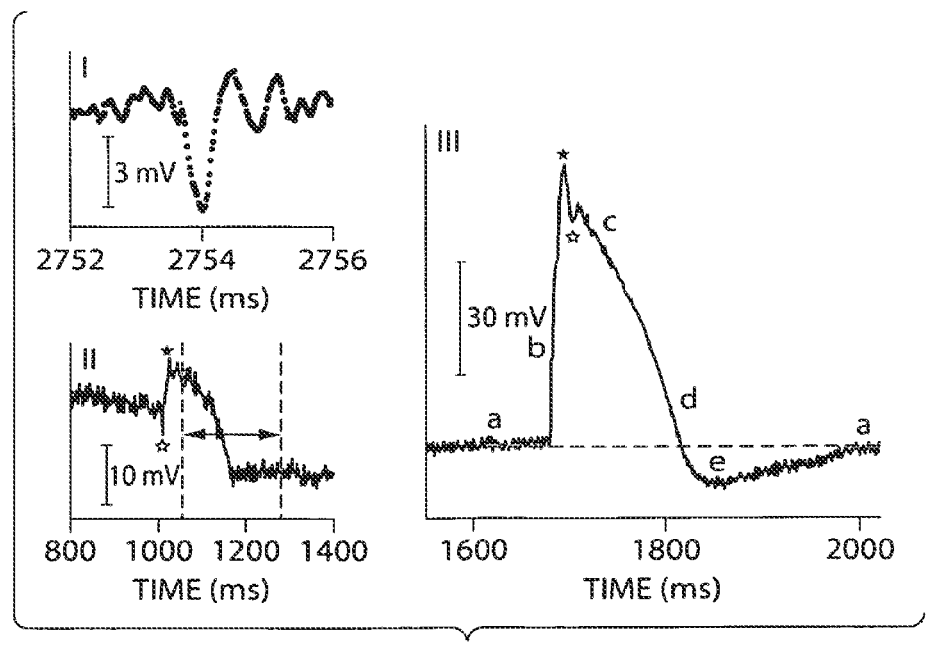
FIG. 12D shows magnified portions of FIG. 12C referring to the dashed square regions in FIG. 12C, according to an embodiment.
Figure 13A:
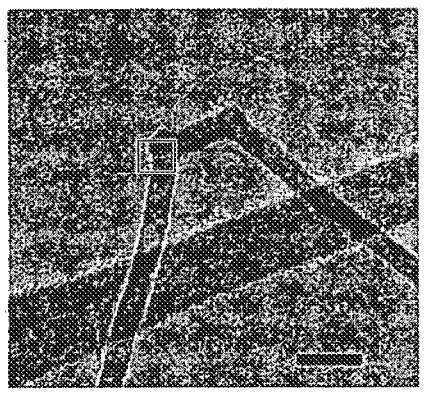
FIG. 13 shows TEM images of nanoscale objects, according to an embodiment.
Figure 13B:
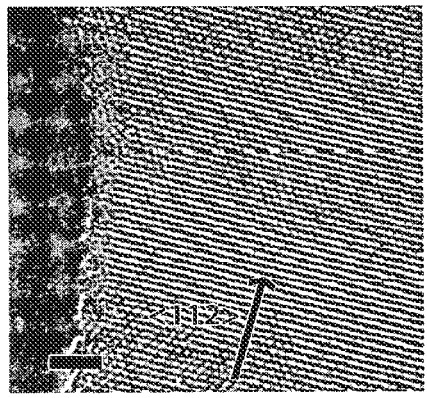
Figure 13C:
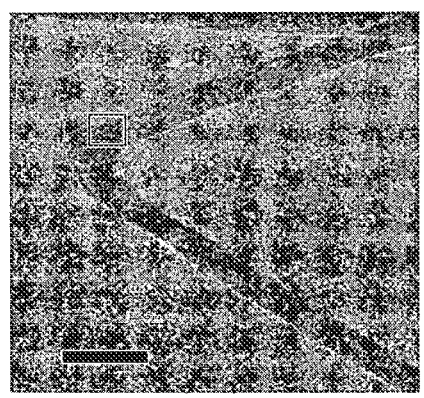
Figure 13D:

Measurements of the conductance versus time from a freestanding FET probe in gentle contact with a spontaneously beating cardiomyocyte cell monolayer (FIG. 12B) showed the following sequential features (FIG. 12C). Firstly, the regularly spaced spikes were immediately recorded with a frequency of about 2.3 Hz, a signal-to-noise ratio (S/N)≥2, a sub-microsecond duration, and a calibrated negative potential change of ~3-5 mV (FIG. 12C, I and FIG. 12D, I). The signal amplitude, the shape, and the sign (FIG. 12D, I) all agreed with the extracellular recordings. Although the S/N was poorer, it was consistent with the increased noise in short channel FET devices as used in this study. The nanowire/cell junction was likely filled with lipid layers from both the cell membrane and the probe shell (FIG. 12A, II), and the junction tightness in such protruding configurations can likely be improved by the nanowire lipid coating. These results highlight the ability to achieve extracellular recordings using a nano scale and free-standing detector and suggest the potential to interface with biological tissues such as brain slices in 3D.

Next, after the initial ~40 s upon the device/cell contact, several pronounced signal changes were observed (FIG. 12C, II and III). Firstly, the original extracellular recording signals gradually disappeared (FIG. 12C, II, lower stars). Secondly, with concomitant drop in baseline, new peaks with an opposite sign and much larger amplitude and duration emerged (FIG. 12C, II, upper stars) and then became steady (FIG. 12C, III). The largest calibrated amplitude of the stabilized recordings (FIG. 12C, III), ~80 mV, and the ~200 ms signal duration were close to those in whole-cell patch clamp recordings from cardiomyocytes and suggest that the electrical interface may have switched from capacitive extracellular coupling to Ohmic intracellular coupling. Thirdly, a zoom-in image of one of the later steady recordings (FIG. 12D, III) showed five characteristic phases of a cardiac intracellular potential: a) resting state, b) rapid depolarization, c) plateau, d) rapid repolarization, and e) hyperpolarization. In addition, the sharp transient peak (upper star) and the notch (lower star), mostly due to the inward sodium and outward potassium currents, could also be resolved. These features confirm that intracellular recordings from cardiomyocytes were achieved using two-terminal nanoscale FET devices. Finally, the steady intracellular recording (FIG. 12C, III) from the beating cardiomyocyte suggests a secure sealing with phospholipids layers and further corroborates the robustness of the nanowire devices.

Notably, close inspection of the transitional recordings (FIG. 12C, II) revealed additional important features. Firstly, the switching from extracellular to intracellular signals was smooth and without appreciable change in recording frequency. This suggests that the cellular entrance by the nanowire probe tip was less invasive and did not affect the electrogenic cell firing patterns. Such a natural transition may be a result of biomimetic membrane fusion that exposes the silicon nanowire tip directly into the cytosol (FIG. 11A and FIG. 12A, III). Second, the disappearance of extracellular signals, after the intracellular ones become dominant, suggests that the extracellularly exposed contacts and heavily doped silicon segments did not have a major contribution to the observed extracellular signals. It also confirms that two-terminal electrical recording was highly localized to the nanoscale FET segment near the probe tip. Third, the extracellular spikes were aligned with the position in intracellular ones where sodium influx initiated (FIG. 12D, II) and were temporally separated from the cardiac contraction (FIG. 12D, II, the regime between dashed lines), suggesting that the recorded extracellular signals (FIG. 12C, I) were not due to mechanical motion of the beating cells.

FIGS. 12A-12D. Electrical recording from cardiomyocytes. (A) Schematics of cellular recording from cardiomyocyte monolayer on PDMS (left panel), and zoomed-in extra- and intracellular nanowire/cell interfaces (right panels). The cell membrane and nanowire lipids coatings are marked as lines. (B) DIC images of cells and the device used in extra- and intracellular measurements. Arrows mark the nanowire tip and electrodes (left panel—nanowire tip; right panel—two electrodes surrounding a nanowire tip). Scale bars, 10 micrometers. (C) and (D) Electrical recording from beating cardiomyocytes. I) extracellular recording. II) a transition from extracellular to intracellular recordings during cellular entrance, and III) steady intracellular recording. (D) Zoom-in signals from the dashed square regions in (C).

EXAMPLE 13

This example describes various methods used in the above examples.

Nanowire synthesis and characterization. Single-crystalline nanowire probes were synthesized by a pressure modulated nanocluster-catalysed VLS method to generate kinks. In a typical synthesis of uniform n-type, 80 nm, 60° bent silicon nanowires, the flow rates of $SiH_4$, $PH_3$ and $H_2$ were 1-2, 2-10, and 60 standard cubic centimeters per minute, respectively, and the total pressure 40 torr and purge duration 10-15 s; the time interval between two purges is 20-40 s. In dopant modulated silicon nanowires, the silicon-phosphorus feed-in ratios were 200:1 and 10,000:1 for n+- and n-type segments, respectively, and the n-type segment was grown for 30 s. Zeiss Ultra55/Supra55VP field emission SEMs and a JEOL 2010 field-emission TEM were used to carry out SEM and TEM analyses, respectively.

Device fabrication. Devices were fabricated on silicon substrates (Nova Electronic Materials, n-type 0.005 V cm) with 100-nm thermal oxide and 200-nm SiN at the surface. Briefly, a poly(methyl methacrylate) (PMMA) layer was first patterned by e-beam lithography. Next, SU-8 2000.5 photoresist was spun-coated onto the substrate, and bent nanowires dispersed in isopropyl alcohol were deposited onto SU-8 layer. Then, ~300-400 nm SU-8 micro-ribbon features were formed by e-beam lithography and baking (180° C., 20 min). Next, methyl methacrylate (MMA) and PMMA double layers were spincoated and a last step of e-beam lithography was used to pattern the contact electrodes and passivation layers. Finally, Cr (1.5 nm)/Pd(50-80 nm)/Cr(50-80 nm) and 40-60 nm silicon nitride layers were deposited on SU-8 micro-ribbons by thermal evaporation and plasma enhanced chemical vapor deposition. The complete bent devices are self-actuated after lift-off process in acetone. See also FIG. 14.

Cellular recordings. HL-1 cells and embryonic chicken cardiomyocytes were cultured using the published protocols. The device chips were cleaned with $O_2$ plasma and the nanowire surfaces were then modified by vesicle fusion with a blend solution of 1,2-dimyristoyl-sn-glycero-3-phosphocholine (DMPC) and an NBD-labelled lipid, 1-myristoyl-2-{12-[(7-nitro-2-1,3-benzoxadiazol-4-yl) amino] dodecanoyl}-sn-glycero-3-phosphocholine. Nanowire recording was carried out in Tyrode solution with a 100 mV DC source voltage. The current was amplified with a home-built multichannel current/voltage preamplifier, and a 3000 Hz low pass signal conditioner (CyberAmp 380), and digitized at a 50 kHz sampling rate (Axon Digi1440A). Voltage clamp was performed with an Axopatch 200B from Molecular Device Systems using glass pipettes pulled on a P-97 Flaming/Brown-Micropipette Puller (Sutter Instruments). Ag/AgCl reference electrode was used in all recordings.

Figure 14A:
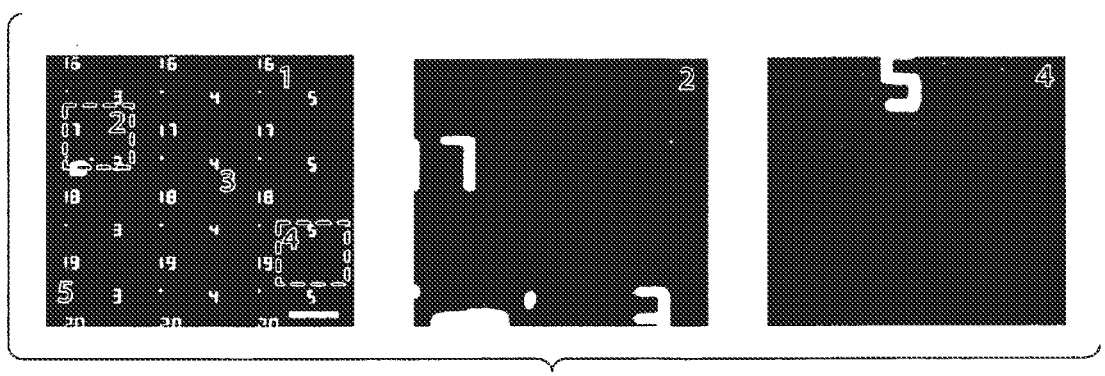
FIG. 14A shows optical micrographs of nanoscale objects, according to an embodiment.
Figure 14B:
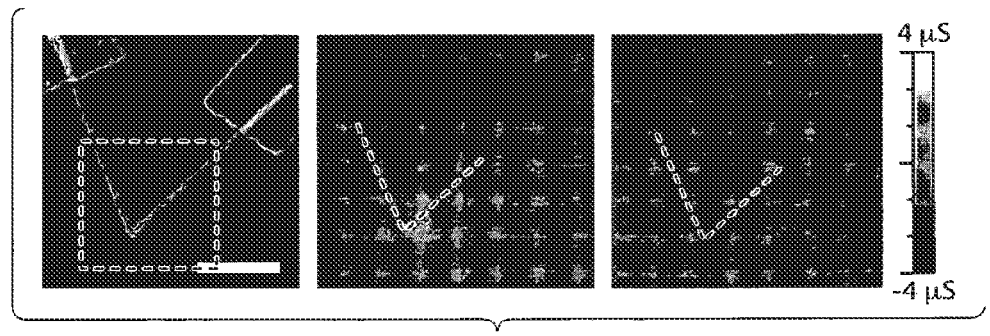
FIG. 14B shows an atomic force micrograph (left panel) and scanning gate micrographs (middle panel and right panel), according to an embodiment.

FIGS. 14A and 14B. 60° bent nanowires with integrated transistor elements. (A) (left) Optical micrograph of five 60° kinked nanowire structures; scale bar is 20 micrometers. The white numbers correspond to Au-metal markers defined on the device chip prior to deposition of the kinked nanowires. The middle and the right panels are the zoom-in optical microscopy images of nanowire 2 and 4, respectively. The images were recorded in bright-field mode. (B) Atomic force microscopy (AFM, left) and scanning gate microscopy (SGM, middle & right) images of a 60° kinked nanowire device. The scale bar in the AFM image is 2 micrometers. Measurements were carried out with a Digital Instruments Nanoscope Ma MultiMode AFM and metal-coated tips (Nanosensors, PPP-NCHPt). The SGM conductance maps were acquired in lift mode with lift height of 20 nm. The SGM images were recorded with a $V_{tip}$ of +10 V (middle) and −10 V (right), respectively, and $V_{sd}$ of 0.5 V. The device conductance is 4.2 microsiemens. The dark and bright regions correspond to reduced and enhanced conductance, respectively. The SGM data demonstrate the successful synthetic integration of an n-type field effect transistor (FET) immediately adjacent to the 60° probe tip, where the length of the active region of the FET is ~200 nm.

FIG. 15. Free-standing kinked nanowire probe fabrication. (A) Key fabrication steps include: (1) deposition and patterning of poly(methylmethacrylate) (PMMA) layer by electron-beam lithography (EBL); (2) deposition of SU-8 2000.5 photoresist over the entire chip; (3) deposition of kinked nanowires from isopropanol solution; (4) EBL patterning and subsequent curing (180° C., 20 min) of 300-400 nm SU-8 structure that will serve as flexible mechanical support for metal contacts; (5) deposition and (6) EBL patterning of methyl methacrylate (MMA) and PMMA double layers resist; and finally, (7) sequential Cr/Pd/Cr (1.5/50-80/50-80 nm) contact thermal evaporation and plasma-enhanced chemical vapor deposition of 40-60 nm $Si_3N_4$ contact passivation. The kinked nanowire probe devices are released from the (substrate) by removal of the initial PMMA layer during the lift-off process in acetone, where the built in stress in the Pd/Cr electrodes leads to predictable height and angle of the nanowire probe with respect to the substrate surface. The device tip is detailed in panel-8. (B) Dependence of the tip height and angle versus the length of relieved metal. The measurements were done in PBS solution for metal layers with Cr/Pd/Cr thickness of 1.5/75/50 nm. Inset, schematic of the device geometry; the typical nanowire arm length is 10 micrometers.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
    a nanoscale wire having at least one kink, wherein the nanoscale wire is a single crystal and at least a portion of a surface of the nanoscale wire is amphiphilic.

2. The article of claim 1, wherein the nanoscale wire further comprises a coating.

3. The article of claim 2, wherein the coating comprises a phospholipid.

4. The article of claim 1, wherein the nanoscale wire is a semiconductor.

5. The article of claim 1, wherein the nanoscale wire comprises a transistor.

6. The article of claim 1, wherein the nanoscale wire is disposed on a substrate.

7. The article of claim 1, wherein the nanoscale wire has a diameter less than 100 nm.

8. The article of claim 1, wherein the nanoscale wire has a length greater than 1 micron.

9. The article of claim 1, wherein the nanoscale wire has a length less than 100 nm.

10. The article of claim 1, wherein the nanoscale wire is capable of fusing with a lipid bilayer.

11. The article of claim 10, wherein the lipid bilayer is a cell membrane.

12. An article, comprising:
    a nanoscale wire having at least one kink, wherein the nanoscale wire is a single crystal and at least a portion of a surface of the nanoscale wire is capable of fusing with a lipid bilayer.

13. The article of claim 12, wherein the lipid bilayer is a cell membrane.

14. The article of claim 12, wherein the nanoscale wire is capable of fusing with at least two lipid bilayers.

15. The article of claim 12, wherein the nanoscale wire further comprises a coating.

16. The article of claim 15, wherein the coating comprises a phospholipid.

17. The article of claim 12, wherein the nanoscale wire is a semiconductor.

18. The article of claim 12, wherein the nanoscale wire comprises a field effect transistor.

19. The article of claim 12, wherein the nanoscale wire is disposed on a substrate.

20. The article of claim 12, wherein the nanoscale wire has a diameter less than 100 nm.

21. The article of claim 12, wherein the nanoscale wire has a length greater than 1 micron.

22. The article of claim 12, wherein the nanoscale wire has a length less than 100 nm.

23. The article of claim 12, wherein the nanoscale wire is amphiphilic.

24. An article, comprising:
a nanoscale wire having at least one kink, wherein the nanoscale wire is a single crystal and at least a portion of the nanoscale wire is capable of penetrating a lipid bilayer using chemical interactions.

25. The article of claim 24, wherein the nanoscale wire further comprises a coating.

26. The article of claim 25, wherein the coating comprises a phospholipid.

27. The article of claim 24, wherein the lipid bilayer is a cell membrane.

28. The article of claim 24, wherein the nanoscale wire is capable of penetrating at least two lipid bilayers.

29. The article of claim 24, wherein the nanoscale wire is a semiconductor.

30. The article of claim 24, wherein the nanoscale wire comprises a field effect transistor.

31. The article of claim 24, wherein the nanoscale wire is disposed on a substrate.

32. The article of claim 24, wherein the nanoscale wire has a diameter less than 100 nm.

33. The article of claim 24, wherein the nanoscale wire has a length greater than 1 micron.

34. The article of claim 24, wherein the nanoscale wire has a length less than 100 nm.

35. The article of claim 24, wherein the nanoscale wire is amphiphilic.

36. The article of claim 1, wherein the kink comprises a transition between a first substantially straight portion of the wire and a second substantially straight portion of the wire, wherein the transition region may have a linear length that is less than about 5% of the linear lengths of the substantially straight portions surrounding the transition region.

37. The article of claim 1, wherein the kink has an angle of about 120°.

38. The article of claim 12, wherein the kink comprises a transition between a first substantially straight portion of the wire and a second substantially straight portion of the wire, wherein the transition region may have a linear length that is less than about 5% of the linear lengths of the substantially straight portions surrounding the transition region.

39. The article of claim 12, wherein the kink has an angle of about 120°.

40. The article of claim 24, wherein the kink comprises a transition between a first substantially straight portion of the wire and a second substantially straight portion of the wire, wherein the transition region may have a linear length that is less than about 5% of the linear lengths of the substantially straight portions surrounding the transition region.

41. The article of claim 24, wherein the kink has an angle of about 120°.

* * * * *